US007777015B2

(12) United States Patent
Chauvaux et al.

(10) Patent No.: US 7,777,015 B2
(45) Date of Patent: Aug. 17, 2010

(54) **CYTOCHROME P-450 GENE CLUSTER FROM *RHODOCOCCUS RUBER* AND USES THEREOF IN ETHER FUEL CLEAVAGE**

(75) Inventors: Sylvie Chauvaux, Paris (FR); Isabelle Miras, Lechelle (FR); Pierre Beguin, Vincennes (FR)

(73) Assignee: Institut Francais du Petrole, Rueil-Malmaison (FR)

( * ) Notice: Subject to any disclaimer, the term of this patent is extended or adjusted under 35 U.S.C. 154(b) by 1252 days.

(21) Appl. No.: 10/739,003

(22) Filed: Dec. 19, 2003

(65) Prior Publication Data

US 2004/0214787 A1 Oct. 28, 2004

Related U.S. Application Data

(63) Continuation of application No. PCT/EP02/08066, filed on Jun. 20, 2002.

(30) Foreign Application Priority Data

Jun. 22, 2001 (EP) ................................ 01401667

(51) Int. Cl.
*C07H 21/02* (2006.01)
*A62D 3/00* (2007.01)
*C12N 1/00* (2006.01)

(52) U.S. Cl. ................ 536/23.1; 435/262.5; 435/252.3; 435/254.1; 435/254.11; 435/252.33; 435/255.1

(58) Field of Classification Search ...................... None
See application file for complete search history.

(56) References Cited

U.S. PATENT DOCUMENTS 6,040,154 A 3/2000 Fayolle et al.

OTHER PUBLICATIONS

Hexanucleotide Mix, 1997 Biochemicals Catalog, Boehringer Mannhein, cover and p. 95.*
Nagy I. et al 'Degradation of the thiocarbamate herbicide EPTC (S-ethyl dipropylcarbamothioate) and biosafening by *Rhodococcus* sp. strain NI86/21 involve an inducible cytochrome P-450 system and aldehyde dehydrogenase.' J Bacteriol. Feb. 1995;177(3):676-87.*
International Search Report in corresponding PCT Application No. PCT/EP02/08066.
Hernandez-Perez et al.; Biodegradation of ethyl t-butyl ether (ETBE), methyl t-butyl ether (MTBE) and t-amyl methyl ether (TAME) by *Gordonia terrae; Appl. Microbiol. Biotechnol.* (2001) 55:117-121.
Fayolle et al.; Isolation of two aerobic bacterial strains that degrade efficiently ethyl t-butyl ether (ETBE); *Biotechnology Letters* (Mar. 1998) 20(3):283-286.
Piveteau et al.; Biodegradation of tert-butyl alcohol and related xenobiotics by a methylotrophic bacterial isolate; *Appl. Microbiol. Biotechnol.* (2001) 55:369-373.
Kharoune et al.; Isolation and characterization of two aerobic bacterial strains that completely degrade ethyl tert-butyl ether (ETBE); *Appl. Microbiol. Biotechnol.* (2001) 55:348-353.
Steffan et al.; Biodegradation of the gasoline oxygenates methyl tert-butyl ether, ethyl tert-butyl ether, and tert-amyl methyl ether by propane-oxidizing bacteria; *Appl. Envir. Microbiol.* (Nov. 1997) 63(11):4216.4222.
Kharoune et al.; Aerobic biodegradation of an oxygenates mixture: ETBE, MTBE and TAME in an upflow fixed-bed reactor; *Wat. Res.* (2001) 35(7):1665-1674.
Nagy et al.; Degradation of the thiocarbamate herbicide EPTC (S-ethyl dipropylcarbamothioate) and Biosafening by *Rhodococcus* sp. strain N186/21 Involve an Inducible cytochrome p-450 system and aldehyde dehydrogenase; *J. Bacteriol.* (Feb. 1995) 177(3):676-687.
Chauvaux et al.; Cloning of a genetically unstable cytochrome p-450 gene cluster involved in degradation of the pollutant ethyl tert-butyl ether by *Rhodococcus* rubber; *J. Bacteriol.* (Nov. 2001) 183(22)6551-6557.

* cited by examiner

*Primary Examiner*—Stephen Kapushoc
(74) *Attorney, Agent, or Firm*—Finnegan, Henderson, Farabow, Garrett & Dunner, L.L.P.

(57) ABSTRACT

The present invention is directed to a cytochrome P-450 gene cluster involved in the cleavage of ether fuel additives. More especially, the present invention pertains to the nucleic add sequence of genes responsible for the biodegradation of ethyl tert-butyl ether (ETBE) in *Rhodococcus ruber*, and to several applications ensuing from the knowledge of this sequence, such as probes and biosensors for detecting a pollution by an ether fuel, and for assessing the potential of a contaminated soil to cleave said ether fuel. The invention also pertains to methods for rendering a cell able to cleave ether fuel additives, and to recombinant bacteria useful for ether fuel depollution of a contaminated effluent.

10 Claims, 6 Drawing Sheets

Figure 1:
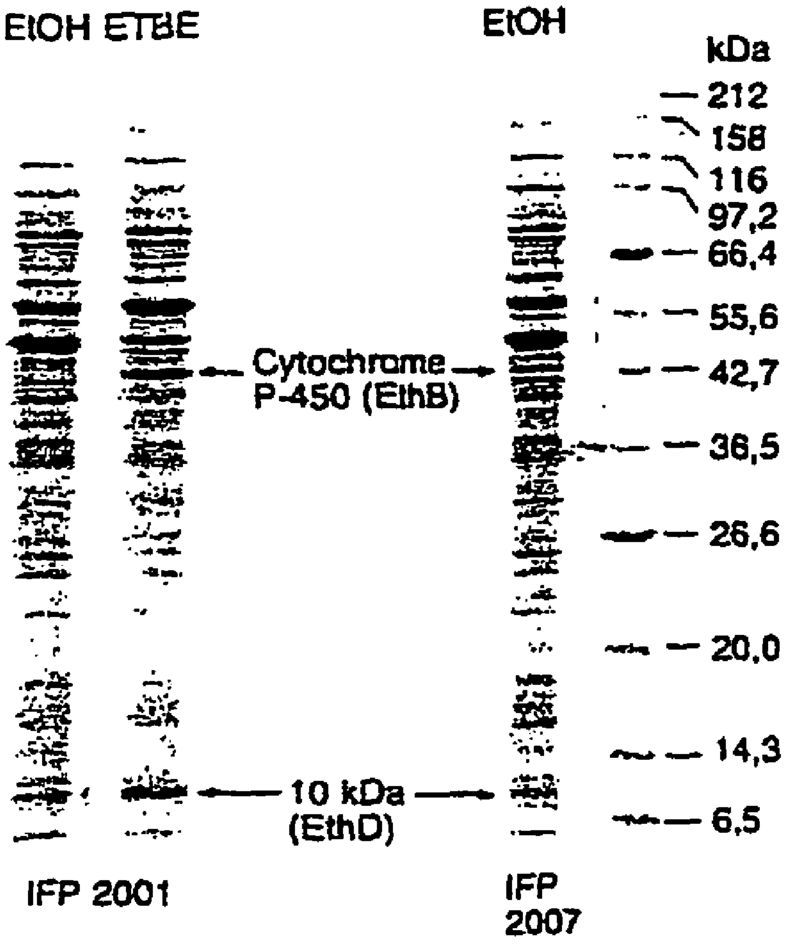

SEQUENCE LISTING

```
<160> NUMBER OF SEQ ID NOS: 25

<210> SEQ ID NO 1
<211> LENGTH: 23656
<212> TYPE: DNA
<213> ORGANISM: Rhodococcus ruber

<400> SEQUENCE: 1

ggatccgggc atgacgcgac ccttccgcta cccggtcacc ctgggcgcga gtggcccggt      60

ccgctccgct cggacggtcc ggcatggcac gatggaccgg ctgtgaacga gaccaccgac     120

accctcaccg tgctggccgt cgacgacgaa ccgccggccc tcgacgaact cgcgtacctg     180

ctgcggcggc gcgaggagat cggccacgtc cacaccgcgg gcgaggcgac caccgccctg     240

cggctgctgc gcgacggcgg aatcgacgcg gtgttcctcg acatcaacat gcccggcctc     300

gacggcctcg agctcgccgg catcctgcgc aacttcgcga acccgcccgc cgtcgtgttc     360

gtgaccgcgc acgacgaccg ggcggtggcg gcgttcgacc tcggggccgt cgactacctc     420

ctcaaacccc tgcgcgagga gcggctcgcc gaggcggtgc gccgcatcgc cgagcgccgc     480

cgcacccgcg aaaccgaatc cgctgccgcg ggtgccgcgg cctcggacga ggtgatcccc     540

gtcgaactcg gcggcgtgac cacgctggtg ccgcggtcgt ccgtgcagtg ggtcgaggcc     600

gacggcgact acgcacgcct gcacaccggc accggctccc acctcgtgcg catccccatc     660

tccacgctcg agagccgctg ggccgacgcc gggttcctgc gggtgcaccg ctcctatctg     720

gtggcgttgc ccctggtgac cggcatccgc agcgtcggtt ccggcctcgt ggtgtgcctg     780

cgcgccgagg agggcaagcc ggccgtcgaa ctgccggtga gccgtcgtca cacccgcgaa     840

ctcaaggacc gcctgatccg cggcccgatg cagacctgga cgagcagatg agtccgtccg     900

gcggctcacc gtcgcgcagc tcggggagcg gttcgggcgg cccgccgccg cgtggttcgg     960

gcggcccgcc gccgcgtggt tcgggcggcc cgccgccgcg tggttcgggc ggcccgccgc    1020

cgcgtggttc gggcggcccg ccgccgcgtg gttcgggcgg cccgccgccg cgtggttcgg    1080

gcggcccgcc gccgcgggaa cgggtggtgc tcgcccagcg ccgcggtgcc cgcatggtgc    1140

gcacccgcgt ggaggtccag gaacagaccg aggtcgggga ggcgatggtg cgcggcctgg    1200

tccgcgccca gctcggcctc gccacgcggc tcgcgctcgt cgcggtgtgc ctgctgtgcg    1260

ccctgcccgt gctgttccac ttcgtgccgc acctgacgga cgtgaccgtg ctcggcatcc    1320

ggttgccgtg gctgctgctc ggcttcgtcg ggtacccgct gctgctcggc atcggccggc    1380
```

-continued

```
tctacgtccg cctggccgaa cgcaacgagc aggacttcac cgacctggtc gacgactgag   1440
cggcccatgg acaccggttc gatccccgtc gccaccgtcg tcggtctcgt cttcgccgcc   1500
gccgccaccg tcgcgatcgg catctacgga gtccggctgg cccgcaccac ctccgacttc   1560
ctcatcgcct cccgcagcgt cggaccccgc tggaacgccg ccgcgatctc cggtgaatac   1620
ctttccgctg cctcctttct cggcgtagcc ggactcatcg ccaagtacgg cgccgacgcc   1680
ctgtggtacc cggtgggctt caccgcgggc tacctgggtc tgctgctgtt cgtcgccgcc   1740
ccgctgcgcc ggtccggcgc ctacaccgtg ccggacttcg cggagttccg gctcggtgcg   1800
cgatggctgc gcaccctgtc gatggtgatc gtcgccgtcg tctgcgtgct ctacctcgtc   1860
ccccagttcc aaggcgcggg actgacgctg aacatcctgc tcggggttcc cgactgggtc   1920
ggcgtcgtcg cggtcgccgt catcgtcgtc ggcaacgtcg tcggcggcgg catgcgctcg   1980
atcaccttcg tccaggcgtt ccagtactgg ctcaagctca ccgccgtcgc ggtgcccgcc   2040
ctcgtgctcg tcgtccactt cttcgacgac gatcgcgccg tcggccggcc ggcgcccccg   2100
acggtcaccg agcgcaccac cgtcgacgtc accaccgatg tcgtcgtcca ggtcggcgag   2160
cccctcgcgg tcacggcgac cggacgggtc gacggacgga ccgtggacgg caccgtgctg   2220
ctcgcgcccg gtgagcacga ggtggccgcc ggcacggcgc tggtgctcga gcccggcgcg   2280
gccgtgccgg tggtggccgg ggcacccgcc accaacgacg actgggtcgc tcccggcggt   2340
gggatcgggg gcgcccaccc catgttccag gtgtattcgc tgatcctcgc caccttcctc   2400
ggcacgatgg gcttgccgca cgtgctggtg cgcttctaca ccaacccgga cgggcgagcg   2460
gcccgcatga cgtcgctcgc ggtgatcgcc ctgctcggcg tgttctatct gttcccgacg   2520
ctgctcgggg tgttcgcacg cctgtacgtg ccgcaactgc tcatcacggg ccgctccgat   2580
gcggccgtgc tgctgctgcc ggggtcggtg ctctccggac tgggtggcca gctgctcgcc   2640
gcgctcgtcg ccgcgggggc gatcgcggcg ttcctgtcca cgtcctcggg gttgctggtc   2700
agcgtcgccg gtgtgctgtc caccgacgtg ctgcgcggac gcgtgcgcga cttccggatc   2760
gcggccgtcc tcgcgggcct ggtgcccctc ggcctgtcgc tggcggtgac gtcgctggac   2820
ctgtcgcggg ccgtgggcct ggtgttcgcg gtggccgcct ccacgctgtg cccgctgctg   2880
atgctcggca tctggtggcg tgggctgacc gcggtcggcg cggccgccgg catggtgacc   2940
ggcgcggtgg tggccggggg cgcggccctg gtcgtcgtgc tggtgcggat cgatcccgag   3000
gccggtggcg gctgggtcgc cgccgtcgtc ggctacccgg ccgccgtgag tgtgccgctc   3060
gcgttcgcca ccatgatcgt ggtcagcctc gccacccgcg ctcgcgtccc ggcggacgtc   3120
gggcgggtct tctcccgcat gcacgtgccc gagcggctcg ggatgggccg ggaccgggaa   3180
ctcggggcgt tcgaggacac cggcgttccc gcagagcccc gcggaccggg ccagccgtcc   3240
ccgcgtgggg agcactgagc tgccactcgt cgcgcccggc agaccgttcg ccgcaccggg   3300
cgacagctca ccgtgtgacc ggtgccacct tcttttcgtg tgactccggt ctcactacgg   3360
tctactggta gtacgcctca caggggcgat ccctgaagcc acgaccaagg agtcggcagt   3420
gaccacagct cacctcggca agggcggggc gctcgaacgc cgcacgcccg atgcgcagga   3480
cttcgtcgac atgcaggcga gtccggagtt ccaggacttg gggtcgaggg agcaaacccg   3540
cccaatccgg cgctaaggat ttaccgcaca tagtgtcata ctatgtgcga tcggataacg   3600
ggtcgatgcg ccccagtcgg gcgactcgag aacctgtgcg cggtagtagt tcgaggttga   3660
tgacatgggg cgggttcaca ggttgtcgac gtcggcgagt gatgtgcggc tggccgatgc   3720
agtacagatc tacttggcga cgattatggt gtcgaacacc cgcgcaacct acgcggcggc   3780
```

-continued

```
gctgaatcgg ttggtggtcg acttcggggc ggatacgaat gtggcgttgc tgggctcgga   3840
gccggatcgg gtcagtggct ggttcacctt cgtgtggggt ggcaagtcgg cgaagacgtt   3900
taacatccga ttgactgcgc tggggtcggc gtgcgcatat tggcgcgatc agcagtggtt   3960
ggccggcgat ccgttagtgc ggttgcgaac gcggcccgca ccgccggaca ccagtagggc   4020
gttgagcaag gatcgggtca ccgagatctt gggatcggat gcggcccaga gggaacaggt   4080
gttatggcac atgctctacg aatccgcggc gcgtgccgag gaggtgttga tgctggatgt   4140
gcccgacctc gacacagcga accgctgcgc ggaggtgaca cgcaagggcg gggcacgcga   4200
actctgaacc accctggatc tgatggagac ctggttcaag ccacgtcgcg gtcggaggtg   4260
gctgtcgagc gttgttgacg gtactcgttt tcgtagtcga tgggcggttg gtatccgatc   4320
gaggagtgca ggcggctggt gttgaaccaa tgcacccagg aagccgtctc gcgctcgacc   4380
tcgctgcgcc cgctccacga cttctgccgg tcgatcagct cggtcttgta caacccgatc   4440
gtcgattcca tcaacgcatt gtcgagcgcg tcgccgacgc tgccgatcga tccagcgatg   4500
ccggattcga tcaacgcctc ggtgaacgcc agagacgtat actgggaacc cgcgtccgag   4560
tgatggacca aacccgttgc agtgaacgcg aagtcggacc ggcgacgtgt gaacaatgct   4620
tgctcgagta cacccgacac cagcggcgtc gccttcgtcg tcatgaccct ccacccgaga   4680
atccggcggg agaacacatc gaccacgaac gaggtgtaca cgaaaccaac caacgtccag   4740
caataagtaa aatcggcaac ccaccactgg tccggttgag tcggcgcgcc ccactgccgg   4800
gcaatcagat ccggatgtcg aggggcacga tcatcgcgtt cggtggtcac cgtacgccgg   4860
cgtccgcgga caacaccctc tgctccgcag atcgtcatca accgagcgac ctgatcgcgg   4920
ccgatctcgt gaccagcgcg tttcattgca tgccagattt tcttggctcc gtagaggcgt   4980
ctgtttgcca cgaagaaccc gtgaacggtg ttcgtggcgt acgcctcttc cagtgccgct   5040
gcggagacgg tgccgcgttt cttggcggcg tagtaggtgg acggggcgat cttgatgccg   5100
tgctctttga gtacggtgca gatcgggtcg accccgaaaa ggtggcggta ttcgtcgatg   5160
tactcgacga tcaccgaagt cggcggtcga cctccgccgc tgcgaaaaac gctgacgctg   5220
tcttgagaat ctcgttggct cttcgcaatt cggagttctc acgccgtagc gccttcaact   5280
cctcgtcgcg gtcaactcct gcgacgggcc cgtgtgcctc ggtggccgga tcgttcttct   5340
cgatccagtt tcggatcgtc gccgggttga tatcgagcag agccccgacg tgcttacggg   5400
ccgttacttt cggctcgccg tactccttga gccggtcgcg atacatccga actgcccgct   5460
cccgcgtctc agcatcgaac ttccttggtg cacccatatc tgcattctcc tggtgagatc   5520
acagtctcca ccagccccag ggtggttcac tcgtcgcgtg gcagagcgct accgcgcgcc   5580
tgttgccgcg gatgctggcc gaccgcacga gcggtccact gttcctcacc gcccgaaaag   5640
cccgatcgtc cgtggctgca cgcgatgtcg actcgtcgac ggggcgggca cggctgtctt   5700
atcggcgcgc ggccgagatg ttcgaaggcc acaccgtcca ctacgacgac ggcccgtaca   5760
cgctgcacca actacggcat tcacggctga cgcatgcggc cgaggatggc gcgtcgatgc   5820
cggtgttgat gacgctgtcg ggtcagatgt cggtgcgagg ccttgtcgag tacgcaagaa   5880
tctccgacga tgggctacgg cgctttcagg ccgagagcga tccggcggcg cgtcggccag   5940
ggcggtgatc ggcgcagtga gtcgcaccgt caatcgctct cgtgggcatc gggatcgcgc   6000
agcggccggt gtgttccacc gaggtctggt aagtggaagg cgtagtggcc gtcgataccg   6060
atgtgggtgc ggataaacgc cgatagtcgc tgcgcgtcgg cgtcgagcac cggatagccc   6120
```

-continued

```
tgcgcgcgta gctgttccag agcgcggttg gtgtataacg tattccacag aactgtgcag   6180
ttgagcacca accccagtgc ggagagttga tcttccatgc cttcgtagta ggtacgggtc   6240
atctccccct tctttccgtg gtagatccgg cgcgccaggt cgtgacgccc ttctccgaga   6300
ttggcctgaa tcttgccttc cctgcggtac ggttcgtcgt cggccaggcg caggatgtgc   6360
agggttttga agatccgccc ataatgggcg atcgcttgac ccaagggggt aggtttcccg   6420
tcccgggaga tcatccgggt gacgtcgtga gcggagacct cacactcgtt gatcgacact   6480
gcaactcggc acatgtcctc ccagtgcgcg gcgatcttgt cggtgtcgat gtgaccccga   6540
gcggcctggt tgagtggccc gtagtccgcg gaccggtcga accgccataa ccgctgatcg   6600
ggcagattcg ctaactgcgg ccggtatctc ttgccgatca ggtgcatcag accgaacacg   6660
atgtcgctgt aggagccggt gtcggtgacg atctcgtcgg gagcttttcc gccctgctga   6720
agctgcacca catcgatgaa gttcagggag tcgcggggcg tcccggacac gaccttggcc   6780
gccagcccgg cggactggtc gttgagcatg ttcaaccagg tgatcccgcg cttacggccg   6840
aagtacttcg ggttcggtct cgcgtggatg gtgcggaccg gaaccacgaa ccgcataccg   6900
tccaccgagg cgagtagccc accaccccac agctgcgcca attcgatctc ggactgggcc   6960
tctaccagct cgacgttggc cgcagtcaac gtctccacgc gaacgtagtt ctggtcgaca   7020
tggtgcagac ggtcacgggt cagcgcgtga acaccagggc tggtcaccgg tgtgaaaccc   7080
acgttcatcg cgtgcgcgca cagtacggcc gcgaccgaca atccgagatc ggcgacgcgg   7140
gcaccgttgc cggaggcgtg ggtgaacgac tcggtgaacc ggggcaccca ggacatgact   7200
tccaagacca gctcgggcag gtcgacctcg ggcaacattg tctggacccg gcgacgtaga   7260
tcgaccagcg acggcgggtc cggttctgct ttcagcgagg cgaggtggag acgcccgtcc   7320
tcgccgacgc tcgccggacc gtcactgtcc aacctcgcgg cgacctcacg gtaggcagtg   7380
tccatcgtgg cggcatgctc ggcgagcagc ggtgccggat cgcccggtag gttcaacgcg   7440
ttcatcccgg cctcgcggga gcgatcccat gcttgcccga ccagcagctg ggctcgaggg   7500
tcacgccatc gcgtcgagtg cggggcaaag atgttgcgat acttgagatg tcgatggaac   7560
tgctccagta ggcacaaggt gtaggcggcg cggtcgaccg tctccggtgg ccgaggatcg   7620
cgatagacca gcctcttcca gccgccaccg atgagatcat ggtcgatctg gcgggcatcg   7680
agccagctcg cgggtagttt cgacttcgtc gacatcagct caccgagggt cttcatcgct   7740
gccagtaccg ccgcaccgtc cgcggtcgct ccgaacgtca cggtgttcat cagccggggc   7800
aggaacaccc ggaccgtggc caagcgtccc gccaactctt ccaggcgctg cccatcgagt   7860
tccgcgtcat cgaccggcac caactcgtcg atcaccgcta ccgacgcgcg cagctcactt   7920
ttggtcgcga tgttctcgat cagatcccac agcatgttga cgctgaggtt cggctcgacc   7980
tcactcatct ccaacagcat cttgaccgct gccgagagct tgcctgcatg acgtgagacg   8040
cgtgggtatc ggcgcagctt ctcatcgcgt gactcacgtt cggccttcga catcaggttc   8100
gtgaccatca aaagatcgaa caactcgagc acgtcatcag ttgccctgtt cgacagcact   8160
ttcaccgtgg cgaccagcac cgccaggcga ttgcggcggg gctcgatgcg ccgcaatgta   8220
ggggccttac tcgatagccc gtaggtggcc agtgcgatca ctcgacgctg cggaaccatc   8280
gacacatcca gtgattgccc gcccagcccg atgaggtcgg tcaaccgttc cagggcgtcg   8340
agcataccct tcgagctggt ccggaacacg ccccggcgaa gccgctccag ttcgctgaca   8400
cgacgtttgc cctcgggtac atcgagcaac gccagtagcg ccgaagcaga accagcagtg   8460
agttgatcgg tcagctgact ccacaaccgc tgatcagcgg cctgtcgccc gtcggtcacc   8520
```

-continued

```
acacgtacca gagtgcgggg accgggaagc agcgcctgat gttcacgtaa ccagtcgacc   8580
gcactggcga atatcgcttt cggcccatcg ccggtgaccc acgcctgatc ggcgacccac   8640
gccgccaact ccgcctcgac ctcagcatag gaactcaagc cgtactcgcg ctggatctcc   8700
caagcgtgtt cgagtttggt tttcttccgc tcggtgtact gcttcacaca cgaggagtcc   8760
tcgataccca actgctcggc gagatagtcg accagctcca ggggcgcatc gagcggatca   8820
gccaaaaaca ttccgagttg gcggactgtc acgatctgaa gggcgaaccc caaccggttg   8880
tagtcacgac gccgaccagc gatcagcttc cggtcctcgt catcgaggta gaaaaaccgt   8940
tccagctcaa cacgggacaa cgccccgaac cggccgtagc cgccctcatc ggtcatgccg   9000
acatgaaatc acctgtaggt ccacgccgcc gacgtcaccg ctcgatgttc atcgcttagc   9060
gccggattgg gcgggttttg ctcctcgacc cccgcgtcac cctcgagttc ggcgactggt   9120
gggacggctg ggtcccagct aagtgacagt tgtgacatcg cgtgacaacg aaccgaccgg   9180
caccgacaac tgacagagat gagatttggc atcaccgcac gtgaagcggt gttttcaact   9240
gtgcccccgg caggattcga acctgcggcc ttctgctccg gaggcagacg ctctatcccc   9300
tgagctacgg gggctcaacg ggcgatggct agcgtagcgc actcgcaacg ctcgacccaa   9360
tccggctggt cacaacgcct atcgccctcc gccggaaccg atatgactgt ttcgcggctg   9420
ccgacgcgtt gtggatacga actgggcgcg aactggctag acaccgtctg ttgcgatgcc   9480
ccacactggt tacccacaga tatgacatcg gtcacagcct ggccgacgtc gagccagatg   9540
gtttggaggc ctgaatggga acgtcgacga cgagcacgtc gcggccggcc agaccgacgt   9600
cgtccgtctt ctcgctgaag aagctggagg agtcggaacg ggcggtgacc accgccttct   9660
atccgcacaa ggcgtcgatg gagcgcaatc agcagcagtt ccgggggatt ctcaccgtcc   9720
agaacgtcgg tccgatcacc atcggtgaac tggactacaa cagcgaggtc tccctggact   9780
tcccgcacat caccaacggg taccacgtga acgtcccggt cgagcactcg atgtcgtcca   9840
gatcgcgcgg gcgggaggtc cacatcaccc cgaagcacgg cgcgatgtac cgcaaggagg   9900
cggacgcgct gctcaagccg agcaggcgac tgcacatgac cgcggtcaag ttcgacagcg   9960
ccgccctgga acagacgttg tcggccctgc tcggcgaacc cgtcgaggtg gatctcgaac  10020
tcgcatccgg gatcaatctc gagcgcggcc tgggcaagga gtggtgggac ctgctctccg  10080
acgtccgtcg gcagatcgac ggcggcaaca cgctcttcag ctgccggatg gtcgccgacc  10140
cgctggccca gtcgctcatg accggcttcc tcctcgcgag tacccatcag ttctccgagc  10200
aactgcattc gggcgactcg gtggcgacgc ccgagtcgtt gaagctcgtc gaggacgcca  10260
tcatggcgcg gctgtccgaa tcgttcacgt tcaccgagat cgcgcaggaa gtcgggatca  10320
gcctccgggc catccagcgc ggattcgccc accacatcgg cacgaccccg tcccaattcg  10380
tgcggaccga acgactgcga cggcccacg  tcgacctcgt cgccggtgat ccgtcgacca  10440
cccgggtcgc cgatgtcgca gcccgctggg gcttcaccca tctcggccgg ttctcggcgc  10500
agtaccgaaa gctctacggc gtgagtccct cggacacctt gcgctcctag ggttctcgac  10560
gcccagccct actccccctc acccacccac ccaccccatc tcctctcgat gccgacccct  10620
gcggggtacg gccagtgacg tgatcccgaa acccctctcc ggcaatcgac gcatgccctt  10680
gccgcgcgtg aaaggaagcg aagttgacga cgaccaccgc gacgctcacc gacgtgatca  10740
tcatcggcgc cgggcagggc ggcctgcagg cagcgatgtc gctgcgcgat cacggctata  10800
cgggccgcct gacgatcgtc ggcgacgaac cgggcctgcc gtatcagcgt cctccgctgt  10860
```

-continued

```
cgaaggcgta tctcatcaac gacgacgcca tgtcggagga actcctgctg ctccggccgc  10920
actcggtgtt cgagcgactc gacatcgacc tcatcaccgg tgacggcgtc acccgcatcg  10980
accgggtccg cagcaccgtg tcgctgagtt cgggtcgcga actggccttc gaccacctga  11040
tcctggccac cggcgcccgg ccgcgggagc tgagcgtgcc gggcgccgac ctcgcgggag  11100
tggaggcact gcgtacgtgc gacgacgcga aggcgatccg cgcggggctc accggcccgg  11160
cacgggtcgt ggtgatcggc ggcggctttg tcgggaccga ggtggccgcc gcggcgacca  11220
agcgaggcca ctccgtgacg atcgtcgaca tggaggcccg tctcctcaat cgggctgtgt  11280
ccccggagat ctccgcactc gtcacggcgg cgcatcgccg caggggaacc gcggtcgtcc  11340
tgaacgccgg cgtcagccgg ctgtgcggct ccgacggcac cgtcgaagcc gtggaactca  11400
ctgacgggca acggattccg gccgacttcg tagttgtcgg catcggcgtc gtgcccaaca  11460
cggagatcgc ccacgacgcc ggcctcgccg tcgacaacgg cattctcgtc gatgaccggt  11520
tgcgcaccaa cgaccaccgg atcagtgcga tcggcgactg cgcgcgattc ccgtgcgcac  11580
acgccgacgg ccagatgctg cgcctcgaat cggtgcagaa cgccgtcgac cacgcacgac  11640
acgtcgccgc ccgactcatg ggcgacgcag gaccctacga cgccgtgccg tggttctgga  11700
ccgaccagtg cggactgaag atccagatcg ccggaatcgg cgcgcagggc gccgagtcgg  11760
tggtgatcgg cgacgaggca gcagaacgat gttcggtgct gcggttccgc tccggcgaac  11820
tgtcctgtgt ggagtcggtc aacagcagcg gcgagcacat ggccgcacgc aagatcctgc  11880
gcggtggacc gcgcccggtg gcgcccgtcg acgggtcacc cgctgccttc gacctcaaac  11940
acatcgcccg ggaggtcgcc acggctcgct gagaacccag tcctgacacc tagtggtgca  12000
ctgcaccttt caccgacaca cccctgatcg aggaggaatc tatgacactg tcactggcca  12060
cggcccagga acgctatgcc accgatgcgg acgtcttcgc acacgacacc ctggtcgatc  12120
cctacgacac gtatcggtcg ctgcgcgaca tcggccgtgt gtcgtacatg acccggtacg  12180
acacgtgggc gctcacccgc tacgacgagg tccgtcacgc gctcggcgac tggcagacgt  12240
tcagttcggc gcagggaatc ggaatgagca cggcactcaa cgaggcgtgg aaggacttcg  12300
cgccgtgcaa ggacggcgcc gaccacctgc ccatgcggaa gttgatgatg caggacctcg  12360
gccccaaagc cgccgcggcc tacaaggaga agatccagca ggccgccgtg acgctcgtcg  12420
aggagttgct cgatcgccgc gagttcgacg cggtgctcga cttcgcccag atgatgccga  12480
tgcgggtgtt catggaggtg ctcggtgtcg agcccgacat cgaacagcgc cgcacgatgc  12540
tgcactgggg gaccgacacc tacaactgcg cggcgccgga cggcctctac gacgacaccc  12600
tgcccagcat ggacaagctc tacagctggg cgctggagaa catcactccg gagaccgcac  12660
gcgagggcag cgtcgccgcg tcgacgtggg agtcggtgga acgcggcgac atcaccgacg  12720
tgcaggcggt cgcgaccctg gcggcttacg tcaccgccgg actcgacacc accgccggta  12780
ccctcggcaa cacgatcgcg cagttcgcgg cgaacccgga ccagtgggcc atcgtccgcg  12840
acgaccccaa gaccatcccg ggcgcgatcc tcgagggcat ccggttcgac agcgtggcgc  12900
agtggttcac ccgcgtgacc acccgcgacg tcgagtacga cgacatcgtc atccccgcgg  12960
ggtcgcggac gtatcactcc tacgcggcgg caaaccggga cgagcggcac taccgcgacc  13020
ccgactcctt cgacgtgctg cgcaacccca ccgaccacgt ggggttcggg tacggcccgc  13080
acatgtgcgt cggaaagtcg gtgtccaaca ccgagatgat cgccctgtgg accgaactcg  13140
gccgccgggt ggatcgcatc gagcagatcg gcccgaagaa gcagcacatc aacaacctca  13200
tccgcagcct cgattcgctg cccgtgcgga tctacccgaa gtgatgccga tgcccaagat  13260
```

-continued

```
caccttctcc caatcggacg ggtcgtcgat caccgtcgat gcgtcgctgg accagagcgt  13320
catgcaggcc gccgtcgccg caggtatcga cggcatcctc gccgagtgcg gtggcaacgc  13380
cacgtgttcc acctgccacg tgtacgtcga acccgagcaa ctcgggctcc tcgcggacct  13440
gagcgccgaa gaagacgaca tgctcgactg cgccgaggcc gaacgtcgga gcaacagccg  13500
gctggcgtgt cagctgccgg tcaccaccga cctcgacggg ctccggctgg aggtccccga  13560
cgcgttctga acgcgtccgg caccagccgc ctcccaccac acaagaactg ttcgcagtac  13620
caatcaccaa ggagtgcacc atgtatcaga tcgtggcctg ctacggccag cccaccgaca  13680
ccgaggcgtt cgacacctac tacgacagca cccacgtgcc gctggcgaac aagctccccg  13740
gcctcgtcga ctacatcacg gtcaagtgcg tctcggcact gcccggggaa ggggtcccgt  13800
actacatggt cgcgaccctg accttcaact cggagcgcga cgtcaaggcc gcgcttgagt  13860
cgccggagat ggacgccgcg aaggccgacg tcgccaactt cgccaccggc ggcctggccc  13920
tctacatcgg ggatgaggtc gaccggacct agttcgaccg gccaccgtgt gcgcgacgat  13980
gggaaacatg ctgcaccaca gcgtgtttcc catcgttcgc accgtcacga ccgagtgcgc  14040
accaccccga acatcacgat ccccgactgt cacgatcccc cgccccagga gccgcaacca  14100
tgtccgcctt gatgaagacg ttcaccatgc tcgaggtctc cgtcctcgtt gacggtgacc  14160
gacaggtgcg ggtcggcatc gtcgtcgggt accgcggtgg cgtcgctcat cgctgcgttc  14220
ctccttcgct caggactcgt ttcaccacga gcgagctcgt cggtgaaatc gttaccagtg  14280
tgacgggctg gccgcgtgtt gtgggaacgg atgtcgccag cgttgcgctg atggcgatca  14340
tcaccgtgcg gggctgggtg ccggtgaagt cggagtagat cagattggcg ggggaaatgg  14400
cggtgggtgc cacgcgttgt ccgatggtga tctgctcggc aatggtcgcc ggcatggtga  14460
ttcctacgcg gtgaaagacg tactggactg cctgggtttg gccgattcgg ccgttctggg  14520
ggccgtcgac ggtgcctgcc gtgtcgtcag cggtgatgcg gtcggatacg agcatggtgg  14580
cgtatcgggc gacggtggct gcggtgctgg tggtgagggt ggaggtcagc gggggttgtt  14640
ggtagggggc ggtggacagt ttcgtgacgc attcgcggat tcgggtcggc agggtcgagg  14700
ggatgtcggt gagggaagcg taggggttgg tgctggggag ggtggcggtc tcggtcggct  14760
gggcggtggt gtggagggtg gtggtcgagg gggtcgtcgg gtcttgcgtt gccggtgcgg  14820
tggtggtgtc ggaggagggg cagaggggtc gaggccgagc acgctgtcgc attgatagag  14880
gaagtcttgc tgggtttggc tcatgccgcc gcctccgacg aaggcggtca tcatcgcgca  14940
ggatgctgcg gtgatgagta tggctgcggc cgtgaggatt ccggcgacgg ttttcatggt  15000
cgagctcacc taggagtcct gtctgacgtg gtggtcgggc gctaggcggg ggcggggttg  15060
ttgcgcctgg ctctcggctg ctgaggtcgt gtcccggcgg cgctgccagg gggaggtgac  15120
cggcggcggg gcggtgccgg gggcggctgg ggtgaccatg acgtgggtgg tttgtgctgt  15180
gggggctgcc gttggcggcg tcgtcgatgg cggtgtcgtc gatgagggcg tggaggtggt  15240
cggtgtcggc tcgcgagggg gtgtttcgtc gtcgtgggtg gtggtgggca tggcgtgggt  15300
ggtggtggtg ctgggtgtgc gcggtgcggg gagtggttct cgtcggccgg cggtaggcgg  15360
agggtcgtcg tatccggtgc cggtggggag cggtaggtga ggttgtggcg cgggattgcg  15420
gttgcggtgt cggggagtgc ccggtgaggc gaggtcaggg gtgggcgcgg tggggtcgcg  15480
cggcgcgtcg ggggcagagg ggtggggtag ctcgacggtg ggtgtgcgag gcgcggtggc  15540
acggtgtgcg gctttgcttg ccgcgtgggc tgcggcttgt ttgccggcgg tgcggacggc  15600
```

-continued

```
ggcgctggcc gcggccgagg ttccgccggt ggcagctgcg gcggcggcct gcgcggcgac  15660
gggggccagg gaccggacca ctccgcgttt gcggtcggtg ggcttggctg gaggggtggt  15720
ggtgggttgg ccgggatcgg cgggcagtgc gtgggtttcg gtgagggcgc ggatcttctt  15780
gactgcggag ccctgcgaga taccggtgac ggtctgcgcg gcgctgaggg cgtgggtgag  15840
cgcgctgggc ccgacgggtg tgctggcggt gggtgagccg cccatggcgg agatattggc  15900
ggagatcttc tttgccgcct gttctcgggt gctgcgggta cgccagagca ggacgatcgc  15960
gacgatcatg gcgatgccgg cgacggtgat gccggcggct ccgctgaggt tgttagagct  16020
caggagtgat cgcaggatga gtgaccatcc gccgaggaag acgacgtaca ccgtcatcgc  16080
cagcgcgcac aggatcatgt cggcgaagct gttccagagc gcggtttgtc cggtgccggg  16140
aatgaagccg gtgatggcga atccgacgat caccttgaat cctgcccaga tggcctggaa  16200
ggcggtgagg atgatgcgga agccgagata gcaggcgaag gccaagagca ggaaggagaa  16260
caggatcagc gctacgccgg tgccgatctg ggatccgctg gggttgtccg cgacgtgttt  16320
catggcgtgt gaggcgtcgg cgccgcagtc ttctatggcg tctttgacct ggtcttcttc  16380
gccgctgcgt tgcccggagc tccaggccgc tctgcatgct ggggattgct cgtcgacgac  16440
ggcgccgaag ttccactgtt gcaggggttg gcggatgaat gtggtggtca gctgtcgttg  16500
gagctgctcg atcatggcgg cgccgtcact ggtgggttgg ccggacatcg atgtggagat  16560
ggcgattccg gtgtctcggc cctgggagag cagtccgtcg gaaccgatga ttctgccgac  16620
ggggttgccg aggacggtgc cgccgaggac ggcgacgacg aggatcatgc acaactgtgc  16680
cacggccttg gaggtgtggc cgcggaggaa gtaccaggcc accgggacgg agccgacggc  16740
cacggccgcg ccgacgattg cgggggtcga gatcgtctgg gtgaggctgt tggagatcgc  16800
gacgatcgag gtggagaaca gattcaacca gttgaaagac atggcccagc acacgaacca  16860
gacgccgaag gacacgacca tgagccagat tccgaactcc gactgcagga ttgaggacag  16920
tggcaggttg gtggggtgcc agagcgatcc gtggtcggtg gagaacatgt aggccgagac  16980
ccctactccg tcctcgtctt gcagatccat ccagccgatc gctgcggcgg cgctgacttg  17040
ggtggctgcg gcggcctggg gggccagcca ggtggagagg acgacccagg tgtggatggc  17100
tatctgtgac cacacgatcc agcggcgcag tctggtcttg ttgatccagg aagttgtgtg  17160
ggccagcagg atcgctgggt cgagacgagg gaggatctgg tcggcggtca cgccgtggtg  17220
ccatgcgtgt gtccaggtga gggtggtcat acggtggcct gacgtccggg ggtggtgccg  17280
gcggcgcggc ggcggtcggg ggaggacagg ccgaggacct tggctcggcc catgcggccg  17340
agggcatcgc gcatgaagca ctcgccgcgg cgattggggg gaacggaatc gaagtcttcg  17400
ctgcgcatgg gtgcagtttc ggtttggagc tgcttgacga ggtgcgcgtt ctcgtcggtg  17460
tcgatgtcga gccagcgcag tgactcttcg gccagagcac ggtcgcgctg acggaagacg  17520
aagcgggtgg gcacgagttt gaggctgtcg ttgtcccagt cgctgccggg tgcgtgggag  17580
gccaggctca tgagggcgtt gttcttgcgt ccgtcgcggg cgaactcggt ggtgatgcgg  17640
cggccgaccg gggcgacggt gaagtggtaa gcctcatcgc cgttgaatgc gccgaggcga  17700
tcggagtgga acagggagaa gcgggcggtg accccgatca gcgcgtagat gcaggtgccg  17760
agtttggcgc gggcagagat ctgccggtag aggtgcgggt tcaggagttc gtcgcgatcg  17820
gcgagggcaa ggcggtgggt gcggatcact gttgccggac tgggggtcga ggagcaaacc  17880
cgcccaatcc ggcgctaagg atttaccgca catagtgtca tactatgtgc gatcggataa  17940
cgggtcgatg cgccccagtc gggcgactcg agaacctgtg cgcggtagta gttcgaggtt  18000
```

-continued

```
gatgacatgg ggcgggttca caggttgtcg acgtcggcga gtgatgtgcg gctggccgat  18060
gcagtacaga tctacttggc gacgattatg gtgtcgaaca cccgcgcaac ctacgcggcg  18120
gcgctgaatc ggttggtggt cgacttcggg gcggatacga atgtggcgtt gctgggctcg  18180
gagccggatc gggtcagtgg ctggttcacc ttcgtgtggg gtggcaagtc ggcgaagacg  18240
tttaacatcc gattgactgc gctggggtcg gcgtgcgcat attggcgcga tcagcagtgg  18300
ttggccggcg atccgttagt gcggttgcga acgcggcccg caccgccgga caccagtagg  18360
gcgttgagca aggatcgggt caccgagatc ttgggatcgg atgcggccca gagggaacag  18420
gtgttatggc acatgctcta cgaatccgcg gcgcgtgccg aggaggtgtt gatgctggat  18480
gtgcccgacc tcgacacagc gaaccgctgc gcggaggtga cacgcaaggg cggggcacgc  18540
gaactctgaa ccaccctgga tctgatggag acctggttca agccacgtcg cggtcggagg  18600
tggctgtcga gcgttgttga cggtactcgt tttcgtagtc gatgggcggt tggtatccga  18660
tcgaggagtg caggcggctg gtgttgaacc aatgcaccca ggaagccgtc tcgcgctcga  18720
cctcgctgcg cccgctccac gacttctgcc ggtcgatcag ctcggtcttg tacaacccga  18780
tcgtcgattc catcaacgca ttgtcgagcg cgtcgccgac gctgccgatc gatccagcga  18840
tgccggattc gatcaacgcc tcggtgaacg ccagagacgt atactgggaa cccgcgtccg  18900
agtgatggac caaacccgtt gcagtgaacg cgaagtcgga ccggcgacgt gtgaacaatg  18960
cttgctcgag tacacccgac accagcggcg tcgccttcgt cgtcatgacc ctccacccga  19020
gaatccggcg ggagaacaca tcgaccacga acgaggtgta cacgaaacca accaacgtcc  19080
agcaataagt aaaatcggca acccaccact ggtccggttg agtcggcgcg ccccactgcc  19140
gggcaatcag atccggatgt cgaggggcac gatcatcgcg ttcggtggtc accgtacgcc  19200
ggcgtccgcg gacaacaccc tctgctccgc agatcgtcat caaccgagcg acctgatcgc  19260
ggccgatctc gtgaccagcg cgtttcattg catgccagat tttcttggct ccgtagaggc  19320
gtctgtttgc cacgaagaac ccgtgaacgg tgttcgtggc gtacgcctct tccagtgccg  19380
ctgcggagac ggtgccgcgt ttcttggcgg cgtagtaggt ggacggggcg atcttgatgc  19440
cgtgctcttt gagtacggtg cagatcgggt cgaccccgaa aaggtggcgg tattcgtcga  19500
tgtactcgac gatcaccgaa gtcggcggtc gacctccgcc gctgcgaaaa acgctgacgc  19560
tgtcttgaga atctcgttgg ctcttcgcaa ttcggagttc tcacgccgta gcgccttcaa  19620
ctcctcgtcg cggtcaactc ctgcgacggg cccgtgtgcc tcggtggccg gatcgttctt  19680
ctcgatccag tttcggatcg tcgccgggtt gatatcgagc agagccccga cgtgcttacg  19740
ggccgttact ttcggctcgc cgtactcctt gagccggtcg cgatacatcc gaactgcccg  19800
ctcccgcgtc tcagcatcga acttccttgg tgcacccata tctgcattct cctggtgaga  19860
tcacagtctc caccagcccc agggtggttc actcgtcgcg tggcagagcg ctaccgcgcg  19920
cctgttgccg cggatgctgg ccgaccgcac gagcggtcca ctgttcctca ccgcccgaaa  19980
agcccgatcg tccgtggctg cacgcgatgt cgactcgtcg acggggcggg cacggctgtc  20040
ttatcggcgc gcggccgaga tgttcgaagg ccacaccgtc cactacgacg acggcccgta  20100
cacgctgcac caactacggc attcacggct gacgcatgcg gccgaggatg gcgcgtcgat  20160
gccggtgttg atgacgctgt cgggtcagat gtcggtgcga ggccttgtcg agtacgcaag  20220
aatctccgac gatgggctac ggcgctttca ggccgagagc gatccggcgg cgcgtcggcc  20280
agggcggtga tcggcgcagt gagtcgcacc gtcaatcgct ctcgtgggca tcgggatcgc  20340
```

-continued

```
gcagcggccg gtgtgttcca ccgaggtctg gtaagtggaa ggcgtagtgg ccgtcgatac  20400
cgatgtgggt gcggataaac gccgatagtc gctgcgcgtc ggcgtcgagc accggatagc  20460
cctgcgcgcg tagctgttcc agagcgcggt tggtgtataa cgtattccac agaactgtgc  20520
agttgagcac caaccccagt gcggagagtt gatcttccat gccttcgtag taggtacggg  20580
tcatctcccc cttctttccg tggtagatcc ggcgcgccag gtcgtgacgc ccttctccga  20640
gattggcctg aatcttgcct tccctgcggt acggttcgtc gtcggccagg cgcaggatgt  20700
gcagggtttt gaagatccgc ccataatggg cgatcgcttg acccaagggg gtaggtttcc  20760
cgtcccggga gatcatccgg gtgacgtcgt gagcggagac ctcacactcg ttgatcgaca  20820
ctgcaactcg gcacatgtcc tcccagtgcg cggcgatctt gtcggtgtcg atgtgacccc  20880
gagcggcctg gttgagtggc ccgtagtccg cggaccggtc gaaccgccat aaccgctgat  20940
cgggcagatt cgctaactgc ggccggtatc tcttgccgat caggtgcatc agaccgaaca  21000
cgatgtcgct gtaggagccg gtgtcggtga cgatctcgtc gggagctttt ccgccctgct  21060
gaagctgcac cacatcgatg aagttcaggg agtcgcgggg cgtcccggac acgaccttgg  21120
ccgccagccc ggcggactgg tcgttgagca tgttcaacca ggtgatcccg cgcttacggc  21180
cgaagtactt cgggttcggt ctcgcgtgga tggtgcggac cggaaccacg aaccgcatac  21240
cgtccaccga ggcgagtagc ccaccacccc acagctgcgc caattcgatc tcggactggg  21300
cctctaccag ctcgacgttg gccgcagtca acgtctccac gcgaacgtag ttctggtcga  21360
catggtgcag acggtcacgg gtcagcgcgt gaacaccagg gctggtcacc ggtgtgaaac  21420
ccacgttcat cgcgtgcgcg cacagtacgg ccgcgaccga caatccgaga tcggcgacgc  21480
gggcaccgtt gccggaggcg tgggtgaacg actcggtgaa ccggggcacc caggacatga  21540
cttccaagac cagctcgggc aggtcgacct cgggcaacat tgtctggacc cggcgacgta  21600
gatcgaccag cgacggcggg tccggttctg ctttcagcga ggcgaggtgg agacgcccgt  21660
cctcgccgac gctcgccgga ccgtcactgt ccaacctcgc ggcgacctca cggtaggcag  21720
tgtccatcgt ggcggcatgc tcggcgagca gcggtgccgg atcgcccggt aggttcaacg  21780
cgttcatccc ggcctcgcgg gagcgatccc atgcttgccc gaccagcagc tgggctcgag  21840
ggtcacgcca tcgcgtcgag tgcggggcaa agatgttgcg atacttgaga tgtcgatgga  21900
actgctccag taggcacaag gtgtaggcgg cgcggtcgac cgtctccggt ggccgaggat  21960
cgcgatagac cagcctcttc cagccgccac cgatgagatc atggtcgatc tggcgggcat  22020
cgagccagct cgcgggtagt ttcgacttcg tcgacatcag ctcaccgagg gtcttcatcg  22080
ctgccagtac cgccgcaccg tccgcggtcg ctccgaacgt cacggtgttc atcagccggg  22140
gcaggaacac ccggaccgtg gccaagcgtc ccgccaactc ttccaggcgc tgcccatcga  22200
gttccgcgtc atcgaccggc accaactcgt cgatcaccgc taccgacgcg cgcagctcac  22260
ttttggtcgc gatgttctcg atcagatccc acagcatgtt gacgctgagg ttcggctcga  22320
cctcactcat ctccaacagc atcttgaccg ctgccgagag cttgcctgca tgacgtgaga  22380
cgcgtgggta tcggcgcagc ttctcatcgc gtgactcacg ttcggccttc gacatcaggt  22440
tcgtgaccat caaaagatcg aacaactcga gcacgtcatc agttgccctg ttcgacagca  22500
ctttcaccgt ggcgaccagc accgccaggc gattgcggcg gggctcgatg cgccgcaatg  22560
taggggcctt actcgatagc ccgtaggtgg ccagtgcgat cactcgacgc tgcggaacca  22620
tcgacacatc cagtgattgc ccgcccagcc cgatgaggtc ggtcaaccgt tccagggcgt  22680
cgagcatacc cttcgagctg gtccggaaca cgccccggcg aagccgctcc agttcgctga  22740
```

-continued

```
cacgacgttt gccctcgggt acatcgagca acgccagtag cgccgaagca gaaccagcag  22800
tgagttgatc ggtcagctga ctccacaacc gctgatcagc ggcctgtcgc ccgtcggtca  22860
ccacacgtac cagagtgcgg ggaccgggaa gcagcgcctg atgttcacgt aaccagtcga  22920
ccgcactggc gaatatcgct ttcggcccat cgccggtgac ccacgcctga tcggcgaccc  22980
acgccgccaa ctccgcctcg acctcagcat aggaactcaa gccgtactcg cgctggatct  23040
cccaagcgtg ttcgagtttg gttttcttcc gctcggtgta ctgcttcaca cacgaggagt  23100
cctcgatacc caactgctcg gcgagatagt cgaccagctc caggggcgca tcgagcggat  23160
cagccaaaaa cattccgagt tggcggactg tcacgatctg aagggcgaac cccaaccggt  23220
tgtagtcacg acgccgacca gcgatcagct tccggtcctc gtcatcgagg tagaaaaacc  23280
gttccagctc aacacgggac aacgccccga accggccgta gccgccctca tcggtcatgc  23340
cgacatgaaa tcacctgtag gtccacgccg ccgacgtcac cgctcgatgt tcatcgctta  23400
gcgccggatt gggcgggttt tgctcctcga cccccgactt gcgccgccgg ctccggcggt  23460
tcgtcttccc gatgacgggg ctcttcctca cctggtactt cgtgtacgtc ctgctggcca  23520
cctacgccgc cgacttcatg gcgaccaagg tgctcggcaa catcaacctc ggcctgatcc  23580
tcggactcgg ccaattcgtc tcgacgttcg tcatcaccgc gctctacgtg cggttcgcca  23640
atcgtgacct ggatcc                                                  23656
```

<210> SEQ ID NO 2
<211> LENGTH: 12342
<212> TYPE: DNA
<213> ORGANISM: Rhodococcus ruber

<400> SEQUENCE: 2

```
cgtcaccctc gagttcggcg actggtggga cggctgggtc ccagctaagt gacagttgtg     60
acatcgcgtg acaacgaacc gaccggcacc gacaactgac agagatgaga tttggcatca    120
ccgcacgtga agcggtgttt tcaactgtgc ccccggcagg attcgaacct gcggccttct    180
gctccggagg cagacgctct atcccctgag ctacgggggc tcaacgggcg atggctagcg    240
tagcgcactc gcaacgctcg acccaatccg gctggtcaca acgcctatcg ccctccgccg    300
gaaccgatat gactgtttcg cggctgccga cgcgttgtgg atacgaactg ggcgcgaact    360
ggctagacac cgtctgttgc gatgccccac actggttacc cacagatatg acatcggtca    420
cagcctggcc gacgtcgagc cagatggttt ggaggcctga atgggaacgt cgacgacgag    480
cacgtcgcgg ccggccagac cgacgtcgtc cgtcttctcg ctgaagaagc tggaggagtc    540
ggaacgggcg gtgaccaccg ccttctatcc gcacaaggcg tcgatggagc gcaatcagca    600
gcagttccgg gggattctca ccgtccagaa cgtcggtccg atcaccatcg gtgaactgga    660
ctacaacagc gaggtctccc tggacttccc gcacatcacc aacgggtacc acgtgaacgt    720
cccggtcgag cactcgatgt cgtccagatc gcgcgggcgg gaggtccaca tcaccccgaa    780
gcacggcgcg atgtaccgca aggaggcgga cgcgctgctc aagccgagca ggcgactgca    840
catgaccgcg gtcaagttcg acagcgccgc cctggaacag acgttgtcgg ccctgctcgg    900
cgaacccgtc gaggtggatc tcgaactcgc atccgggatc aatctcgagc gcggcctggg    960
caaggagtgg tgggacctgc tctccgacgt ccgtcggcag atcgacggcg gcaacacgct   1020
cttcagctgc cggatggtcg ccgacccgct ggcccagtcg ctcatgaccg gcttcctcct   1080
cgcgagtacc catcagttct ccgagcaact gcattcgggc gactcggtgg cgacgcccga   1140
```

-continued

```
gtcgttgaag ctcgtcgagg acgccatcat ggcgcggctg tccgaatcgt tcacgttcac   1200
cgagatcgcg caggaagtcg ggatcagcct ccgggccatc cagcgcggat tcgcccacca   1260
catcggcacg accccgtccc aattcgtgcg gaccgaacga ctgcgacggg cccacgtcga   1320
cctcgtcgcc ggtgatccgt cgaccacccg ggtcgccgat gtcgcagccc gctggggctt   1380
cacccatctc ggccggttct cggcgcagta ccgaaagctc tacggcgtga gtccctcgga   1440
caccttgcgc tcctagggtt ctcgacgccc agccctactc cccctcaccc acccacccac   1500
cccatctcct ctcgatgccg acccctgcgg ggtacggcca gtgacgtgat cccgaaaccc   1560
ctctccggca atcgacgcat gcccttgccg cgcgtgaaag gaagcgaagt tgacgacgac   1620
caccgcgacg ctcaccgacg tgatcatcat cggcgccggg cagggcggcc tgcaggcagc   1680
gatgtcgctg cgcgatcacg gctatacggg ccgcctgacg atcgtcggcg acgaaccggg   1740
cctgccgtat cagcgtcctc cgctgtcgaa ggcgtatctc atcaacgacg acgccatgtc   1800
ggaggaactc ctgctgctcc ggccgcactc ggtgttcgag cgactcgaca tcgacctcat   1860
caccggtgac ggcgtcaccc gcatcgaccg ggtccgcagc accgtgtcgc tgagttcggg   1920
tcgcgaactg gccttcgacc acctgatcct ggccaccggc gcccggccgc gggagctgag   1980
cgtgccgggc gccgacctcg cgggagtgga ggcactgcgt acgtgcgacg acgcgaaggc   2040
gatccgcgcg gggctcaccg gcccggcacg ggtcgtggtg atcggcggcg gctttgtcgg   2100
gaccgaggtg gccgccgcgg cgaccaagcg aggccactcc gtgacgatcg tcgacatgga   2160
ggcccgtctc ctcaatcggg ctgtgtcccc ggagatctcc gcactcgtca cggcggcgca   2220
tcgccgcagg ggaaccgcgg tcgtcctgaa cgccggcgtc agccggctgt gcggctccga   2280
cggcaccgtc gaagccgtgg aactcactga cgggcaacgg attccggccg acttcgtagt   2340
tgtcggcatc ggcgtcgtgc ccaacacgga gatcgcccac gacgccggcc tcgccgtcga   2400
caacggcatt ctcgtcgatg accggttgcg caccaacgac caccggatca gtgcgatcgg   2460
cgactgcgcg cgattcccgt gcgcacacgc cgacggccag atgctgcgcc tcgaatcggt   2520
gcagaacgcc gtcgaccacg cacgacacgt cgccgcccga ctcatgggcg acgcaggacc   2580
ctacgacgcc gtgccgtggt tctggaccga ccagtgcgga ctgaagatcc agatcgccgg   2640
aatcggcgcg cagggcgccg agtcggtggt gatcggcgac gaggcagcag aacgatgttc   2700
ggtgctgcgg ttccgctccg gcgaactgtc ctgtgtggag tcggtcaaca gcagcggcga   2760
gcacatggcc gcacgcaaga tcctgcgcgg tggaccgcgc ccggtggcgc ccgtcgacgg   2820
gtcacccgct gccttcgacc tcaaacacat cgcccgggag gtcgccacgg ctcgctgaga   2880
acccagtcct gacacctagt ggtgcactgc acctttcacc gacacacccc tgatcgagga   2940
ggaatctatg acactgtcac tggccacggc ccaggaacgc tatgccaccg atgcggacgt   3000
cttcgcacac gacaccctgg tcgatcccta cgacacgtat cggtcgctgc gcgacatcgg   3060
ccgtgtgtcg tacatgaccc ggtacgacac gtgggcgctc acccgctacg acgaggtccg   3120
tcacgcgctc ggcgactggc agacgttcag ttcggcgcag ggaatcggaa tgagcacggc   3180
actcaacgag gcgtggaagg acttcgcgcc gtgcaaggac ggcgccgacc acctgcccat   3240
gcggaagttg atgatgcagg acctcggccc caaagccgcc gcggcctaca aggagaagat   3300
ccagcaggcc gccgtgacgc tcgtcgagga gttgctcgat cgccgcgagt tcgacgcggt   3360
gctcgacttc gcccagatga tgccgatgcg ggtgttcatg gaggtgctcg gtgtcgagcc   3420
cgacatcgaa cagcgccgca cgatgctgca ctgggggacc gacacctaca actgcgcggc   3480
gccggacggc ctctacgacg acaccctgcc cagcatggac aagctctaca gctgggcgct   3540
```

-continued

```
ggagaacatc actccggaga ccgcacgcga gggcagcgtc gccgcgtcga cgtgggagtc   3600
ggtggaacgc ggcgacatca ccgacgtgca ggcggtcgcg accctggcgg cttacgtcac   3660
cgccggactc gacaccaccg ccggtaccct cggcaacacg atcgcgcagt tcgcggcgaa   3720
cccggaccag tgggccatcg tccgcgacga ccccaagacc atcccgggcg cgatcctcga   3780
gggcatccgg ttcgacagcg tggcgcagtg gttcacccgc gtgaccaccc gcgacgtcga   3840
gtacgacgac atcgtcatcc ccgcggggtc gcggacgtat cactcctacg cggcggcaaa   3900
ccgggacgag cggcactacc gcgaccccga ctccttcgac gtgctgcgca accccaccga   3960
ccacgtgggg ttcgggtacg gcccgcacat gtgcgtcgga aagtcggtgt ccaacaccga   4020
gatgatcgcc ctgtggaccg aactcggccg ccgggtggat cgcatcgagc agatcggccc   4080
gaagaagcag cacatcaaca acctcatccg cagcctcgat tcgctgcccg tgcggatcta   4140
cccgaagtga tgccgatgcc caagatcacc ttctcccaat cggacgggtc gtcgatcacc   4200
gtcgatgcgt cgctggacca gagcgtcatg caggccgccg tcgccgcagg tatcgacggc   4260
atcctcgccg agtgcggtgg caacgccacg tgttccacct gccacgtgta cgtcgaaccc   4320
gagcaactcg ggctcctcgc ggacctgagc gccgaagaag acgacatgct cgactgcgcc   4380
gaggccgaac gtcggagcaa cagccggctg gcgtgtcagc tgccggtcac caccgacctc   4440
gacgggctcc ggctggaggt ccccgacgcg ttctgaacgc gtccggcacc agccgcctcc   4500
caccacacaa gaactgttcg cagtaccaat caccaaggag tgcaccatgt atcagatcgt   4560
ggcctgctac ggccagccca ccgacaccga ggcgttcgac acctactacg acagcaccca   4620
cgtgccgctg gcgaacaagc tccccggcct cgtcgactac atcacggtca agtgcgtctc   4680
ggcactgccc ggggaagggg tcccgtacta catggtcgcg accctgacct tcaactcgga   4740
gcgcgacgtc aaggccgcgc ttgagtcgcc ggagatggac gccgcgaagg ccgacgtcgc   4800
caacttcgcc accggcggcc tggccctcta catcggggat gaggtcgacc ggacctagtt   4860
cgaccggcca ccgtgtgcgc gacgatggga aacatgctgc accacagcgt gtttcccatc   4920
gttcgcaccg tcacgaccga gtgcgcacca ccccgaacat cacgatcccc gactgtcacg   4980
atcccccgcc ccaggagccg caaccatgtc cgccttgatg aagacgttca ccatgctcga   5040
ggtctccgtc ctcgttgacg gtgaccgaca ggtgcgggtc ggcatcgtcg tcgggtaccg   5100
cggtggcgtc gctcatcgct gcgttcctcc ttcgctcagg actcgtttca ccacgagcga   5160
gctcgtcggt gaaatcgtta ccagtgtgac gggctggccg cgtgttgtgg gaacggatgt   5220
cgccagcgtt gcgctgatgg cgatcatcac cgtgcggggc tgggtgccgg tgaagtcgga   5280
gtagatcaga ttggcggggg aaatggcggt gggtgccacg cgttgtccga tggtgatctg   5340
ctcggcaatg gtcgccggca tggtgattcc tacgcggtga aagacgtact ggactgcctg   5400
ggtttggccg attcggccgt tctgggggcc gtcgacggtg cctgccgtgt cgtcagcggt   5460
gatgcggtcg gatacgagca tggtggcgta tcgggcgacg gtggctgcgg tgctggtggt   5520
gagggtggag gtcagcgggg gttgttggta gggggcggtg gacagtttcg tgacgcattc   5580
gcggattcgg gtcggcaggg tcgaggggat gtcggtgagg gaagcgtagg ggttggtgct   5640
ggggagggtg gcggtctcgg tcggctgggc ggtggtgtgg agggtggtgg tcgagggggt   5700
cgtcgggtct tgcgttgccg gtgcggtggt ggtgtcggag gaggggcaga ggggtcgagg   5760
ccgagcacgc tgtcgcattg atagaggaag tcttgctggg tttggctcat gccgccgcct   5820
ccgacgaagg cggtcatcat cgcgcaggat gctgcggtga tgagtatggc tgcggccgtg   5880
```

-continued

```
aggattccgg cgacggtttt catggtcgag ctcacctagg agtcctgtct gacgtggtgg   5940
tcgggcgcta ggcgggggcg gggttgttgc gcctggctct cggctgctga ggtcgtgtcc   6000
cggcggcgct gccaggggga ggtgaccggc ggcggggcgg tgccgggggc ggctggggtg   6060
accatgacgt gggtggtttg tgctgtgggg gctgccgttg gcggcgtcgt cgatggcggt   6120
gtcgtcgatg agggcgtgga ggtggtcggt gtcggctcgc gagggggtgt ttcgtcgtcg   6180
tgggtggtgg tgggcatggc gtgggtggtg gtggtgctgg gtgtgcgcgg tgcggggagt   6240
ggttctcgtc ggccggcggt aggcggaggg tcgtcgtatc cggtgccggt ggggagcggt   6300
aggtgaggtt gtggcgcggg attgcggttg cggtgtcggg gagtgcccgg tgaggcgagg   6360
tcaggggtgg gcgcggtggg gtcgcgcggc gcgtcggggg cagaggggtg gggtagctcg   6420
acggtgggtg tgcgaggcgc ggtggcacgg tgtgcggctt tgcttgccgc gtgggctgcg   6480
gcttgtttgc cggcggtgcg gacggcggcg ctggccgcgg ccgaggttcc gccggtggca   6540
gctgcggcgg cggcctgcgc ggcgacgggg gccagggacc ggaccactcc gcgtttgcgg   6600
tcggtgggct tggctggagg ggtggtggtg ggttggccgg gatcggcggg cagtgcgtgg   6660
gtttcggtga gggcgcggat cttcttgact gcggagccct gcgagatacc ggtgacggtc   6720
tgcgcggcgc tgagggcgtg ggtgagcgcg ctgggcccga cgggtgtgct ggcggtgggt   6780
gagccgccca tggcggagat attggcggag atcttctttg ccgcctgttc tcgggtgctg   6840
cgggtacgcc agagcaggac gatcgcgacg atcatggcga tgccggcgac ggtgatgccg   6900
gcggctccgc tgaggttgtt agagctcagg agtgatcgca ggatgagtga ccatccgccg   6960
aggaagacga cgtacaccgt catcgccagc gcgcacagga tcatgtcggc gaagctgttc   7020
cagagcgcgg tttgtccggt gccgggaatg aagccggtga tggcgaatcc gacgatcacc   7080
ttgaatcctg cccagatggc ctggaaggcg gtgaggatga tgcggaagcc gagatagcag   7140
gcgaaggcca agagcaggaa ggagaacagg atcagcgcta cgccggtgcc gatctgggat   7200
ccgctggggt tgtccgcgac gtgtttcatg gcgtgtgagg cgtcggcgcc gcagtcttct   7260
atggcgtctt tgacctggtc ttcttcgccg ctgcgttgcc cggagctcca ggccgctctg   7320
catgctgggg attgctcgtc gacgacggcg ccgaagttcc actgttgcag gggttggcgg   7380
atgaatgtgg tggtcagctg tcgttggagc tgctcgatca tggcggcgcc gtcactggtg   7440
ggttggccgg acatcgatgt ggagatggcg attccggtgt ctcggccctg ggagagcagt   7500
ccgtcggaac cgatgattct gccgacgggg ttgccgagga cggtgccgcc gaggacggcg   7560
acgacgagga tcatgcacaa ctgtgccacg gccttggagg tgtggccgcg gaggaagtac   7620
caggccaccg ggacggagcc gacggccacg gccgcgccga cgattgcggg ggtcgagatc   7680
gtctgggtga ggctgttgga gatcgcgacg atcgaggtgg agaacagatt caaccagttg   7740
aaagacatgg cccagcacac gaaccagacg ccgaaggaca cgaccatgag ccagattccg   7800
aactccgact gcaggattga ggacagtggc aggttggtgg ggtgccagag cgatccgtgg   7860
tcggtggaga acatgtaggc cgagacccct actccgtcct cgtcttgcag atccatccag   7920
ccgatcgctg cggcggcgct gacttgggtg gctgcggcgg cctggggggc cagccaggtg   7980
gagaggacga cccaggtgtg gatggctatc tgtgaccaca cgatccagcg gcgcagtctg   8040
gtcttgttga tccaggaagt tgtgtgggcc agcaggatcg ctgggtcgag acgagggagg   8100
atctggtcgg cggtcacgcc gtggtgccat gcgtgtgtcc aggtgagggt ggtcatacgg   8160
tggcctgacg tccgggggtg gtgccggcgg cgcggcggcg gtcgggggag gacaggccga   8220
ggaccttggc tcggcccatg cggccgaggg catcgcgcat gaagcactcg ccgcggcgat   8280
```

-continued

```
tggggggaac ggaatcgaag tcttcgctgc gcatgggtgc agtttcggtt tggagctgct   8340
tgacgaggtg cgcgttctcg tcggtgtcga tgtcgagcca gcgcagtgac tcttcggcca   8400
gagcacggtc gcgctgacgg aagacgaagc gggtgggcac gagtttgagg ctgtcgttgt   8460
cccagtcgct gccgggtgcg tgggaggcca ggctcatgag ggcgttgttc ttgcgtccgt   8520
cgcgggcgaa ctcggtggtg atgcggcggc cgaccggggc gacggtgaag tggtaagcct   8580
catcgccgtt gaatgcgccg aggcgatcgg agtggaacag ggagaagcgg gcggtgaccc   8640
cgatcagcgc gtagatgcag gtgccgagtt tggcgcgggc agagatctgc cggtagaggt   8700
gcgggttcag gagttcgtcg cgatcggcga gggcaaggcg gtgggtgcgg atcactgttg   8760
ccggactggg ggtcgaggag caaacccgcc caatccggcg ctaaggattt accgcacata   8820
gtgtcatact atgtgcgatc ggataacggg tcgatgcgcc ccagtcgggc gactcgagaa   8880
cctgtgcgcg gtagtagttc gaggttgatg acatggggcg ggttcacagg ttgtcgacgt   8940
cggcgagtga tgtgcggctg gccgatgcag tacagatcta cttggcgacg attatggtgt   9000
cgaacacccg cgcaacctac gcggcggcgc tgaatcggtt ggtggtcgac ttcggggcgg   9060
atacgaatgt ggcgttgctg ggctcggagc cggatcgggt cagtggctgg ttcaccttcg   9120
tgtggggtgg caagtcggcg aagacgttta acatccgatt gactgcgctg ggtcggcgt   9180
gcgcatattg gcgcgatcag cagtggttgg ccggcgatcc gttagtgcgg ttgcgaacgc   9240
ggcccgcacc gccggacacc agtagggcgt tgagcaagga tcgggtcacc gagatcttgg   9300
gatcggatgc ggcccagagg gaacaggtgt tatggcacat gctctacgaa tccgcggcgc   9360
gtgccgagga ggtgttgatg ctggatgtgc ccgacctcga cacagcgaac cgctgcgcgg   9420
aggtgacacg caagggcggg gcacgcgaac tctgaaccac cctggatctg atggagacct   9480
ggttcaagcc acgtcgcggt cggaggtggc tgtcgagcgt tgttgacggt actcgttttc   9540
gtagtcgatg ggcggttggt atccgatcga ggagtgcagg cggctggtgt tgaaccaatg   9600
cacccaggaa gccgtctcgc gctcgacctc gctgcgcccg ctccacgact tctgccggtc   9660
gatcagctcg gtcttgtaca acccgatcgt cgattccatc aacgcattgt cgagcgcgtc   9720
gccgacgctg ccgatcgatc cagcgatgcc ggattcgatc aacgcctcgg tgaacgccag   9780
agacgtatac tgggaacccg cgtccgagtg atggaccaaa cccgttgcag tgaacgcgaa   9840
gtcggaccgg cgacgtgtga acaatgcttg ctcgagtaca cccgacacca gcggcgtcgc   9900
cttcgtcgtc atgaccctcc acccgagaat ccggcgggag aacacatcga ccacgaacga   9960
ggtgtacacg aaaccaacca acgtccagca ataagtaaaa tcggcaaccc accactggtc  10020
cggttgagtc ggcgcgcccc actgccgggc aatcagatcc ggatgtcgag gggcacgatc  10080
atcgcgttcg gtggtcaccg tacgccggcg tccgcggaca acaccctctg ctccgcagat  10140
cgtcatcaac cgagcgacct gatcgcggcc gatctcgtga ccagcgcgtt tcattgcatg  10200
ccagattttc ttggctccgt agaggcgtct gtttgccacg aagaacccgt gaacggtgtt  10260
cgtggcgtac gcctcttcca gtgccgctgc ggagacggtg ccgcgtttct tggcggcgta  10320
gtaggtggac ggggcgatct tgatgccgtg ctctttgagt acggtgcaga tcgggtcgac  10380
cccgaaaagg tggcggtatt cgtcgatgta ctcgacgatc accgaagtcg gcggtcgacc  10440
tccgccgctg cgaaaaacgc tgacgctgtc ttgagaatct cgttggctct tcgcaattcg  10500
gagttctcac gccgtagcgc cttcaactcc tcgtcgcggt caactcctgc gacgggcccg  10560
tgtgcctcgg tggccggatc gttcttctcg atccagtttc ggatcgtcgc cgggttgata  10620
```

-continued

```
tcgagcagag ccccgacgtg cttacgggcc gttactttcg gctcgccgta ctccttgagc  10680

cggtcgcgat acatccgaac tgcccgctcc cgcgtctcag catcgaactt ccttggtgca  10740

cccatatctg cattctcctg gtgagatcac agtctccacc agccccaggg tggttcactc  10800

gtcgcgtggc agagcgctac cgcgcgcctg ttgccgcgga tgctggccga ccgcacgagc  10860

ggtccactgt tcctcaccgc ccgaaaagcc cgatcgtccg tggctgcacg cgatgtcgac  10920

tcgtcgacgg ggcgggcacg gctgtcttat cggcgcgcgg ccgagatgtt cgaaggccac  10980

accgtccact acgacgacgg cccgtacacg ctgcaccaac tacggcattc acggctgacg  11040

catgcggccg aggatggcgc gtcgatgccg gtgttgatga cgctgtcggg tcagatgtcg  11100

gtgcgaggcc ttgtcgagta cgcaagaatc tccgacgatg ggctacggcg ctttcaggcc  11160

gagagcgatc cggcggcgcg tcggccaggg cggtgatcgg cgcagtgagt cgcaccgtca  11220

atcgctctcg tgggcatcgg gatcgcgcag cggccggtgt gttccaccga ggtctggtaa  11280

gtggaaggcg tagtggccgt cgataccgat gtgggtgcgg ataaacgccg atagtcgctg  11340

cgcgtcggcg tcgagcaccg gatagccctg cgcgcgtagc tgttccagag cgcggttggt  11400

gtataacgta ttccacagaa ctgtgcagtt gagcaccaac cccagtgcgg agagttgatc  11460

ttccatgcct tcgtagtagg tacgggtcat ctcccccttc tttccgtggt agatccggcg  11520

cgccaggtcg tgacgccctt ctccgagatt ggcctgaatc ttgccttccc tgcggtacgg  11580

ttcgtcgtcg gccaggcgca ggatgtgcag ggttttgaag atccgcccat aatgggcgat  11640

cgcttgaccc aagggggtag gtttcccgtc ccgggagatc atccgggtga cgtcgtgagc  11700

ggagacctca cactcgttga tcgacactgc aactcggcac atgtcctccc agtgcgcggc  11760

gatcttgtcg gtgtcgatgt gaccccgagc ggcctggttg agtggcccgt agtccgcgga  11820

ccggtcgaac cgccataacc gctgatcggg cagattcgct aactgcggcc ggtatctctt  11880

gccgatcagg tgcatcagac cgaacacgat gtcgctgtag gagccggtgt cggtgacgat  11940

ctcgtcggga gcttttccgc cctgctgaag ctgcaccaca tcgatgaagt tcagggagtc  12000

gcggggcgtc ccggacacga ccttggccgc cagcccggcg gactggtcgt tgagcatgtt  12060

caaccaggtg atcccgcgct tacggccgaa gtacttcggg ttcggtctcg cgtggatggt  12120

gcggaccgga accacgaacc gcataccgtc caccgaggcg agtagcccac caccccacag  12180

ctgcgccaat tcgatctcgg actgggcctc taccagctcg acgttggccg cagtcaacgt  12240

ctccacgcga acgtagttct ggtcgacatg gtgcagacgg tcacgggtca gcgcgtgaac  12300

accagggctg gtcaccggtg tgaaacccac gttcatcgcg tg                    12342
```

<210> SEQ ID NO 3
<211> LENGTH: 8766
<212> TYPE: DNA
<213> ORGANISM: Rhodococcus ruber

<400> SEQUENCE: 3

```
cgtcaccctc gagttcggcg actggtggga cggctgggtc ccagctaagt gacagttgtg     60

acatcgcgtg acaacgaacc gaccggcacc gacaactgac agagatgaga tttggcatca    120

ccgcacgtga agcggtgttt tcaactgtgc ccccggcagg attcgaacct gcggccttct    180

gctccggagg cagacgctct atcccctgag ctacgggggc tcaacgggcg atggctagcg    240

tagcgcactc gcaacgctcg acccaatccg gctggtcaca acgcctatcg ccctccgccg    300

gaaccgatat gactgtttcg cggctgccga cgcgttgtgg atacgaactg ggcgcgaact    360

ggctagacac cgtctgttgc gatgccccac actggttacc cacagatatg acatcggtca    420
```

-continued

```
cagcctggcc gacgtcgagc cagatggttt ggaggcctga atgggaacgt cgacgacgag    480
cacgtcgcgg ccggccagac cgacgtcgtc cgtcttctcg ctgaagaagc tggaggagtc    540
ggaacgggcg gtgaccaccg ccttctatcc gcacaaggcg tcgatggagc gcaatcagca    600
gcagttccgg gggattctca ccgtccagaa cgtcggtccg atcaccatcg gtgaactgga    660
ctacaacagc gaggtctccc tggacttccc gcacatcacc aacgggtacc acgtgaacgt    720
cccggtcgag cactcgatgt cgtccagatc gcgcgggcgg gaggtccaca tcaccccgaa    780
gcacggcgcg atgtaccgca aggaggcgga cgcgctgctc aagccgagca ggcgactgca    840
catgaccgcg gtcaagttcg acagcgccgc cctggaacag acgttgtcgg ccctgctcgg    900
cgaacccgtc gaggtggatc tcgaactcgc atccgggatc aatctcgagc gcggcctggg    960
caaggagtgg tgggacctgc tctccgacgt ccgtcggcag atcgacggcg gcaacacgct   1020
cttcagctgc cggatggtcg ccgacccgct ggcccagtcg ctcatgaccg gcttcctcct   1080
cgcgagtacc catcagttct ccgagcaact gcattcgggc gactcggtgg cgacgcccga   1140
gtcgttgaag ctcgtcgagg acgccatcat ggcgcggctg tccgaatcgt tcacgttcac   1200
cgagatcgcg caggaagtcg ggatcagcct ccgggccatc cagcgcggat tcgcccacca   1260
catcggcacg accccgtccc aattcgtgcg gaccgaacga ctgcgacggg cccacgtcga   1320
cctcgtcgcc ggtgatccgt cgaccacccg ggtcgccgat gtcgcagccc gctggggctt   1380
cacccatctc ggccggttct cggcgcagta ccgaaagctc tacggcgtga gtccctcgga   1440
caccttgcgc tcctagggtt ctcgacgccc agccctactc cccctcaccc acccacccac   1500
cccatctcct ctcgatgccg acccctgcgg ggtacggcca gtgacgtgat cccgaaaccc   1560
ctctccggca atcgacgcat gcccttgccg cgcgtgaaag gaagcgaagt tgacgacgac   1620
caccgcgacg ctcaccgacg tgatcatcat cggcgccggg cagggcggcc tgcaggcagc   1680
gatgtcgctg cgcgatcacg gctatacggg ccgcctgacg atcgtcggcg acgaaccggg   1740
cctgccgtat cagcgtcctc cgctgtcgaa ggcgtatctc atcaacgacg acgccatgtc   1800
ggaggaactc ctgctgctcc ggccgcactc ggtgttcgag cgactcgaca tcgacctcat   1860
caccggtgac ggcgtcaccc gcatcgaccg ggtccgcagc accgtgtcgc tgagttcggg   1920
tcgcgaactg gccttcgacc acctgatcct ggccaccggc gcccggccgc gggagctgag   1980
cgtgccgggc gccgacctcg cgggagtgga ggcactgcgt acgtgcgacg acgcgaaggc   2040
gatccgcgcg gggctcaccg gcccggcacg ggtcgtggtg atcggcggcg gctttgtcgg   2100
gaccgaggtg gccgccgcgg cgaccaagcg aggccactcc gtgacgatcg tcgacatgga   2160
ggcccgtctc ctcaatcggg ctgtgtcccc ggagatctcc gcactcgtca cggcggcgca   2220
tcgccgcagg ggaaccgcgg tcgtcctgaa cgccggcgtc agccggctgt gcggctccga   2280
cggcaccgtc gaagccgtgg aactcactga cgggcaacgg attccggccg acttcgtagt   2340
tgtcggcatc ggcgtcgtgc ccaacacgga gatcgcccac gacgccggcc tcgccgtcga   2400
caacggcatt ctcgtcgatg accggttgcg caccaacgac caccggatca gtgcgatcgg   2460
cgactgcgcg cgattcccgt gcgcacacgc cgacggccag atgctgcgcc tcgaatcggt   2520
gcagaacgcc gtcgaccacg cacgacacgt cgccgcccga ctcatgggcg acgcaggacc   2580
ctacgacgcc gtgccgtggt tctggaccga ccagtgcgga ctgaagatcc agatcgccgg   2640
aatcggcgcg cagggcgccg agtcggtggt gatcggcgac gaggcagcag aacgatgttc   2700
ggtgctgcgg ttccgctccg gcgaactgtc ctgtgtggag tcggtcaaca gcagcggcga   2760
```

-continued

```
gcacatggcc gcacgcaaga tcctgcgcgg tggaccgcgc ccggtggcgc ccgtcgacgg   2820
gtcacccgct gccttcgacc tcaaacacat cgcccgggag gtcgccacgg ctcgctgaga   2880
acccagtcct gacacctagt ggtgcactgc acctttcacc gacacacccc tgatcgagga   2940
ggaatctatg acactgtcac tggccacggc ccaggaacgc tatgccaccg atgcggacgt   3000
cttcgcacac gacaccctgg tcgatcccta cgacacgtat cggtcgctgc gcgacatcgg   3060
ccgtgtgtcg tacatgaccc ggtacgacac gtgggcgctc acccgctacg acgaggtccg   3120
tcacgcgctc ggcgactggc agacgttcag ttcggcgcag ggaatcggaa tgagcacggc   3180
actcaacgag gcgtggaagg acttcgcgcc gtgcaaggac ggcgccgacc acctgcccat   3240
gcggaagttg atgatgcagg acctcggccc caaagccgcc gcggcctaca aggagaagat   3300
ccagcaggcc gccgtgacgc tcgtcgagga gttgctcgat cgccgcgagt tcgacgcggt   3360
gctcgacttc gcccagatga tgccgatgcg ggtgttcatg gaggtgctcg gtgtcgagcc   3420
cgacatcgaa cagcgccgca cgatgctgca ctgggggacc gacacctaca actgcgcggc   3480
gccggacggc ctctacgacg acaccctgcc cagcatggac aagctctaca gctgggcgct   3540
ggagaacatc actccggaga ccgcacgcga gggcagcgtc gccgcgtcga cgtgggagtc   3600
ggtggaacgc ggcgacatca ccgacgtgca ggcggtcgcg accctggcgg cttacgtcac   3660
cgccggactc gacaccaccg ccggtaccct cggcaacacg atcgcgcagt tcgcggcgaa   3720
cccggaccag tgggccatcg tccgcgacga ccccaagacc atcccgggcg cgatcctcga   3780
gggcatccgg ttcgacagcg tggcgcagtg gttcacccgc gtgaccaccc gcgacgtcga   3840
gtacgacgac atcgtcatcc ccgcggggtc gcggacgtat cactcctacg cggcggcaaa   3900
ccgggacgag cggcactacc gcgaccccga ctccttcgac gtgctgcgca accccaccga   3960
ccacgtgggg ttcgggtacg gcccgcacat gtgcgtcgga aagtcggtgt ccaacaccga   4020
gatgatcgcc ctgtggaccg aactcggccg ccgggtggat cgcatcgagc agatcggccc   4080
gaagaagcag cacatcaaca acctcatccg cagcctcgat tcgctgcccg tgcggatcta   4140
cccgaagtga tgccgatgcc caagatcacc ttctcccaat cggacgggtc gtcgatcacc   4200
gtcgatgcgt cgctggacca gagcgtcatg caggccgccg tcgccgcagg tatcgacggc   4260
atcctcgccg agtgcggtgg caacgccacg tgttccacct gccacgtgta cgtcgaaccc   4320
gagcaactcg ggctcctcgc ggacctgagc gccgaagaag acgacatgct cgactgcgcc   4380
gaggccgaac gtcggagcaa cagccggctg gcgtgtcagc tgccggtcac caccgacctc   4440
gacgggctcc ggctggaggt ccccgacgcg ttctgaacgc gtccggcacc agccgcctcc   4500
caccacacaa gaactgttcg cagtaccaat caccaaggag tgcaccatgt atcagatcgt   4560
ggcctgctac ggccagccca ccgacaccga ggcgttcgac acctactacg acagcaccca   4620
cgtgccgctg gcgaacaagc tccccggcct cgtcgactac atcacggtca agtgcgtctc   4680
ggcactgccc ggggaagggg tcccgtacta catggtcgcg accctgacct tcaactcgga   4740
gcgcgacgtc aaggccgcgc ttgagtcgcc ggagatggac gccgcgaagg ccgacgtcgc   4800
caacttcgcc accggcggcc tggccctcta catcggggat gaggtcgacc ggacctagtt   4860
cgaccggcca ccgtgtgcgc gacgatggga aacatgctgc accacagcgt gtttcccatc   4920
gttcgcaccg tcacgaccga gtgcgcacca ccccgaacat cacgatcccc gactgtcacg   4980
atcccccgcc ccaggagccg caaccatgtc cgccttgatg aagacgttca ccatgctcga   5040
ggtctccgtc ctcgttgacg gtgaccgaca ggtgcgggtc ggcatcgtcg tcgggtaccg   5100
cggtggcgtc gctcatcgct gcgttcctcc ttcgctcagg actcgtttca ccacgagcga   5160
```

-continued

```
gctcgtcggt gaaatcgtta ccagtgtgac gggctggccg cgtgttgtgg gaacggatgt   5220
cgccagcgtt gcgctgatgg cgatcatcac cgtgcggggc tgggtgccgg tgaagtcgga   5280
gtagatcaga ttggcggggg aaatggcggt gggtgccacg cgttgtccga tggtgatctg   5340
ctcggcaatg gtcgccggca tggtgattcc tacgcggtga aagacgtact ggactgcctg   5400
ggtttggccg attcggccgt tctgggggcc gtcgacggtg cctgccgtgt cgtcagcggt   5460
gatgcggtcg gatacgagca tggtggcgta tcgggcgacg gtggctgcgg tgctggtggt   5520
gagggtggag gtcagcgggg gttgttggta gggggcggtg gacagtttcg tgacgcattc   5580
gcggattcgg gtcggcaggg tcgaggggat gtcggtgagg gaagcgtagg ggttggtgct   5640
ggggagggtg gcggtctcgg tcggctgggc ggtggtgtgg agggtggtgg tcgagggggt   5700
cgtcgggtct tgcgttgccg gtgcggtggt ggtgtcggag gaggggcaga ggggtcgagg   5760
ccgagcacgc tgtcgcattg atagaggaag tcttgctggg tttggctcat gccgccgcct   5820
ccgacgaagg cggtcatcat cgcgcaggat gctgcggtga tgagtatggc tgcggccgtg   5880
aggattccgg cgacggtttt catggtcgag ctcacctagg agtcctgtct gacgtggtgg   5940
tcgggcgcta ggcgggggcg gggttgttgc gcctggctct cggctgctga ggtcgtgtcc   6000
cggcggcgct gccaggggga ggtgaccggc ggcggggcgg tgccgggggc ggctggggtg   6060
accatgacgt gggtggtttg tgctgtgggg gctgccgttg gcggcgtcgt cgatggcggt   6120
gtcgtcgatg agggcgtgga ggtggtcggt gtcggctcgc gagggggtgt ttcgtcgtcg   6180
tgggtggtgg tgggcatggc gtgggtggtg gtggtgctgg gtgtgcgcgg tgcggggagt   6240
ggttctcgtc ggccggcggt aggcggaggg tcgtcgtatc cggtgccggt ggggagcggt   6300
aggtgaggtt gtggcgcggg attgcggttg cggtgtcggg gagtgcccgg tgaggcgagg   6360
tcaggggtgg gcgcggtggg gtcgcgcggc gcgtcggggg cagaggggtg gggtagctcg   6420
acggtgggtg tgcgaggcgc ggtggcacgg tgtgcggctt tgcttgccgc gtgggctgcg   6480
gcttgtttgc cggcggtgcg gacggcggcg ctggccgcgg ccgaggttcc gccggtggca   6540
gctgcggcgg cggcctgcgc ggcgacgggg gccagggacc ggaccactcc gcgtttgcgg   6600
tcggtgggct tggctggagg ggtggtggtg ggttggccgg gatcggcggg cagtgcgtgg   6660
gtttcggtga gggcgcggat cttcttgact gcggagccct gcgagatacc ggtgacggtc   6720
tgcgcggcgc tgagggcgtg ggtgagcgcg ctgggcccga cgggtgtgct ggcggtgggt   6780
gagccgccca tggcggagat attggcggag atcttctttg ccgcctgttc tcgggtgctg   6840
cgggtacgcc agagcaggac gatcgcgacg atcatggcga tgccggcgac ggtgatgccg   6900
gcggctccgc tgaggttgtt agagctcagg agtgatcgca ggatgagtga ccatccgccg   6960
aggaagacga cgtacaccgt catcgccagc gcgcacagga tcatgtcggc gaagctgttc   7020
cagagcgcgg tttgtccggt gccgggaatg aagccggtga tggcgaatcc gacgatcacc   7080
ttgaatcctg cccagatggc ctggaaggcg gtgaggatga tgcggaagcc gagatagcag   7140
gcgaaggcca agagcaggaa ggagaacagg atcagcgcta cgccggtgcc gatctgggat   7200
ccgctggggt tgtccgcgac gtgtttcatg gcgtgtgagg cgtcggcgcc gcagtcttct   7260
atggcgtctt tgacctggtc ttcttcgccg ctgcgttgcc cggagctcca ggccgctctg   7320
catgctgggg attgctcgtc gacgacggcg ccgaagttcc actgttgcag ggttggcgg    7380
atgaatgtgg tggtcagctg tcgttggagc tgctcgatca tggcggcgcc gtcactggtg   7440
ggttggccgg acatcgatgt ggagatggcg attccggtgt ctcggccctg ggagagcagt   7500
```

-continued

```
ccgtcggaac cgatgattct gccgacgggg ttgccgagga cggtgccgcc gaggacggcg   7560

acgacgagga tcatgcacaa ctgtgccacg gccttggagg tgtggccgcg gaggaagtac   7620

caggccaccg ggacggagcc gacggccacg gccgcgccga cgattgcggg ggtcgagatc   7680

gtctgggtga ggctgttgga gatcgcgacg atcgaggtgg agaacagatt caaccagttg   7740

aaagacatgg cccagcacac gaaccagacg ccgaaggaca cgaccatgag ccagattccg   7800

aactccgact gcaggattga ggacagtggc aggttggtgg ggtgccagag cgatccgtgg   7860

tcggtggaga acatgtaggc cgagacccct actccgtcct cgtcttgcag atccatccag   7920

ccgatcgctg cggcggcgct gacttgggtg gctgcggcgg cctgggggc cagccaggtg   7980

gagaggacga cccaggtgtg gatggctatc tgtgaccaca cgatccagcg gcgcagtctg   8040

gtcttgttga tccaggaagt tgtgtgggcc agcaggatcg ctgggtcgag acgagggagg   8100

atctggtcgg cggtcacgcc gtggtgccat gcgtgtgtcc aggtgagggt ggtcatacgg   8160

tggcctgacg tccgggggtg gtgccggcgg cgcggcggcg gtcgggggag gacaggccga   8220

ggaccttggc tcggcccatg cggccgaggg catcgcgcat gaagcactcg ccgcggcgat   8280

tgggggaac ggaatcgaag tcttcgctgc gcatgggtgc agtttcggtt tggagctgct   8340

tgacgaggtg cgcgttctcg tcggtgtcga tgtcgagcca gcgcagtgac tcttcggcca   8400

gagcacggtc gcgctgacgg aagacgaagc gggtgggcac gagtttgagg ctgtcgttgt   8460

cccagtcgct gccgggtgcg tgggaggcca ggctcatgag ggcgttgttc ttgcgtccgt   8520

cgcgggcgaa ctcggtggtg atgcggcggc cgaccggggc gacggtgaag tggtaagcct   8580

catcgccgtt gaatgcgccg aggcgatcgg agtggaacag ggagaagcgg gcggtgaccc   8640

cgatcagcgc gtagatgcag gtgccgagtt tggcgcgggc agagatctgc cggtagaggt   8700

gcgggttcag gagttcgtcg cgatcggcga gggcaaggcg gtgggtgcgg atcactgttg   8760

ccggac                                                              8766


<210> SEQ ID NO 4
<211> LENGTH: 5576
<212> TYPE: DNA
<213> ORGANISM: Rhodococcus ruber

<400> SEQUENCE: 4

tgggggtcga ggagcaaacc cgcccaatcc ggcgctaagg atttaccgca catagtgtca     60

tactatgtgc gatcggataa cggtcgatg cgccccagtc gggcgactcg agaacctgtg    120

cgcggtagta gttcgaggtt gatgacatgg ggcgggttca caggttgtcg acgtcggcga    180

gtgatgtgcg gctggccgat gcagtacaga tctacttggc gacgattatg gtgtcgaaca    240

cccgcgcaac ctacgcggcg gcgctgaatc ggttggtggt cgacttcggg gcggatacga    300

atgtggcgtt gctgggctcg gagccggatc gggtcagtgg ctggttcacc ttcgtgtggg    360

gtggcaagtc ggcgaagacg tttaacatcc gattgactgc gctggggtcg gcgtgcgcat    420

attggcgcga tcagcagtgg ttggccggcg atccgttagt gcggttgcga acgcggcccg    480

caccgccgga caccagtagg gcgttgagca aggatcgggt caccgagatc ttgggatcgg    540

atgcggccca gagggaacag gtgttatggc acatgctcta cgaatccgcg gcgcgtgccg    600

aggaggtgtt gatgctggat gtgcccgacc tcgacacagc gaaccgctgc gcggaggtga    660

cacgcaaggg cggggcacgc gaactctgaa ccaccctgga tctgatggag acctggttca    720

agccacgtcg cggtcggagg tggctgtcga gcgttgttga cggtactcgt tttcgtagtc    780

gatgggcggt tggtatccga tcgaggagtg caggcggctg gtgttgaacc aatgcaccca    840
```

-continued ggaagccgtc tcgcgctcga cctcgctgcg cccgctccac gacttctgcc ggtcgatcag 900
ctcggtcttg tacaacccga tcgtcgattc catcaacgca ttgtcgagcg cgtcgccgac 960
gctgccgatc gatccagcga tgccggattc gatcaacgcc tcggtgaacg ccagagacgt 1020
atactgggaa cccgcgtccg agtgatggac caaacccgtt gcagtgaacg cgaagtcgga 1080
ccggcgacgt gtgaacaatg cttgctcgag tacacccgac accagcggcg tcgccttcgt 1140
cgtcatgacc ctccacccga gaatccggcg ggagaacaca tcgaccacga acgaggtgta 1200
cacgaaacca accaacgtcc agcaataagt aaaatcggca acccaccact ggtccggttg 1260
agtcggcgcg ccccactgcc gggcaatcag atccggatgt cgaggggcac gatcatcgcg 1320
ttcggtggtc accgtacgcc ggcgtccgcg gacaacaccc tctgctccgc agatcgtcat 1380
caaccgagcg acctgatcgc ggccgatctc gtgaccagcg cgtttcattg catgccagat 1440
tttcttggct ccgtagaggc gtctgtttgc cacgaagaac ccgtgaacgg tgttcgtggc 1500
gtacgcctct tccagtgccg ctgcggagac ggtgccgcgt ttcttggcgg cgtagtaggt 1560
ggacggggcg atcttgatgc cgtgctcttt gagtacggtg cagatcgggt cgaccccgaa 1620
aaggtggcgg tattcgtcga tgtactcgac gatcaccgaa gtcggcggtc gacctccgcc 1680
gctgcgaaaa acgctgacgc tgtcttgaga atctcgttgg ctcttcgcaa ttcggagttc 1740
tcacgccgta gcgccttcaa ctcctcgtcg cggtcaactc ctgcgacggg cccgtgtgcc 1800
tcggtggccg gatcgttctt ctcgatccag tttcggatcg tcgccgggtt gatatcgagc 1860
agagccccga cgtgcttacg ggccgttact ttcggctcgc cgtactcctt gagccggtcg 1920
cgatacatcc gaactgcccg ctcccgcgtc tcagcatcga acttccttgg tgcacccata 1980
tctgcattct cctggtgaga tcacagtctc caccagcccc agggtggttc actcgtcgcg 2040
tggcagagcg ctaccgcgcg cctgttgccg cggatgctgg ccgaccgcac gagcggtcca 2100
ctgttcctca ccgcccgaaa agcccgatcg tccgtggctg cacgcgatgt cgactcgtcg 2160
acggggcggg cacggctgtc ttatcggcgc gcggccgaga tgttcgaagg ccacaccgtc 2220
cactacgacg acggcccgta cacgctgcac caactacggc attcacggct gacgcatgcg 2280
gccgaggatg gcgcgtcgat gccggtgttg atgacgctgt cgggtcagat gtcggtgcga 2340
ggccttgtcg agtacgcaag aatctccgac gatgggctac ggcgctttca ggccgagagc 2400
gatccggcgg cgcgtcggcc agggcggtga tcggcgcagt gagtcgcacc gtcaatcgct 2460
ctcgtgggca tcgggatcgc gcagcggccg gtgtgttcca ccgaggtctg gtaagtggaa 2520
ggcgtagtgg ccgtcgatac cgatgtgggt gcggataaac gccgatagtc gctgcgcgtc 2580
ggcgtcgagc accggatagc cctgcgcgcg tagctgttcc agagcgcggt tggtgtataa 2640
cgtattccac agaactgtgc agttgagcac caaccccagt gcggagagtt gatcttccat 2700
gccttcgtag taggtacggg tcatctcccc cttctttccg tggtagatcc ggcgcgccag 2760
gtcgtgacgc ccttctccga gattggcctg aatcttgcct tccctgcggt acggttcgtc 2820
gtcggccagg cgcaggatgt gcagggtttt gaagatccgc ccataatggg cgatcgcttg 2880
acccaagggg gtaggtttcc cgtcccggga gatcatccgg gtgacgtcgt gagcggagac 2940
ctcacactcg ttgatcgaca ctgcaactcg gcacatgtcc tcccagtgcg cggcgatctt 3000
gtcggtgtcg atgtgacccc gagcggcctg gttgagtggc ccgtagtccg cggaccggtc 3060
gaaccgccat aaccgctgat cgggcagatt cgctaactgc ggccggtatc tcttgccgat 3120
caggtgcatc agaccgaaca cgatgtcgct gtaggagccg gtgtcggtga cgatctcgtc 3180

-continued gggagctttt ccgccctgct gaagctgcac cacatcgatg aagttcaggg agtcgcgggg 3240
cgtcccggac acgaccttgg ccgccagccc ggcggactgg tcgttgagca tgttcaacca 3300
ggtgatcccg cgcttacggc cgaagtactt cgggttcggt ctcgcgtgga tggtgcggac 3360
cggaaccacg aaccgcatac cgtccaccga ggcgagtagc ccaccacccc acagctgcgc 3420
caattcgatc tcggactggg cctctaccag ctcgacgttg gccgcagtca acgtctccac 3480
gcgaacgtag ttctggtcga catggtgcag acggtcacgg gtcagcgcgt gaacaccagg 3540
gctggtcacc ggtgtgaaac ccacgttcat cgcgtgcgcg cacagtacgg ccgcgaccga 3600
caatccgaga tcggcgacgc gggcaccgtt gccggaggcg tgggtgaacg actcggtgaa 3660
ccggggcacc caggacatga cttccaagac cagctcgggc aggtcgacct cgggcaacat 3720
tgtctggacc cggcgacgta gatcgaccag cgacggcggg tccggttctg ctttcagcga 3780
ggcgaggtgg agacgcccgt cctcgccgac gctcgccgga ccgtcactgt ccaacctcgc 3840
ggcgacctca cggtaggcag tgtccatcgt ggcggcatgc tcggcgagca gcggtgccgg 3900
atcgcccggt aggttcaacg cgttcatccc ggcctcgcgg gagcgatccc atgcttgccc 3960
gaccagcagc tgggctcgag ggtcacgcca tcgcgtcgag tgcggggcaa agatgttgcg 4020
atacttgaga tgtcgatgga actgctccag taggcacaag gtgtaggcgg cgcggtcgac 4080
cgtctccggt ggccgaggat cgcgatagac cagcctcttc cagccgccac cgatgagatc 4140
atggtcgatc tggcgggcat cgagccagct cgcgggtagt ttcgacttcg tcgacatcag 4200
ctcaccgagg gtcttcatcg ctgccagtac cgccgcaccg tccgcggtcg ctccgaacgt 4260
cacggtgttc atcagccggg gcaggaacac ccggaccgtg gccaagcgtc ccgccaactc 4320
ttccaggcgc tgcccatcga gttccgcgtc atcgaccggc accaactcgt cgatcaccgc 4380
taccgacgcg cgcagctcac ttttggtcgc gatgttctcg atcagatccc acagcatgtt 4440
gacgctgagg ttcggctcga cctcactcat ctccaacagc atcttgaccg ctgccgagag 4500
cttgcctgca tgacgtgaga cgcgtgggta tcggcgcagc ttctcatcgc gtgactcacg 4560
ttcggccttc gacatcaggt tcgtgaccat caaaagatcg aacaactcga gcacgtcatc 4620
agttgccctg ttcgacagca ctttcaccgt ggcgaccagc accgccaggc gattgcggcg 4680
gggctcgatg cgccgcaatg taggggcctt actcgatagc ccgtaggtgg ccagtgcgat 4740
cactcgacgc tgcggaacca tcgacacatc cagtgattgc ccgcccagcc cgatgaggtc 4800
ggtcaaccgt tccagggcgt cgagcatacc cttcgagctg gtccggaaca cgccccggcg 4860
aagccgctcc agttcgctga cacgacgttt gccctcgggt acatcgagca acgccagtag 4920
cgccgaagca gaaccagcag tgagttgatc ggtcagctga ctccacaacc gctgatcagc 4980
ggcctgtcgc ccgtcggtca ccacacgtac cagagtgcgg ggaccgggaa gcagcgcctg 5040
atgttcacgt aaccagtcga ccgcactggc gaatatcgct ttcggcccat cgccggtgac 5100
ccacgcctga tcggcgaccc acgccgccaa ctccgcctcg acctcagcat aggaactcaa 5160
gccgtactcg cgctggatct cccaagcgtg ttcgagtttg gttttcttcc gctcggtgta 5220
ctgcttcaca cacgaggagt cctcgatacc caactgctcg gcgagatagt cgaccagctc 5280
caggggcgca tcgagcggat cagccaaaaa cattccgagt tggcggactg tcacgatctg 5340
aagggcgaac cccaaccggt tgtagtcacg acgccgacca gcgatcagct tccggtcctc 5400
gtcatcgagg tagaaaaacc gttccagctc aacacgggac aacgccccga accggccgta 5460
gccgccctca tcggtcatgc cgacatgaaa tcacctgtag gtccacgccg ccgacgtcac 5520
cgctcgatgt tcatcgctta gcgccggatt gggcgggttt tgctcctcga cccccg 5576

-continued

<210> SEQ ID NO 5
<211> LENGTH: 1239
<212> TYPE: DNA
<213> ORGANISM: Rhodococcus ruber
<220> FEATURE:
<221> NAME/KEY: CDS
<222> LOCATION: (1)..(1236)

<400> SEQUENCE: 5

```
atg atc atc atc ggc gcc ggg cag ggc ggc ctg cag gca gcg atg tcg       48
Met Ile Ile Ile Gly Ala Gly Gln Gly Gly Leu Gln Ala Ala Met Ser
  1               5                  10                  15

ctg cgc gat cac ggc tat acg ggc cgc ctg acg atc gtc ggc gac gaa       96
Leu Arg Asp His Gly Tyr Thr Gly Arg Leu Thr Ile Val Gly Asp Glu
             20                  25                  30

ccg ggc ctg ccg tat cag cgt cct ccg ctg tcg aag gcg tat ctc atc      144
Pro Gly Leu Pro Tyr Gln Arg Pro Pro Leu Ser Lys Ala Tyr Leu Ile
         35                  40                  45

aac gac gac gcc atg tcg gag gaa ctc ctg ctg ctc cgg ccg cac tcg      192
Asn Asp Asp Ala Met Ser Glu Glu Leu Leu Leu Leu Arg Pro His Ser
     50                  55                  60

gtg ttc gag cga ctc gac atc gac ctc atc acc ggt gac ggc gtc acc      240
Val Phe Glu Arg Leu Asp Ile Asp Leu Ile Thr Gly Asp Gly Val Thr
 65                  70                  75                  80

cgc atc gac cgg gtc cgc agc acc gtg tcg ctg agt tcg ggt cgc gaa      288
Arg Ile Asp Arg Val Arg Ser Thr Val Ser Leu Ser Ser Gly Arg Glu
                 85                  90                  95

ctg gcc ttc gac cac ctg atc ctg gcc acc ggc gcc cgg ccg cgg gag      336
Leu Ala Phe Asp His Leu Ile Leu Ala Thr Gly Ala Arg Pro Arg Glu
            100                 105                 110

ctg agc gtg ccg ggc gcc gac ctc gcg gga gtg gag gca ctg cgt acg      384
Leu Ser Val Pro Gly Ala Asp Leu Ala Gly Val Glu Ala Leu Arg Thr
        115                 120                 125

tgc gac gac gcg aag gcg atc cgc gcg ggg ctc acc ggc ccg gca cgg      432
Cys Asp Asp Ala Lys Ala Ile Arg Ala Gly Leu Thr Gly Pro Ala Arg
    130                 135                 140

gtc gtg gtg atc ggc ggc ggc ttt gtc ggg acc gag gtg gcc gcc gcg      480
Val Val Val Ile Gly Gly Gly Phe Val Gly Thr Glu Val Ala Ala Ala
145                 150                 155                 160

gcg acc aag cga ggc cac tcc gtg acg atc gtc gac atg gag gcc cgt      528
Ala Thr Lys Arg Gly His Ser Val Thr Ile Val Asp Met Glu Ala Arg
                165                 170                 175

ctc ctc aat cgg gct gtg tcc ccg gag atc tcc gca ctc gtc acg gcg      576
Leu Leu Asn Arg Ala Val Ser Pro Glu Ile Ser Ala Leu Val Thr Ala
            180                 185                 190

gcg cat cgc cgc agg gga acc gcg gtc gtc ctg aac gcc ggc gtc agc      624
Ala His Arg Arg Arg Gly Thr Ala Val Val Leu Asn Ala Gly Val Ser
        195                 200                 205

cgg ctg tgc ggc tcc gac ggc acc gtc gaa gcc gtg gaa ctc act gac      672
Arg Leu Cys Gly Ser Asp Gly Thr Val Glu Ala Val Glu Leu Thr Asp
    210                 215                 220

ggg caa cgg att ccg gcc gac ttc gta gtt gtc ggc atc ggc gtc gtg      720
Gly Gln Arg Ile Pro Ala Asp Phe Val Val Val Gly Ile Gly Val Val
225                 230                 235                 240

ccc aac acg gag atc gcc cac gac gcc ggc ctc gcc gtc gac aac ggc      768
Pro Asn Thr Glu Ile Ala His Asp Ala Gly Leu Ala Val Asp Asn Gly
                245                 250                 255

att ctc gtc gat gac cgg ttg cgc acc aac gac cac cgg atc agt gcg      816
Ile Leu Val Asp Asp Arg Leu Arg Thr Asn Asp His Arg Ile Ser Ala
            260                 265                 270
```

-continued

```
atc ggc gac tgc gcg cga ttc ccg tgc gca cac gcc gac ggc cag atg      864
Ile Gly Asp Cys Ala Arg Phe Pro Cys Ala His Ala Asp Gly Gln Met
        275                 280                 285

ctg cgc ctc gaa tcg gtg cag aac gcc gtc gac cac gca cga cac gtc      912
Leu Arg Leu Glu Ser Val Gln Asn Ala Val Asp His Ala Arg His Val
    290                 295                 300

gcc gcc cga ctc atg ggc gac gca gga ccc tac gac gcc gtg ccg tgg      960
Ala Ala Arg Leu Met Gly Asp Ala Gly Pro Tyr Asp Ala Val Pro Trp
305                 310                 315                 320

ttc tgg acc gac cag tgc gga ctg aag atc cag atc gcc gga atc ggc     1008
Phe Trp Thr Asp Gln Cys Gly Leu Lys Ile Gln Ile Ala Gly Ile Gly
                325                 330                 335

gcg cag ggc gcc gag tcg gtg gtg atc ggc gac gag gca gca gaa cga     1056
Ala Gln Gly Ala Glu Ser Val Val Ile Gly Asp Glu Ala Ala Glu Arg
            340                 345                 350

tgt tcg gtg ctg cgg ttc cgc tcc ggc gaa ctg tcc tgt gtg gag tcg     1104
Cys Ser Val Leu Arg Phe Arg Ser Gly Glu Leu Ser Cys Val Glu Ser
        355                 360                 365

gtc aac agc agc ggc gag cac atg gcc gca cgc aag atc ctg cgc ggt     1152
Val Asn Ser Ser Gly Glu His Met Ala Ala Arg Lys Ile Leu Arg Gly
    370                 375                 380

gga ccg cgc ccg gtg gcg ccc gtc gac ggg tca ccc gct gcc ttc gac     1200
Gly Pro Arg Pro Val Ala Pro Val Asp Gly Ser Pro Ala Ala Phe Asp
385                 390                 395                 400

ctc aaa cac atc gcc cgg gag gtc gcc acg gct cgc tga                 1239
Leu Lys His Ile Ala Arg Glu Val Ala Thr Ala Arg
                405                 410


<210> SEQ ID NO 6
<211> LENGTH: 412
<212> TYPE: PRT
<213> ORGANISM: Rhodococcus ruber

<400> SEQUENCE: 6

Met Ile Ile Ile Gly Ala Gly Gln Gly Gly Leu Gln Ala Ala Met Ser
  1               5                  10                  15

Leu Arg Asp His Gly Tyr Thr Gly Arg Leu Thr Ile Val Gly Asp Glu
             20                  25                  30

Pro Gly Leu Pro Tyr Gln Arg Pro Pro Leu Ser Lys Ala Tyr Leu Ile
         35                  40                  45

Asn Asp Asp Ala Met Ser Glu Glu Leu Leu Leu Leu Arg Pro His Ser
     50                  55                  60

Val Phe Glu Arg Leu Asp Ile Asp Leu Ile Thr Gly Asp Gly Val Thr
 65                  70                  75                  80

Arg Ile Asp Arg Val Arg Ser Thr Val Ser Leu Ser Ser Gly Arg Glu
                 85                  90                  95

Leu Ala Phe Asp His Leu Ile Leu Ala Thr Gly Ala Arg Pro Arg Glu
            100                 105                 110

Leu Ser Val Pro Gly Ala Asp Leu Ala Gly Val Glu Ala Leu Arg Thr
        115                 120                 125

Cys Asp Asp Ala Lys Ala Ile Arg Ala Gly Leu Thr Gly Pro Ala Arg
    130                 135                 140

Val Val Val Ile Gly Gly Gly Phe Val Gly Thr Glu Val Ala Ala Ala
145                 150                 155                 160

Ala Thr Lys Arg Gly His Ser Val Thr Ile Val Asp Met Glu Ala Arg
                165                 170                 175

Leu Leu Asn Arg Ala Val Ser Pro Glu Ile Ser Ala Leu Val Thr Ala
```

-continued

```
            180                 185                 190

Ala His Arg Arg Arg Gly Thr Ala Val Val Leu Asn Ala Gly Val Ser
        195                 200                 205

Arg Leu Cys Gly Ser Asp Gly Thr Val Glu Ala Val Glu Leu Thr Asp
    210                 215                 220

Gly Gln Arg Ile Pro Ala Asp Phe Val Val Val Gly Ile Gly Val Val
225                 230                 235                 240

Pro Asn Thr Glu Ile Ala His Asp Ala Gly Leu Ala Val Asp Asn Gly
                245                 250                 255

Ile Leu Val Asp Asp Arg Leu Arg Thr Asn Asp His Arg Ile Ser Ala
            260                 265                 270

Ile Gly Asp Cys Ala Arg Phe Pro Cys Ala His Ala Asp Gly Gln Met
        275                 280                 285

Leu Arg Leu Glu Ser Val Gln Asn Ala Val Asp His Ala Arg His Val
    290                 295                 300

Ala Ala Arg Leu Met Gly Asp Ala Gly Pro Tyr Asp Ala Val Pro Trp
305                 310                 315                 320

Phe Trp Thr Asp Gln Cys Gly Leu Lys Ile Gln Ile Ala Gly Ile Gly
                325                 330                 335

Ala Gln Gly Ala Glu Ser Val Val Ile Gly Asp Glu Ala Ala Glu Arg
            340                 345                 350

Cys Ser Val Leu Arg Phe Arg Ser Gly Glu Leu Ser Cys Val Glu Ser
        355                 360                 365

Val Asn Ser Ser Gly Glu His Met Ala Ala Arg Lys Ile Leu Arg Gly
    370                 375                 380

Gly Pro Arg Pro Val Ala Pro Val Asp Gly Ser Pro Ala Ala Phe Asp
385                 390                 395                 400

Leu Lys His Ile Ala Arg Glu Val Ala Thr Ala Arg
                405                 410


<210> SEQ ID NO 7
<211> LENGTH: 1203
<212> TYPE: DNA
<213> ORGANISM: Rhodococcus ruber
<220> FEATURE:
<221> NAME/KEY: CDS
<222> LOCATION: (1)..(1200)

<400> SEQUENCE: 7

atg aca ctg tca ctg gcc acg gcc cag gaa cgc tat gcc acc gat gcg       48
Met Thr Leu Ser Leu Ala Thr Ala Gln Glu Arg Tyr Ala Thr Asp Ala
  1               5                  10                  15

gac gtc ttc gca cac gac acc ctg gtc gat ccc tac gac acg tat cgg       96
Asp Val Phe Ala His Asp Thr Leu Val Asp Pro Tyr Asp Thr Tyr Arg
            20                  25                  30

tcg ctg cgc gac atc ggc cgt gtg tcg tac atg acc cgg tac gac acg      144
Ser Leu Arg Asp Ile Gly Arg Val Ser Tyr Met Thr Arg Tyr Asp Thr
        35                  40                  45

tgg gcg ctc acc cgc tac gac gag gtc cgt cac gcg ctc ggc gac tgg      192
Trp Ala Leu Thr Arg Tyr Asp Glu Val Arg His Ala Leu Gly Asp Trp
     50                  55                  60

cag acg ttc agt tcg gcg cag gga atc gga atg agc acg gca ctc aac      240
Gln Thr Phe Ser Ser Ala Gln Gly Ile Gly Met Ser Thr Ala Leu Asn
 65                  70                  75                  80

gag gcg tgg aag gac ttc gcg ccg tgc aag gac ggc gcc gac cac ctg      288
Glu Ala Trp Lys Asp Phe Ala Pro Cys Lys Asp Gly Ala Asp His Leu
                 85                  90                  95
```

-continued

```
ccc atg cgg aag ttg atg atg cag gac ctc ggc ccc aaa gcc gcc gcg      336
Pro Met Arg Lys Leu Met Met Gln Asp Leu Gly Pro Lys Ala Ala Ala
            100                 105                 110

gcc tac aag gag aag atc cag cag gcc gcc gtg acg ctc gtc gag gag      384
Ala Tyr Lys Glu Lys Ile Gln Gln Ala Ala Val Thr Leu Val Glu Glu
        115                 120                 125

ttg ctc gat cgc cgc gag ttc gac gcg gtg ctc gac ttc gcc cag atg      432
Leu Leu Asp Arg Arg Glu Phe Asp Ala Val Leu Asp Phe Ala Gln Met
    130                 135                 140

atg ccg atg cgg gtg ttc atg gag gtg ctc ggt gtc gag ccc gac atc      480
Met Pro Met Arg Val Phe Met Glu Val Leu Gly Val Glu Pro Asp Ile
145                 150                 155                 160

gaa cag cgc cgc acg atg ctg cac tgg ggg acc gac acc tac aac tgc      528
Glu Gln Arg Arg Thr Met Leu His Trp Gly Thr Asp Thr Tyr Asn Cys
                165                 170                 175

gcg gcg ccg gac ggc ctc tac gac gac acc ctg ccc agc atg gac aag      576
Ala Ala Pro Asp Gly Leu Tyr Asp Asp Thr Leu Pro Ser Met Asp Lys
            180                 185                 190

ctc tac agc tgg gcg ctg gag aac atc act ccg gag acc gca cgc gag      624
Leu Tyr Ser Trp Ala Leu Glu Asn Ile Thr Pro Glu Thr Ala Arg Glu
        195                 200                 205

ggc agc gtc gcc gcg tcg acg tgg gag tcg gtg gaa cgc ggc gac atc      672
Gly Ser Val Ala Ala Ser Thr Trp Glu Ser Val Glu Arg Gly Asp Ile
    210                 215                 220

acc gac gtg cag gcg gtc gcg acc ctg gcg gct tac gtc acc gcc gga      720
Thr Asp Val Gln Ala Val Ala Thr Leu Ala Ala Tyr Val Thr Ala Gly
225                 230                 235                 240

ctc gac acc acc gcc ggt acc ctc ggc aac acg atc gcg cag ttc gcg      768
Leu Asp Thr Thr Ala Gly Thr Leu Gly Asn Thr Ile Ala Gln Phe Ala
                245                 250                 255

gcg aac ccg gac cag tgg gcc atc gtc cgc gac gac ccc aag acc atc      816
Ala Asn Pro Asp Gln Trp Ala Ile Val Arg Asp Asp Pro Lys Thr Ile
            260                 265                 270

ccg ggc gcg atc ctc gag ggc atc cgg ttc gac agc gtg gcg cag tgg      864
Pro Gly Ala Ile Leu Glu Gly Ile Arg Phe Asp Ser Val Ala Gln Trp
        275                 280                 285

ttc acc cgc gtg acc acc cgc gac gtc gag tac gac gac atc gtc atc      912
Phe Thr Arg Val Thr Thr Arg Asp Val Glu Tyr Asp Asp Ile Val Ile
    290                 295                 300

ccc gcg ggg tcg cgg acg tat cac tcc tac gcg gcg gca aac cgg gac      960
Pro Ala Gly Ser Arg Thr Tyr His Ser Tyr Ala Ala Ala Asn Arg Asp
305                 310                 315                 320

gag cgg cac tac cgc gac ccc gac tcc ttc gac gtg ctg cgc aac ccc     1008
Glu Arg His Tyr Arg Asp Pro Asp Ser Phe Asp Val Leu Arg Asn Pro
                325                 330                 335

acc gac cac gtg ggg ttc ggg tac ggc ccg cac atg tgc gtc gga aag     1056
Thr Asp His Val Gly Phe Gly Tyr Gly Pro His Met Cys Val Gly Lys
            340                 345                 350

tcg gtg tcc aac acc gag atg atc gcc ctg tgg acc gaa ctc ggc cgc     1104
Ser Val Ser Asn Thr Glu Met Ile Ala Leu Trp Thr Glu Leu Gly Arg
        355                 360                 365

cgg gtg gat cgc atc gag cag atc ggc ccg aag aag cag cac atc aac     1152
Arg Val Asp Arg Ile Glu Gln Ile Gly Pro Lys Lys Gln His Ile Asn
    370                 375                 380

aac ctc atc cgc agc ctc gat tcg ctg ccc gtg cgg atc tac ccg aag     1200
Asn Leu Ile Arg Ser Leu Asp Ser Leu Pro Val Arg Ile Tyr Pro Lys
385                 390                 395                 400

tga                                                                 1203
```

-continued

<210> SEQ ID NO 8
<211> LENGTH: 400
<212> TYPE: PRT
<213> ORGANISM: Rhodococcus ruber

<400> SEQUENCE: 8

```
Met Thr Leu Ser Leu Ala Thr Ala Gln Glu Arg Tyr Ala Thr Asp Ala
  1               5                  10                  15

Asp Val Phe Ala His Asp Thr Leu Val Asp Pro Tyr Asp Thr Tyr Arg
             20                  25                  30

Ser Leu Arg Asp Ile Gly Arg Val Ser Tyr Met Thr Arg Tyr Asp Thr
         35                  40                  45

Trp Ala Leu Thr Arg Tyr Asp Glu Val Arg His Ala Leu Gly Asp Trp
     50                  55                  60

Gln Thr Phe Ser Ser Ala Gln Gly Ile Gly Met Ser Thr Ala Leu Asn
 65                  70                  75                  80

Glu Ala Trp Lys Asp Phe Ala Pro Cys Lys Asp Gly Ala Asp His Leu
                 85                  90                  95

Pro Met Arg Lys Leu Met Met Gln Asp Leu Gly Pro Lys Ala Ala Ala
            100                 105                 110

Ala Tyr Lys Glu Lys Ile Gln Gln Ala Ala Val Thr Leu Val Glu Glu
        115                 120                 125

Leu Leu Asp Arg Arg Glu Phe Asp Ala Val Leu Asp Phe Ala Gln Met
    130                 135                 140

Met Pro Met Arg Val Phe Met Glu Val Leu Gly Val Glu Pro Asp Ile
145                 150                 155                 160

Glu Gln Arg Arg Thr Met Leu His Trp Gly Thr Asp Thr Tyr Asn Cys
                165                 170                 175

Ala Ala Pro Asp Gly Leu Tyr Asp Asp Thr Leu Pro Ser Met Asp Lys
            180                 185                 190

Leu Tyr Ser Trp Ala Leu Glu Asn Ile Thr Pro Glu Thr Ala Arg Glu
        195                 200                 205

Gly Ser Val Ala Ala Ser Thr Trp Glu Ser Val Glu Arg Gly Asp Ile
    210                 215                 220

Thr Asp Val Gln Ala Val Ala Thr Leu Ala Ala Tyr Val Thr Ala Gly
225                 230                 235                 240

Leu Asp Thr Thr Ala Gly Thr Leu Gly Asn Thr Ile Ala Gln Phe Ala
                245                 250                 255

Ala Asn Pro Asp Gln Trp Ala Ile Val Arg Asp Asp Pro Lys Thr Ile
            260                 265                 270

Pro Gly Ala Ile Leu Glu Gly Ile Arg Phe Asp Ser Val Ala Gln Trp
        275                 280                 285

Phe Thr Arg Val Thr Thr Arg Asp Val Glu Tyr Asp Asp Ile Val Ile
    290                 295                 300

Pro Ala Gly Ser Arg Thr Tyr His Ser Tyr Ala Ala Ala Asn Arg Asp
305                 310                 315                 320

Glu Arg His Tyr Arg Asp Pro Asp Ser Phe Asp Val Leu Arg Asn Pro
                325                 330                 335

Thr Asp His Val Gly Phe Gly Tyr Gly Pro His Met Cys Val Gly Lys
            340                 345                 350

Ser Val Ser Asn Thr Glu Met Ile Ala Leu Trp Thr Glu Leu Gly Arg
        355                 360                 365

Arg Val Asp Arg Ile Glu Gln Ile Gly Pro Lys Lys Gln His Ile Asn
    370                 375                 380
```

-continued

```
Asn Leu Ile Arg Ser Leu Asp Ser Leu Pro Val Arg Ile Tyr Pro Lys
385                 390                 395                 400


<210> SEQ ID NO 9
<211> LENGTH: 321
<212> TYPE: DNA
<213> ORGANISM: Rhodococcus ruber
<220> FEATURE:
<221> NAME/KEY: CDS
<222> LOCATION: (1)..(318)

<400> SEQUENCE: 9

atg ccc aag atc acc ttc tcc caa tcg gac ggg tcg tcg atc acc gtc        48
Met Pro Lys Ile Thr Phe Ser Gln Ser Asp Gly Ser Ser Ile Thr Val
  1               5                  10                  15

gat gcg tcg ctg gac cag agc gtc atg cag gcc gcc gtc gcc gca ggt        96
Asp Ala Ser Leu Asp Gln Ser Val Met Gln Ala Ala Val Ala Ala Gly
             20                  25                  30

atc gac ggc atc ctc gcc gag tgc ggt ggc aac gcc acg tgt tcc acc       144
Ile Asp Gly Ile Leu Ala Glu Cys Gly Gly Asn Ala Thr Cys Ser Thr
         35                  40                  45

tgc cac gtg tac gtc gaa ccc gag caa ctc ggg ctc ctc gcg gac ctg       192
Cys His Val Tyr Val Glu Pro Glu Gln Leu Gly Leu Leu Ala Asp Leu
     50                  55                  60

agc gcc gaa gaa gac gac atg ctc gac tgc gcc gag gcc gaa cgt cgg       240
Ser Ala Glu Glu Asp Asp Met Leu Asp Cys Ala Glu Ala Glu Arg Arg
 65                  70                  75                  80

agc aac agc cgg ctg gcg tgt cag ctg ccg gtc acc acc gac ctc gac       288
Ser Asn Ser Arg Leu Ala Cys Gln Leu Pro Val Thr Thr Asp Leu Asp
                 85                  90                  95

ggg ctc cgg ctg gag gtc ccc gac gcg ttc tga                           321
Gly Leu Arg Leu Glu Val Pro Asp Ala Phe
            100                 105


<210> SEQ ID NO 10
<211> LENGTH: 106
<212> TYPE: PRT
<213> ORGANISM: Rhodococcus ruber

<400> SEQUENCE: 10

Met Pro Lys Ile Thr Phe Ser Gln Ser Asp Gly Ser Ser Ile Thr Val
  1               5                  10                  15

Asp Ala Ser Leu Asp Gln Ser Val Met Gln Ala Ala Val Ala Ala Gly
             20                  25                  30

Ile Asp Gly Ile Leu Ala Glu Cys Gly Gly Asn Ala Thr Cys Ser Thr
         35                  40                  45

Cys His Val Tyr Val Glu Pro Glu Gln Leu Gly Leu Leu Ala Asp Leu
     50                  55                  60

Ser Ala Glu Glu Asp Asp Met Leu Asp Cys Ala Glu Ala Glu Arg Arg
 65                  70                  75                  80

Ser Asn Ser Arg Leu Ala Cys Gln Leu Pro Val Thr Thr Asp Leu Asp
                 85                  90                  95

Gly Leu Arg Leu Glu Val Pro Asp Ala Phe
            100                 105


<210> SEQ ID NO 11
<211> LENGTH: 312
<212> TYPE: DNA
<213> ORGANISM: Rhodococcus ruber
<220> FEATURE:
<221> NAME/KEY: CDS
<222> LOCATION: (1)..(309)
```

-continued

<400> SEQUENCE: 11

```
atg tat cag atc gtg gcc tgc tac ggc cag ccc acc gac acc gag gcg        48
Met Tyr Gln Ile Val Ala Cys Tyr Gly Gln Pro Thr Asp Thr Glu Ala
  1               5                  10                  15

ttc gac acc tac tac gac agc acc cac gtg ccg ctg gcg aac aag ctc        96
Phe Asp Thr Tyr Tyr Asp Ser Thr His Val Pro Leu Ala Asn Lys Leu
             20                  25                  30

ccc ggc ctc gtc gac tac atc acg gtc aag tgc gtc tcg gca ctg ccc       144
Pro Gly Leu Val Asp Tyr Ile Thr Val Lys Cys Val Ser Ala Leu Pro
         35                  40                  45

ggg gaa ggg gtc ccg tac tac atg gtc gcg acc ctg acc ttc aac tcg       192
Gly Glu Gly Val Pro Tyr Tyr Met Val Ala Thr Leu Thr Phe Asn Ser
     50                  55                  60

gag cgc gac gtc aag gcc gcg ctt gag tcg ccg gag atg gac gcc gcg       240
Glu Arg Asp Val Lys Ala Ala Leu Glu Ser Pro Glu Met Asp Ala Ala
 65                  70                  75                  80

aag gcc gac gtc gcc aac ttc gcc acc ggc ggc ctg gcc ctc tac atc       288
Lys Ala Asp Val Ala Asn Phe Ala Thr Gly Gly Leu Ala Leu Tyr Ile
                 85                  90                  95

ggg gat gag gtc gac cgg acc tag                                       312
Gly Asp Glu Val Asp Arg Thr
            100
```

<210> SEQ ID NO 12
<211> LENGTH: 103
<212> TYPE: PRT
<213> ORGANISM: Rhodococcus ruber

<400> SEQUENCE: 12

```
Met Tyr Gln Ile Val Ala Cys Tyr Gly Gln Pro Thr Asp Thr Glu Ala
  1               5                  10                  15

Phe Asp Thr Tyr Tyr Asp Ser Thr His Val Pro Leu Ala Asn Lys Leu
             20                  25                  30

Pro Gly Leu Val Asp Tyr Ile Thr Val Lys Cys Val Ser Ala Leu Pro
         35                  40                  45

Gly Glu Gly Val Pro Tyr Tyr Met Val Ala Thr Leu Thr Phe Asn Ser
     50                  55                  60

Glu Arg Asp Val Lys Ala Ala Leu Glu Ser Pro Glu Met Asp Ala Ala
 65                  70                  75                  80

Lys Ala Asp Val Ala Asn Phe Ala Thr Gly Gly Leu Ala Leu Tyr Ile
                 85                  90                  95

Gly Asp Glu Val Asp Arg Thr
            100
```

<210> SEQ ID NO 13
<211> LENGTH: 4398
<212> TYPE: DNA
<213> ORGANISM: Rhodococcus ruber
<220> FEATURE:
<221> NAME/KEY: CDS
<222> LOCATION: (1)..(993)

<400> SEQUENCE: 13

```
atg gga acg tcg acg acg agc acg tcg cgg ccg gcc aga ccg acg tcg        48
Met Gly Thr Ser Thr Thr Ser Thr Ser Arg Pro Ala Arg Pro Thr Ser
  1               5                  10                  15

tcc gtc ttc tcg ctg aag aag ctg gag gag tcg gaa cgg gcg gtg acc        96
Ser Val Phe Ser Leu Lys Lys Leu Glu Glu Ser Glu Arg Ala Val Thr
             20                  25                  30
```

-continued

```
acc gcc ttc tat ccg cac aag gcg tcg atg gag cgc aat cag cag cag      144
Thr Ala Phe Tyr Pro His Lys Ala Ser Met Glu Arg Asn Gln Gln Gln
        35                  40                  45

ttc cgg ggg att ctc acc gtc cag aac gtc ggt ccg atc acc atc ggt      192
Phe Arg Gly Ile Leu Thr Val Gln Asn Val Gly Pro Ile Thr Ile Gly
    50                  55                  60

gaa ctg gac tac aac agc gag gtc tcc ctg gac ttc ccg cac atc acc      240
Glu Leu Asp Tyr Asn Ser Glu Val Ser Leu Asp Phe Pro His Ile Thr
 65                  70                  75                  80

aac ggg tac cac gtg aac gtc ccg gtc gag cac tcg atg tcg tcc aga      288
Asn Gly Tyr His Val Asn Val Pro Val Glu His Ser Met Ser Ser Arg
                 85                  90                  95

tcg cgc ggg cgg gag gtc cac atc acc ccg aag cac ggc gcg atg tac      336
Ser Arg Gly Arg Glu Val His Ile Thr Pro Lys His Gly Ala Met Tyr
            100                 105                 110

cgc aag gag gcg gac gcg ctg ctc aag ccg agc agg cga ctg cac atg      384
Arg Lys Glu Ala Asp Ala Leu Leu Lys Pro Ser Arg Arg Leu His Met
        115                 120                 125

acc gcg gtc aag ttc gac agc gcc gcc ctg gaa cag acg ttg tcg gcc      432
Thr Ala Val Lys Phe Asp Ser Ala Ala Leu Glu Gln Thr Leu Ser Ala
    130                 135                 140

ctg ctc ggc gaa ccc gtc gag gtg gat ctc gaa ctc gca tcc ggg atc      480
Leu Leu Gly Glu Pro Val Glu Val Asp Leu Glu Leu Ala Ser Gly Ile
145                 150                 155                 160

aat ctc gag cgc ggc ctg ggc aag gag tgg tgg gac ctg ctc tcc gac      528
Asn Leu Glu Arg Gly Leu Gly Lys Glu Trp Trp Asp Leu Leu Ser Asp
                165                 170                 175

gtc cgt cgg cag atc gac ggc ggc aac acg ctc ttc agc tgc cgg atg      576
Val Arg Arg Gln Ile Asp Gly Gly Asn Thr Leu Phe Ser Cys Arg Met
            180                 185                 190

gtc gcc gac ccg ctg gcc cag tcg ctc atg acc ggc ttc ctc ctc gcg      624
Val Ala Asp Pro Leu Ala Gln Ser Leu Met Thr Gly Phe Leu Leu Ala
        195                 200                 205

agt acc cat cag ttc tcc gag caa ctg cat tcg ggc gac tcg gtg gcg      672
Ser Thr His Gln Phe Ser Glu Gln Leu His Ser Gly Asp Ser Val Ala
    210                 215                 220

acg ccc gag tcg ttg aag ctc gtc gag gac gcc atc atg gcg cgg ctg      720
Thr Pro Glu Ser Leu Lys Leu Val Glu Asp Ala Ile Met Ala Arg Leu
225                 230                 235                 240

tcc gaa tcg ttc acg ttc acc gag atc gcg cag gaa gtc ggg atc agc      768
Ser Glu Ser Phe Thr Phe Thr Glu Ile Ala Gln Glu Val Gly Ile Ser
                245                 250                 255

ctc cgg gcc atc cag cgc gga ttc gcc cac cac atc ggc acg acc ccg      816
Leu Arg Ala Ile Gln Arg Gly Phe Ala His His Ile Gly Thr Thr Pro
            260                 265                 270

tcc caa ttc gtg cgg acc gaa cga ctg cga cgg gcc cac gtc gac ctc      864
Ser Gln Phe Val Arg Thr Glu Arg Leu Arg Arg Ala His Val Asp Leu
        275                 280                 285

gtc gcc ggt gat ccg tcg acc acc cgg gtc gcc gat gtc gca gcc cgc      912
Val Ala Gly Asp Pro Ser Thr Thr Arg Val Ala Asp Val Ala Ala Arg
    290                 295                 300

tgg ggc ttc acc cat ctc ggc cgg ttc tcg gcg cag tac cga aag ctc      960
Trp Gly Phe Thr His Leu Gly Arg Phe Ser Ala Gln Tyr Arg Lys Leu
305                 310                 315                 320

tac ggc gtg agt ccc tcg gac acc ttg cgc tcc tagggttctc gacgcccagc   1013
Tyr Gly Val Ser Pro Ser Asp Thr Leu Arg Ser
                325                 330

cctactcccc ctcacccacc cacccacccc atctcctctc gatgccgacc cctgcggggt   1073

acggccagtg acgtgatccc gaaacccctc tccggcaatc gacgcatgcc cttgccgcgc   1133
```

-continued gtgaaaggaa gcgaagttga cgacgaccac cgcgacgctc accgacgtga tcatcatcgg 1193
cgccgggcag ggcggcctgc aggcagcgat gtcgctgcgc gatcacggct atacgggccg 1253
cctgacgatc gtcggcgacg aaccgggcct gccgtatcag cgtcctccgc tgtcgaaggc 1313
gtatctcatc aacgacgacg ccatgtcgga ggaactcctg ctgctccggc cgcactcggt 1373
gttcgagcga ctcgacatcg acctcatcac cggtgacggc gtcacccgca tcgaccgggt 1433
ccgcagcacc gtgtcgctga gttcgggtcg cgaactggcc ttcgaccacc tgatcctggc 1493
caccggcgcc cggccgcggg agctgagcgt gccgggcgcc gacctcgcgg gagtggaggc 1553
actgcgtacg tgcgacgacg cgaaggcgat ccgcgcgggg ctcaccggcc cggcacgggt 1613
cgtggtgatc ggcggcggct ttgtcgggac cgaggtggcc gccgcggcga ccaagcgagg 1673
ccactccgtg acgatcgtcg acatggaggc ccgtctcctc aatcgggctg tgtccccgga 1733
gatctccgca ctcgtcacgg cggcgcatcg ccgcagggga accgcggtcg tcctgaacgc 1793
cggcgtcagc cggctgtgcg gctccgacgg caccgtcgaa gccgtggaac tcactgacgg 1853
gcaacggatt ccggccgact tcgtagttgt cggcatcggc gtcgtgccca acacggagat 1913
cgcccacgac gccggcctcg ccgtcgacaa cggcattctc gtcgatgacc ggttgcgcac 1973
caacgaccac cggatcagtg cgatcggcga ctgcgcgcga ttcccgtgcg cacacgccga 2033
cggccagatg ctgcgcctcg aatcggtgca gaacgccgtc gaccacgcac gacacgtcgc 2093
cgcccgactc atgggcgacg caggacccta cgacgccgtg ccgtggttct ggaccgacca 2153
gtgcggactg aagatccaga tcgccggaat cggcgcgcag ggcgccgagt cggtggtgat 2213
cggcgacgag gcagcagaac gatgttcggt gctgcggttc cgctccggcg aactgtcctg 2273
tgtggagtcg gtcaacagca gcggcgagca catggccgca cgcaagatcc tgcgcggtgg 2333
accgcgcccg gtggcgcccg tcgacgggtc acccgctgcc ttcgacctca aacacatcgc 2393
ccgggaggtc gccacggctc gctgagaacc cagtcctgac acctagtggt gcactgcacc 2453
tttcaccgac acacccctga tcgaggagga atctatgaca ctgtcactgg ccacggccca 2513
ggaacgctat gccaccgatg cggacgtctt cgcacacgac accctggtcg atccctacga 2573
cacgtatcgg tcgctgcgcg acatcggccg tgtgtcgtac atgacccggt acgacacgtg 2633
ggcgctcacc cgctacgacg aggtccgtca cgcgctcggc gactggcaga cgttcagttc 2693
ggcgcaggga atcggaatga gcacggcact caacgaggcg tggaaggact tcgcgccgtg 2753
caaggacggc gccgaccacc tgcccatgcg gaagttgatg atgcaggacc tcggccccaa 2813
agccgccgcg gcctacaagg agaagatcca gcaggccgcc gtgacgctcg tcgaggagtt 2873
gctcgatcgc cgcgagttcg acgcggtgct cgacttcgcc cagatgatgc cgatgcgggt 2933
gttcatggag gtgctcggtg tcgagcccga catcgaacag cgccgcacga tgctgcactg 2993
ggggaccgac acctacaact gcgcggcgcc ggacggcctc tacgacgaca ccctgcccag 3053
catggacaag ctctacagct gggcgctgga gaacatcact ccggagaccg cacgcgaggg 3113
cagcgtcgcc gcgtcgacgt gggagtcggt ggaacgcggc gacatcaccg acgtgcaggc 3173
ggtcgcgacc ctggcggctt acgtcaccgc cggactcgac accaccgccg gtaccctcgg 3233
caacacgatc gcgcagttcg cggcgaaccc ggaccagtgg gccatcgtcc gcgacgaccc 3293
caagaccatc ccgggcgcga tcctcgaggg catccggttc gacagcgtgg cgcagtggtt 3353
cacccgcgtg accacccgcg acgtcgagta cgacgacatc gtcatccccg cggggtcgcg 3413
gacgtatcac tcctacgcgg cggcaaaccg ggacgagcgg cactaccgcg accccgactc 3473

-continued

```
cttcgacgtg ctgcgcaacc ccaccgacca cgtggggttc gggtacggcc cgcacatgtg   3533

cgtcggaaag tcggtgtcca acaccgagat gatcgccctg tggaccgaac tcggccgccg   3593

ggtggatcgc atcgagcaga tcggcccgaa gaagcagcac atcaacaacc tcatccgcag   3653

cctcgattcg ctgcccgtgc ggatctaccc gaagtgatgc cgatgcccaa gatcaccttc   3713

tcccaatcgg acgggtcgtc gatcaccgtc gatgcgtcgc tggaccagag cgtcatgcag   3773

gccgccgtcg ccgcaggtat cgacggcatc ctcgccgagt gcggtggcaa cgccacgtgt   3833

tccacctgcc acgtgtacgt cgaacccgag caactcgggc tcctcgcgga cctgagcgcc   3893

gaagaagacg acatgctcga ctgcgccgag gccgaacgtc ggagcaacag ccggctggcg   3953

tgtcagctgc cggtcaccac cgacctcgac gggctccggc tggaggtccc cgacgcgttc   4013

tgaacgcgtc cggcaccagc cgcctcccac cacacaagaa ctgttcgcag taccaatcac   4073

caaggagtgc accatgtatc agatcgtggc ctgctacggc cagcccaccg acaccgaggc   4133

gttcgacacc tactacgaca gcacccacgt gccgctggcg aacaagctcc ccggcctcgt   4193

cgactacatc acggtcaagt gcgtctcggc actgcccggg gaaggggtcc cgtactacat   4253

ggtcgcgacc ctgaccttca actcggagcg cgacgtcaag gccgcgcttg agtcgccgga   4313

gatggacgcc gcgaaggccg acgtcgccaa cttcgccacc ggcggcctgg ccctctacat   4373

cggggatgag gtcgaccgga cctag                                         4398
```

```
<210> SEQ ID NO 14
<211> LENGTH: 331
<212> TYPE: PRT
<213> ORGANISM: Rhodococcus ruber

<400> SEQUENCE: 14

Met Gly Thr Ser Thr Thr Ser Thr Ser Arg Pro Ala Arg Pro Thr Ser
1               5                   10                  15

Ser Val Phe Ser Leu Lys Lys Leu Glu Glu Ser Glu Arg Ala Val Thr
            20                  25                  30

Thr Ala Phe Tyr Pro His Lys Ala Ser Met Glu Arg Asn Gln Gln Gln
        35                  40                  45

Phe Arg Gly Ile Leu Thr Val Gln Asn Val Gly Pro Ile Thr Ile Gly
    50                  55                  60

Glu Leu Asp Tyr Asn Ser Glu Val Ser Leu Asp Phe Pro His Ile Thr
65                  70                  75                  80

Asn Gly Tyr His Val Asn Val Pro Val Glu His Ser Met Ser Ser Arg
                85                  90                  95

Ser Arg Gly Arg Glu Val His Ile Thr Pro Lys His Gly Ala Met Tyr
            100                 105                 110

Arg Lys Glu Ala Asp Ala Leu Leu Lys Pro Ser Arg Arg Leu His Met
        115                 120                 125

Thr Ala Val Lys Phe Asp Ser Ala Ala Leu Glu Gln Thr Leu Ser Ala
    130                 135                 140

Leu Leu Gly Glu Pro Val Glu Val Asp Leu Glu Leu Ala Ser Gly Ile
145                 150                 155                 160

Asn Leu Glu Arg Gly Leu Gly Lys Glu Trp Trp Asp Leu Leu Ser Asp
                165                 170                 175

Val Arg Arg Gln Ile Asp Gly Gly Asn Thr Leu Phe Ser Cys Arg Met
            180                 185                 190

Val Ala Asp Pro Leu Ala Gln Ser Leu Met Thr Gly Phe Leu Leu Ala
        195                 200                 205
```

-continued

```
Ser Thr His Gln Phe Ser Glu Gln Leu His Ser Gly Asp Ser Val Ala
    210                 215                 220

Thr Pro Glu Ser Leu Lys Leu Val Glu Asp Ala Ile Met Ala Arg Leu
225                 230                 235                 240

Ser Glu Ser Phe Thr Phe Thr Glu Ile Ala Gln Glu Val Gly Ile Ser
                245                 250                 255

Leu Arg Ala Ile Gln Arg Gly Phe Ala His His Ile Gly Thr Thr Pro
            260                 265                 270

Ser Gln Phe Val Arg Thr Glu Arg Leu Arg Arg Ala His Val Asp Leu
        275                 280                 285

Val Ala Gly Asp Pro Ser Thr Thr Arg Val Ala Asp Val Ala Ala Arg
    290                 295                 300

Trp Gly Phe Thr His Leu Gly Arg Phe Ser Ala Gln Tyr Arg Lys Leu
305                 310                 315                 320

Tyr Gly Val Ser Pro Ser Asp Thr Leu Arg Ser
                325                 330
```

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
acccccgcaa tcgtcggc 18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
tgccggcggc tccgctga 18

<210> SEQ ID NO 17
<211> LENGTH: 15
<212> TYPE: PRT
<213> ORGANISM: Rhodococcus ruber

<400> SEQUENCE: 17

```
His Ala Leu Gly Asp Trp Gln Thr Phe Ser Ser Ala Gln Gly Ile
  1               5                  10                  15
```

<210> SEQ ID NO 18
<211> LENGTH: 10
<212> TYPE: PRT
<213> ORGANISM: Rhodococcus ruber

<400> SEQUENCE: 18

```
Phe Asp Ser Val Ala Gln Trp Phe Thr Arg
  1               5                  10
```

<210> SEQ ID NO 19
<211> LENGTH: 15
<212> TYPE: PRT
<213> ORGANISM: Rhodococcus ruber

<400> SEQUENCE: 19

-continued

Ser Val Ser Asn Thr Glu Met Ile Ala Leu Trp Thr Glu Leu Gly
1 5 10 15

<210> SEQ ID NO 20
<211> LENGTH: 14
<212> TYPE: PRT
<213> ORGANISM: Rhodococcus ruber

<400> SEQUENCE: 20

Gly Gln Pro Thr Asp Thr Glu Ala Phe Asp Thr Tyr Tyr Ser
1 5 10

<210> SEQ ID NO 21
<211> LENGTH: 15
<212> TYPE: PRT
<213> ORGANISM: Rhodococcus ruber

<400> SEQUENCE: 21

His Ala Leu Gly Asp Trp Gln Thr Phe Ser Ser Ala Gln Gly Ile
1 5 10 15

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic consensus sequence
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid

<400> SEQUENCE: 22

Gly Xaa Gly Xaa Xaa Gly
1 5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic consensus sequence
<220> FEATURE:
<221> NAME/KEY: MOD_RES
<222> LOCATION: (3)
<223> OTHER INFORMATION: Variable amino acid
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (9)
<223> OTHER INFORMATION: Variable amino acid

<400> SEQUENCE: 23

Phe Gly Xaa Gly Xaa His Xaa Cys Xaa Gly
1 5 10

-continued

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (6)
<223> OTHER INFORMATION: Inosine
<220> FEATURE:
<221> NAME/KEY: modified_base
<222> LOCATION: (9)
<223> OTHER INFORMATION: Inosine

<400> SEQUENCE: 24
caygcnytng aytggcagac stt 23

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (3)
<223> OTHER INFORMATION: Inosine
<220> FEATURE:
<221> NAME/KEY: modified_base
<222> LOCATION: (9)
<223> OTHER INFORMATION: Inosine
<220> FEATURE:
<221> NAME/KEY: modified_base
<222> LOCATION: (12)
<223> OTHER INFORMATION: Inosine
<220> FEATURE:
<221> NAME/KEY: modified_base
<222> LOCATION: (24)
<223> OTHER INFORMATION: Inosine

<400> SEQUENCE: 25
tcngtccana gngckatcat ytcngtgtt 29

CYTOCHROME P-450 GENE CLUSTER FROM *RHODOCOCCUS RUBER* AND USES THEREOF IN ETHER FUEL CLEAVAGE

CROSS REFERENCE TO RELATED APPLICATIONS

This application is a continuation of international application number PCT/EP02/08066, filed Jun. 20, 2002, and claims the priority of European Patent Application No. 01401667.9, filed Jun. 22, 2001.

The present invention is directed to a cytochrome P-450 gene cluster involved in the leavage of ether fuel additives. More especially, the present invention pertains to the nucleic acid sequence of genes responsible for the biodegradation of ethyl tert-butyl ether (ETBE) in *Rhodococcus ruber*, and to several applications ensuing from the knowledge of this sequence, such as probes and biosensors for detecting a pollution by an ether fuel, and for assessing the potential of a contaminated soil or effluent to cleave said ether fuel. The invention also pertains to methods for rendering a cell able to cleave ether fuel additives, and to bacteria useful for ether fuel depollution of a contaminated soil or effluent.

Methyl tert-butyl ether (MTBE) and ethyl tert-butyl ether (ETBE) are used as additives in unleaded gasoline. These ethers were originally used to enhance the octane number of gasoline. The octane number, also called Antiknock Rating, measures the ability of a fuel to resist knocking when ignited in a mixture with air in the cylinder of an internal-combustion engine. The octane number is determined by comparing, under standard conditions, the knock intensity of the fuel with that of blends of two reference fuels: iso-octane, which resists knocking, and heptane, which knocks readily. The octane number is the percentage by volume of iso-octane in the iso-octane/heptane mixture that matches the fuel being tested in a standard test engine.

Now, MTBE and ETBE are also used as oxygenates, to raise the oxygen content of gasoline, in order to improve combustion efficiency, thereby reducing emissions of unburnt hydrocarbons to the atmosphere.

Typically, concentrations up to 15% (v/v) MTBE can be us d in oxygenated gasoline, making MTBE one of the main organic chemicals produced in the United States. ETBE is used in some European countries and its interest resides in its potential to increase the market for ethanol, as ETBE is manufactured from ethanol and isobutene. ETBE also has technical superiority compared to MTBE, in terms of lower vapor pressure and higher octane number.

The widespread use of ethers in gasoline has resulted in their introduction from leaky tanks and spills into groundwater, exposing people to low levels of ethers from drinking water. Compared with other compounds in gasoline, ethers are relatively nontoxic. However, the carcinogenicity of these compounds is still uncertain. Moreover, their unpleasant taste and odor at very low concentrations render water unfit for drinking, making these xenobiotic compounds important pollutants.

To develop bioremediation of these compounds, studies on the biodegradability of MTBE and ETBE have been undertaken. Bacteria capable of using MTBE as the sole carbon and energy source have been isolated (16, 27). To date, the enzymatic mechanism used by these bacteria to degrade MTBE has not been elucidated. Several microorganisms, which cannot use MTBE as the sole carbon and energy source, can degrade MTBE during, or after, growth on an inducer substrate. Using pentane as the source of carbon and energy, *Pseudomonas aeruginosa* was shown to degrade MTBE (14).

The filamentous fungus *Graphium* sp. and *Pseudomonas putida* degrade MTBE after growth on n-butane, and camphor, respectively (17, 35). Propane-oxidizing bacteria, including *Mycobacterium vaccae* JOB5, were shown to degrade MTBE or ETBE after growth on propane (35). MTBE and ETBE were oxidized to tert-butyl alcohol (TBA) which was further oxidized to products not effective for growth of the propane oxidizers. Oxidation of both MTBE and TBA involves a soluble cytochrome P-450 which corresponds most likely to the propane mono-oxygenase (PMO).

Fayolle et al. first isolated two bacterial strains capable of using ETBE as the sole source of carbon and energy (11). They identified these two strains as actinomycetes *Gordonia terrae* and *Rhodococcus equi*, but further studies, based on the analysis of 16S RNA sequences, showed that these strains were *Rhodococcus ruber* and *Rhodococcus zopfii*, respectively. Both strains stoichiometrically convert ETBE into TBA, which accumulates in the culture medium. *R. ruber* is unable to use MTBE or tert-amyl methyl ether (TAME) as the sole carbon and energy source, but can degrade MTBE or TAME, to TBA or tert-amyl alcohol (TAA), respectively, after growth on ETBE (18). The same enzyme system accounts for the degradation of MTBE, TAME, ETBE and presumably other ether fuels, as shown in Example 9. One mole of oxygen is consumed per mole of ETBE degraded, which suggests that scission of the ether bond proceeds through hydroxylation by a monooxygenase, yielding a hemiacetal intermediate which spontaneously dismutates into TBA and acetaldehyde. The most likely monooxygenase candidate is an inducible cytochrome P-450, which was detected as a peak at 447 nm in the carbon monoxide difference spectrum of reduced crude extracts of R. Tuber grown on ETBE (18).

The invention provides means for ether fuel cleavage by an oxidative process, therefore providing means for degrading components of gasoline causing problems when spilled in the environment owing to their high solubility in water or to their poor biodegradability. It results from the genomic characterization of wild-type *R. ruber* and of spontaneous mutants of *R. ruber* unable to use ETBE as the sole source of carbon and energy. Loss of the ability to degrade ether fuel additives such as ETBE was shown to result from a chromosomal deletion secondary to a recombination between direct repeats. The deletion led to the removal of an operon (hereafter termed the eth cluster), encoding a cytochrome P-450 system, whose expression was induced by ETBE, demonstrating its essential role in the cleavage of ether fuels by *R. ruber.*

The analysis of the genomes of the wild-type and spontaneous mutant of *R. ruber*, performed as described in the experimental section, shows an organization wherein the spontaneous mutant results from an homologous recombination between two identical direct repeats of the same sequence, which is a class II transposon. This homologous recombination results in the deletion of the sequences comprised between the 5' end of the first transposon and the 5' end of the second transposon.

This fragment has been shown to contain the eth gene cluster, and the mutant is unable to cleave ether fuels. This phenomenon appears clearly in FIG. 4, wherein the restriction map of the genome region in which this deletion occurs is compared to that of the same region of the wild-type strain.

FIG. 4A represents the restriction map of a 23.7 kpb BamHI fragment of SEQ ID No: 1, comprising a duplicated region of 5.6 kpb (hatched boxes, SEQ ID No:4) flanking a 8.7 kbp region (SEQ ID No: 3) which includes the eth cluster. FIG. 4B represents the same BamHI fragment, after the deletion of a 14.3 kpb of SEQ ID No: 2, by chromosomal rearrangement between the two duplicated regions.

Moreover, the eth gene cluster is most probably present and expressed in *Rhodococcus equi* (now identified as *Rhodococcus zopfii*), which is another bacterial strain able to degrade ETBE (11). Indeed, the inventors have shown that the ethB gene present in *R. zopfii* exhibits more than 98% identity with that of *R. ruber* (previously identifies as *G. terrae*) (Example 10). Probes derived from the ethB gene of *R. ruber* hybridize to restriction fragments of the *R. zopfii* genome which have the same size as those from the *R. ruber* DNA.

Other ETBE-degrading bacteria possess cytochrome P-450 systems highly similar to that of *R. ruber*, as shown in Examples 9 and 10.

The inventors have also shown (Example 12) that the *R. ruber* mutant lacking the eth cluster can recover the ability to use ETBE as a carbon source after being transformed by a plasmid comprising the eth cluster.

These results, added to those obtained with *R. ruber* and detailed in the experimental-part, demonstrate that products of the eth gene cluster are involved, individually or collectively in the cleavage of ether fuels.

The invention therefore pertains to isolated nucleic acid sequences hybridizing to the DNA sequences of the genes responsible for the degradation of ETBE in a strain initially identified as *Gordonia terrae* (11), now identified as on the basis of 16S RNA sequence analysis. This strain was deposited at the *Rhodococcus ruber* Collection Nationale de Cultures de Microorganismes (CNCM), 28 rue du Docteur Roux, F-75724 Paris Cedex 15, France, under the reference I-1889, on Jun. 25, 1997. The invention also pertains to vectors comprising at least one of these nucleic acid sequences, and to recombinant bacteria containing at least one of these vectors. The invention also concerns probes and primers specific for the eth cluster, methods and biosensors for identifying the presence in a sample of a microorganism comprising this cluster and, if necessary, for isolating such microorganisms. The present invention also pertains to biosensors for detecting a pollution by ETBE or other ether fuel additives, as well as to processes for depolluting an effluent, a soil or a sludge contaminated with an ether fuel, by the use of a microorganism, recombinant or not, which exhibits the properties of the eth cluster.

Throughout this application, several words are employed, the meaning of which should be understood according to the following definitions:

The phrase "ether fuel additive" designates a compound comprising an ether function and which is used in gasoline to improve combustion efficiency and/or to enhance the octane number of said gasoline. The most commonly used ether fuel additives are the methyl tert-butyl ether (MTBE) widely used in the US, and the ethyl tert-butyl ether (ETBE) mainly used in Europe. Other ether fuel additives are presently tested, such as tertiary amyl methyl ether (TAME) and tertiary amyl ethyl ether (TAEE). Further ethers may be used in the future as fuel additives and exhibit technical superiority compared to the presently used ether fuel additives. In this application and in the technical literature, the phrase "ether fuel" is also used to designates the above-defined compounds.

"Stringent hybridization conditions" are defined here as conditions that enable specific hybridization of two single-strand DNA molecules at about 65° C., for example in a solution of 6×SSC, 0.5% SDS, 5× Denhardts solution and 100 μg/ml of denatured unspecific DNA, or any other solution of equivalent ionic strength, and after a washing step performed at 65° C., for example in a solution of at most 0.2×SSC and 0.1% SDS, or any other solution of equivalent ionic strength. However, the stringency conditions can be adapted by the skilled artisan, depending on the size of the hybridizing sequence, its GC content and any other parameter, for example according to the protocols that are described in Sambrook et al., 2001 (Molecular Cloning: A Laboratory Manual, 3$^{rd}$ Ed., laboratory press, Cold Spring Harbor, N.Y.).

A sequence S2 is "derived from" a sequence S1 if S2 is a fragment of S1, or a variant of S1, or a variant of a fragment of S1. A sequence comprising S1 or a fragment of S1, or a variant of S1, or a variant of a fragment of S1 is said "derived from" S1 as well. In this definition, a "fragment" is longer than 10 nucleotides, preferably longer than 20 nucleotides, and even more preferably longer than 50 nucleotides. In the whole application, a "variant" of a nucleotide sequence designates a sequence which is at least 60%, and preferably at least 80% identical to said nucleotide sequence, the percentage of nucleic acid identity between two nucleic acid sequences being calculated using the BLAST software (Version 2.06 of September 1998).

A bacterium B2 will be said "derived from" a bacterium B1 if B2 has been obtained by sub-cloning B1 cells, optionally after culturing B1 in specific conditions, or after introducing a foreign DNA into B1 cells. In particular, a bacterium B2 can be derived from B1 by chromosomal rearrangement.

In this application a "functional variant" of a protein P1 designates a protein P2 which can complement the absence of P1 in a biological process in which P1 is usually involved. For example, a functional variant of EthB is able to replace the native EthB in the cytochrome P-450 system in such a way that this system keeps its ability to degrade ETBE.

An "ETBE-negative" bacterium means here a bacterium which cannot degrade ETBE, whereas an "ETBE-positive" bacterium is able to degrade ETBE, whatever the degradation product(s) obtained.

A first embodiment of the present invention is an isolated nucleic acid sequence which specifically hybridizes under stringent conditions with the genome of *Rhodococcus ruber* I-1889, as deposited at the Collection Nationale de Culture de Microorganismes (CNCM) and does not hybridize under stringent conditions with the genome of a bacterial cell derived from *Rhodococcus ruber* I-1889 by chromosomal rearrangement resulting in a 14.3 kbp deletion including the eth gene cluster and the loss of the ability to degrade ETBE. The nucleic acids designated here are nucleic acids which hybridize with the DNA fragment that is absent in a bacterial cell derived from *Rhodococcus ruber* I-1889 by chromosomal rearrangement resulting in a 14.3 kbp deletion including the eth gene and do not hybridize with the sequences flanking said eth gene cluster. In other words, the nucleic acids designated here are nucleic acids which hybridize with the DNA fragment of *Rhodococcus ruber* I-1889 eth gene cluster which is a 8.7 kpb fragment represented by the white box between the two hatched boxes in FIG. 4A (SEQ ID No: 3). Such a nucleic acid can also be "derived from" SEQ ID No:3 as defined above.

In another aspect of the invention, the application pertains to an isolated nucleic acid sequence which specifically hybridizes under stringent conditions with at least one of the nucleic acids of SEQ ID No: 5, 7, 9, 11, or 13 (ethA, B, C, D or R ORF, respectively), wherein said nucleic acid sequence encodes a protein of SEQ ID No: 6, 8, 10, 12 or 14, respectively, or a functional variant thereof, according to the above definition.

A third aspect of this invention pertains to an isolated nucleic acid sequence having the following properties:

a) it hybridizes under stringent conditions with a nucleic acid of SEQ ID No: 2, and preferably hybridizes also under stringent conditions with a nucleic acid of SEQ ID No: 3;

b) when transferred into a bacterial cell derived from *Rhodococcus ruber* I-1889 by chromosomal rearrangement resulting in a 14.3 kbp deletion including the eth gene cluster, it confers to this bacterium the ability to degrade ETBE.

In this embodiment, the application hence pertains to a nucleic acid which can trans-complement the genome of an ETBE-negative *Rhodococcus ruber* bacterium in order to render this bacterium ETBE-positive. This nucleic acid does not necessarily contain the whole SEQ ID No: 2. On the contrary, some parts of this sequence can be deleted and/or substituted by a different sequence. For example, the ethR gene can be deleted and the eth promoter replaced by a strong constitutive promoter. Alternatively, any of the ethA, B, C, and D ORFs can be replaced by a sequence encoding a functional variant of Eth A, B, C, and D, respectively. Such a variant can be obtained by mutagenesis or by DNA shuffling between homologous genes of different bacteria, and functional screening to find a variant which is at least as functional as the natural Eth A, B, C, or D.

The present invention also pertains to a vector comprising any nucleic acid of the invention as described above. For example, a vector encoding EthR as a transcriptional activator for an heterologous gene is within the scope of the present invention. A vector of the invention can be for example a plasmid, a cosmid, a phage or a virus.

A recombinant *Escherichia coli* bacterium comprising a vector as described above was deposited at the Collection Nationale de Cultures de Microorgantsmes (CNCM) on Apr. 19, 2001, under the name of *Escherichia coli* K12 (pGT220) and number I-2662. This bacterium is part of the invention as well.

The invention also pertains to a nucleic acid probe for the detection or characterization of bacterial strains able to degrade ether fuel additives, which hybridizes under stringent conditions with a) a 23.7 kb nucleic acid of SEQ ID No: 1, comprising the eth cluster of *R. ruber*, wherein this nucleic acid corresponds to a fragment resulting from the partial digestion of *R. ruber* DNA by the restriction endonuclease BamHI, and/or b) a 1-4.3 kb nucleic acid corresponding to the fragment deleted in *R. ruber* ETBE-negative bacteria derived from *Rhodococcus ruber* I-1889 by chromosomal rearrangement resulting in a 14.3 kbp deletion including the eth gene cluster (SEQ ID No: 2) and/or c) a 8.7 kb nucleic acid corresponding to the genome fragment which is absent in ETBE-negative bacteria derived from *Rhodococcus ruber* I-1889 by chromosomal rearrangement resulting in a 14.3 kbp deletion including the eth gene cluster (SEQ ID No: 3).

Another object of the present invention is a nucleic acid primer specifically hybridizing with a DNA sequence of SEQ ID No: 1, wherein said primer can be used for the amplification of a DNA sequence included in SEQ ID No: 1 by any means, for example by PCR. A preferred primer of the invention specifically hybridizes with a DNA sequence of SED ID No: 3.

The invention also pertains to an antibody specifically binding to a polypeptide of SEQ ID No: 6, 8, 10, 12 or 14. Such an antibody can be obtained, for example, by immunizing an animal with a polypeptide of SEQ ID No: 6, 8, 10, 12 or 14, or with a truncated form of these polypeptides, or with a fusion protein comprising part of these polypeptides. In order to know whether an antibody is in the scope of the invention, a binding assay can be performed with said antibody, using protein extracts from *Rhodococcus ruber* I-1889 and from a *R. ruber* ETBE-negative bacterium derived from *Rhodococcus ruber* I-1889 by chromosomal rearrangement resulting in a 14.3 kbp deletion including the eth gene cluster. If the signal obtained with the extract from the ETBE-positive bacterium is significantly higher than that obtained with the extract from the ETBE-negative mutant, the tested antibody is in the scope of the present invention. This assay can be performed using the protocols of Sambrook et al., 2001 (Molecular Cloning: A Laboratory Manual, $3^{rd}$ Ed., laboratory press, Cold Spring Harbor, N.Y.) for the preparation of protein extracts and for testing the binding affinity of the antibody to said extracts, for example by Western blot.

As explained in the following experimental examples, the inventors have demonstrated that the ethB gene encodes a cytochrome P-450 of SEQ ID No: 8, or a variant thereof, which catalyzes the oxidation of ETBE. This cytochrome P-450 is also part of the present invention, as well as the other proteins EthA, EthC, EthD and EthR expressed by the open reading frames ethA, ethC, ethD and ethR, respectively.

As described in Example 5, Eth A is similar to a glutathione reductase-like ferrodoxin, and Eth C is a putidaredoxin-type [2Fe-2S] ferrodoxin which probably serves as an electron carrier between the NADH-dependent ferredoxin reductase (EthA) and the cytochrome P-450 (EthB). These two polypeptides are most probably involved in a complex with the cytochrome P450 of SEQ ID No:11. The fact that Eth D is more abundant in *R. ruber* in the presence of ETBE suggests that this polypeptide Interacts with the cytochrome P450 as well. Any complex of at least two polypeptides from the group of Eth A, Eth B, Eth C and Eth D, is also part of this invention.

The inventors have also demonstrated that *Rhodococcus ruber* I-1889 often looses its ability to degrade ETBE by chromosomal rearrangement resulting in a 14.3 kbp deletion including the eth gene cluster, and that this rearrangement occurs between two 5.6 kpb duplicated sequences (of SEQ ID No: 4). In order to prevent this rearrangement, and thereby obtain more stable ETBE-positive bacteria, it is possible to delete all or part of at least one copy of this duplicated sequence. Therefore, a recombinant bacterium derived from *Rhodococcus ruber* I-1889 by deletion of all or part of at least one copy of the DNA fragment of SEQ ID No: 4 is also in the scope of the present application.

The invention also pertains to a recombinant bacterium comprising any above-described nucleic acid molecule or vector of the invention. This bacterium can comprise a vector encoding the whole eth gene cluster, or only part of this cluster. For example, a bacterium comprising a plasmid encoding a gene responsible for the degradation of TBA (which is a degradation product of ETBE), said gene being under the control of a promoter including the ethR ORF, is in the scope of this invention. Such a bacterium could advantageously be used with *Rhodococcus ruber* I-1889 to completely degrade ETBE, because the genes for both the degradation of ETBE and TBA would be induced by ETBE.

A preferred embodiment of this invention is a recombinant bacterium as described above, which is able to degrade ETBE and other ether fuels. Another preferred embodiment of this invention is a recombinant bacterium which can use ETBE as sole source of carbon.

The identification of a cytochrome P-450 system involved in ETBE degradation by *R. ruber* provides new insights into the biodegradation mechanism, and therefore into the bioremediation process of gasoline oxygenates. For instance, it would be interesting to transfer the eth genes into a TBA-degrading strain, in order to produce a recombinant strain which would mineralize ETBE completely. Therefore, a recombinant bacterium comprising a vector encoding the eth genes, which is capable of degrading one ether fuel and its degradation products, for example cleaving ETBE and also capable of degrading TBA, is in the-scope of the present invention. In a preferred embodiment of the recombinant bacteria of the invention, these bacteria are capable of completely mineralizing ETBE, which means degrading these compounds to innocuous compounds, such as $CO_2$ and water.

Another aspect of the invention is a method for rendering a cell able to cleave ether fuel additives, comprising the step of introducing into said cell a nucleic acid or a vector encoding at least part of the Eth proteins, or functional variants thereof, as described above. A method for improving the efficiency of ether fuels degradation is also considered here. This can be achieved for example, by increasing the copy number of the eth gene cluster in a cell, or by driving the expression of the eth genes from a promoter stronger than the natural one. Alternatively or additionally, it is possible to increase the functionality of at least one of the Eth proteins, for example the cytochrome P-450 (EthB), for example by performing DNA shuffling between several genes homologous to ethB, and screen the obtained proteins for their ability to complement EthB in the cytochrome P-450 system, in ETBE degradation experiments.

In the above method, the cell to be rendered capable of cleaving ether fuel additives is preferentially a bacterium. Alternatively, this method can be performed on a plant, fungal or yeast cell.

Beside, it can be very useful to assess the potential of ether fuel cleavage in an area contaminated with other fuels, in order to determine which actions should be undertaken to protect the environment. Therefore, the invention also pertains to a method for identifying in a complex mixture the presence of a microorganism comprising at least part of the eth gene cluster able to confer to a bacterial strain the ability to cleave an ether fuel additive, comprising the step of contacting said sample with a nucleic acid probe and/or an antibody as mentioned above.

For the same reason, a method for identifying in a complex mixture the presence of a microorganism comprising at least part of the eth gene cluster able to confer to a bacterial strain the ability to cleave an ether fuel additive, comprising the step of performing a DNA amplification with at least one primer as described above, is also part of the present invention.

Whether the detection is performed using hybridization with a probe, antibody binding, or amplification with primers, the skilled artisan is able to adapt the detection means to the kind and amount of sample treated and the treatment used. For example, the probe or the primers can be radiolabelled or fluorescent, or even coupled to an enzyme.

In the above described methods, the complex mixture can be for example a sample of water, soil, sludge, sediment, dredge tailing, gas or chemical waste.

To determine the presence or absence in a contaminated sample, of microorganisms likely to cleave ether fuels, the invention further pertains to a biosensor comprising a nucleic acid as described above (isolated fragment, vector, probe, primer, . . . ), and/or an antibody specifically binding to a polypeptide encoded by one of the genes of the eth gene cluster, i.e., a polypeptide of any of SEQ ID No: 6, 8, 10, 12 or 14.

The invention also pertains to a method for isolating a microorganism able to cleave ether fuel additives, comprising the step of detecting the presence or absence in a sample, of the eth gene cluster included in SEQ ID No: 3 or a sequence derived from SEQ ID No: 3. SEQ ID No: 3 corresponds to the DNA fragment which is absent from the genome of a bacterial cell derived from *Rhodococcus ruber* I-1889 by chromosomal rearrangement resulting in a 14.3 kbp deletion including the eth gene cluster and the loss of the ability to degrade ETBE. The skilled artisan is able to determine the means to detect the presence or absence in a sample, of this DNA fragment, for example by using a probe specifically hybridizing to this fragment, or by performing DNA amplification with at least one primer specific for this fragment. A method for isolating a microorganism able to cleave ether fuel additives, comprising the step of detecting the presence or absence in a sample, of a nucleic acid hybridizing under stringent conditions with a nucleic acid probe as described above, is part of the invention as well. In a preferred embodiment of this method, the nucleic acid probe is specific for the sequence of SEQ ID No: 3.

The invention also pertains to a bacterium which is able to cleave an ether fuel additive, and which has been identified and/or isolated by a method as described above.

Another bacterium according to the invention is a recombinant bacterium comprising a reporter gene under the control of the eth promoter. Indeed, the inventors have shown that the expression of two polypeptides, EthB and EthD, is induced upon growth on ETBE (Examples 1 and 5 below). This demonstrates that the promoter of the eth cluster is inducible by ETBE. Therefore, a bacterium comprising a transcriptional fusion between the eth cluster (involving at least the eth promoter and ethR), and a reporter gene can be used for the detection of a pollution by ETBE. The reporter gene can code for any reporter protein known in the art, for example a bioluminescent protein such as luciferase, or an enzyme such as peroxydase or beta-galactosidase, and the means to reveal the expression of said reporter gene are known by the skilled artisan.

A bacterium as described in the preceding paragraph can be used in a process for detecting a contamination by an ether fuel additive such as ETBE in an aqueous effluent, a soil, a sludge, a sediment, a dredge tailing, a gas or a chemical waste, comprising the step of contacting said aqueous effluent, soil, sludge, sediment, dredge tailing, gas or chemical waste with said bacterium. This process is also part of the present invention, as well as a microbial whole cell biosensor comprising a bacterium as described in the above paragraph, for detecting the presence of a contamination by an ether fuel additive, such as ETBE, in a complex mixture.

Another aspect of the present invention is a process for depolluting an aqueous effluent, a soil, a sludge, a sediment, a dredge tailing, a gas or a chemical waste contaminated with an ether fuel such as ETBE, comprising the step of contacting said effluent, soil, sludge, sediment, dredge tailing, gas or chemical waste with a bacterium able to degrade at least said ether fuel, as described above. In a preferred embodiment, said bacterium able to degrade the ether fuel is a recombinant bacterium bearing all or part of the eth gene cluster. In another preferred embodiment, said bacterium able to degrade the ether fuel is a bacterium which has been identified by a method as described above.

In one embodiment of this process of the invention, the depollution takes place in a bioreactor. A variety of bioreactors known to those of skill in the art may be used in the practice of the present invention. Suspended growth reactors, such as membrane bioreactors, standard continuously stirred tank reactors (CSTRs) and activated sludge systems may be used in the practice of the invention. Alternatively, and because bacteria adhere strongly to surfaces, fixed film reactors, such as fluidized bed reactors or fixed support reactors, may also be used, if desired.

In another embodiment of the depollution process of the invention, the depollution takes place in situ, by addition of recombinant bacteria capable of cleaving ether fuel additives as described above to the contaminated medium. In this case, the bacteria can further contain a susceptibility gene that prevents their uncontrolled spread in the environment, by addition of a product that will kill them selectively when they are not necessary anymore.

Alternative or complementarily, the bacteria can be confined in biobarriers, biofilters, and/or biopiles. Such biobarriers, biofilters, and biopiles are commonly used by the skilled artisan to prevent the spreading of a pollution, for example when disposed between the pollution source and ground water located downstream of said pollution.

The present invention includes also within its scope the use of one or more microorganisms in combination with one or more of the microorganisms described herein to achieve complementary degradation against a mixture of contaminants which includes an ether, for example, in the treatment of mixed waste streams. Such a combination utilizes the different degradative specificities of the involved microorganisms. Accordingly, for certain applications, a given contaminated medium may be treated with microorganisms having different specificities for given contaminants or their degradative intermediates.

Other characteristics of the invention will also become apparent in the course of the description which follows of the biological assays which have been performed in the framework of the invention and which provide it with the required experimental support, without limiting its scope.

LEGENDS TO THE FIGURES

FIG. 1. 10-15%-polyacrylamide gradient gel electrophoresis containing SDS. *R. ruber* crude extracts of wild type (I-1889 designated as IFP 2001) and the constitutive mutant (I-2194 designated as IFP 2007) were analysed after growth in the presence of ethanol (EtOH) or ETBE as the sole source of carbon. The migration of molecular size markers (in kDa) is indicated on the right.

Figure 2:
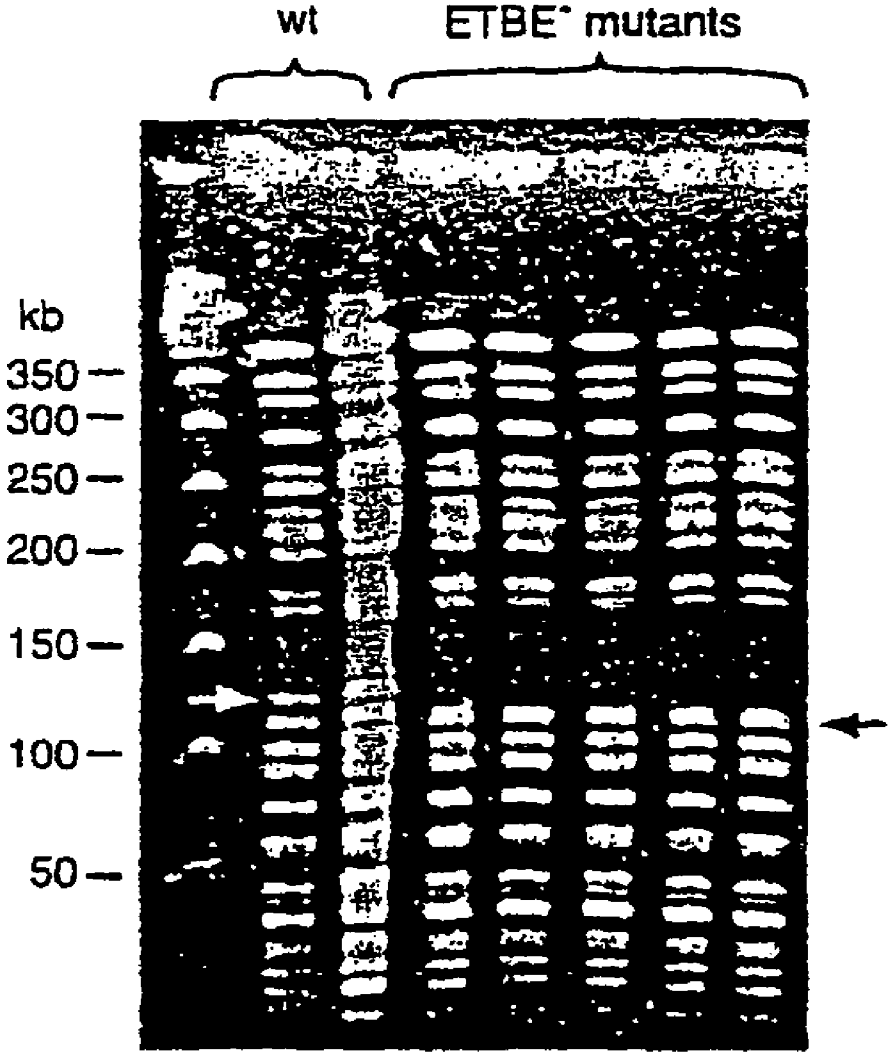

FIG. 2. Pulsed-field gel electrophoresis of XbaI-digested chromosomal DNA from wild type (I-1889) and ETBE-negative mutants of *R. ruber*. The arrows designate the 125-kb band of the wild type strain and the 110-kb band of the mutants. The migration of the 50-kb concatemers of lambda DNA (sold by Biolabs) is indicated on the left.

Figure 3:
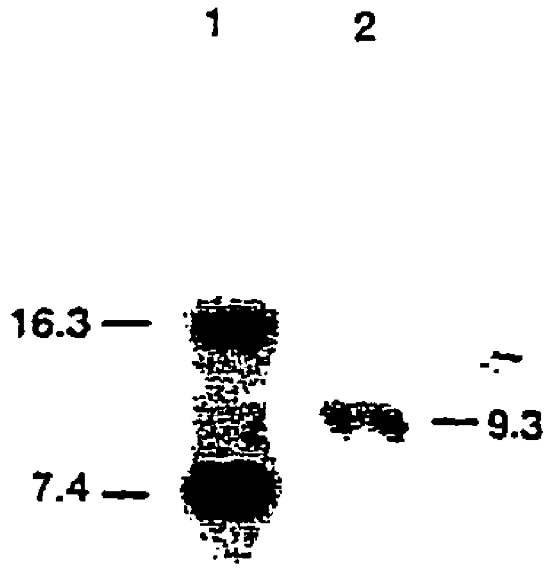

FIG. 3. Southern blot hybridization of BamHI-digested chromosomal DNA from the wild type strain (1) and an ETBE-negative mutant (2), using the BamHI-fragment of 7.4 kbp as a probe. The size of hybridizing bands is indicated in kbp.

Figure 4:
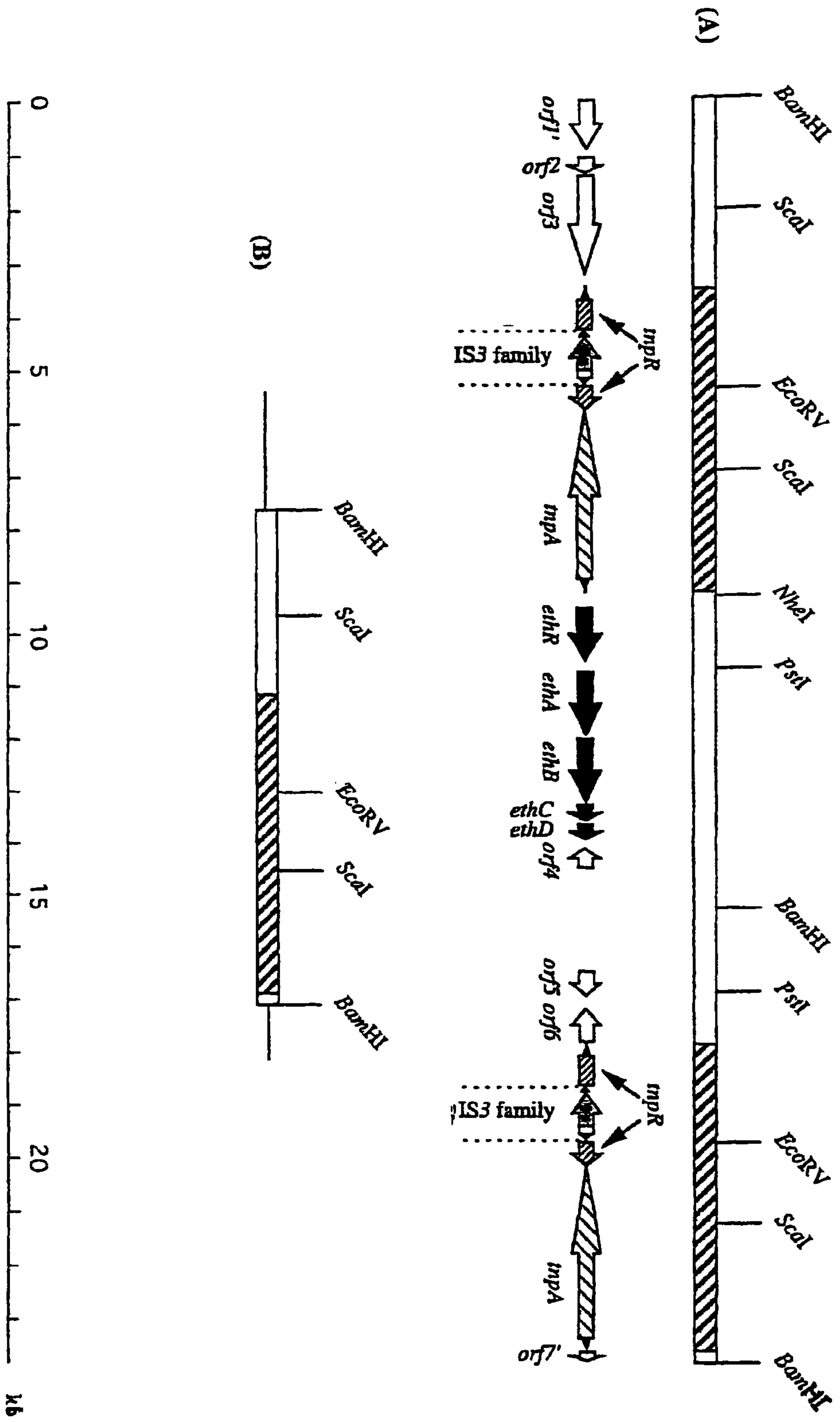

FIG. 4. Wild type genetic organization of the 23.7 kbp region carrying the genes involved in the ETBE degradation (A) and restriction map of the 9.3-kbp BamHI fragment of the ETBE-negative mutant (B). The eth genes encode a transcriptional activator (EthR), a ferredoxin reductase (EthA), the ETBE-inducible cytochrome P450 (EthB), a ferredoxin (EthC) and an ETBE-inducible unknown protein (EthD). The other open reading frames shown correspond to a resolvase (TnpR), transposase (TnpA), two-component system response regulator (truncated Orf1'), integral membrane protein (Orf2), sodium:solute symporter (Orf3), membrane protein (truncated Orf7') and three unidentified proteins (Orf4, Orf5 and Orf6).

Figure 5:
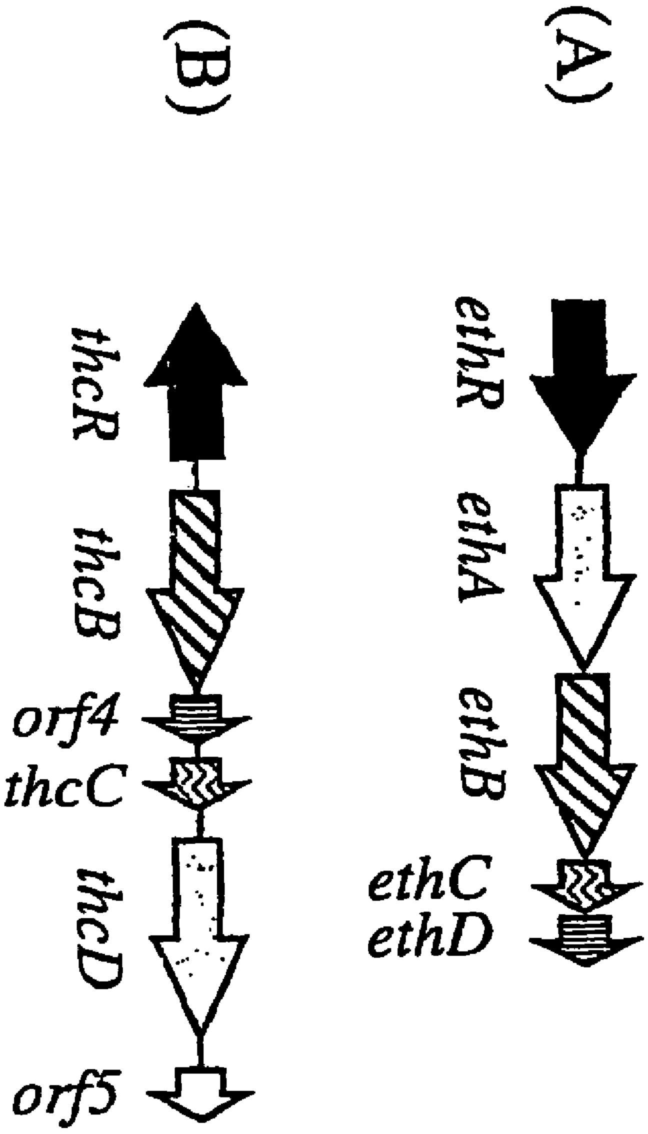

FIG. 5. Genetic organization of *R. ruber* (A) and *R. erythropolis* (B) (28) cytochrome P-450 systems. Transcriptional activators ■, cytochromes P-450 ▨, ferredoxin reductases ☐, ferredoxins ▦ and unknown proteins ▦ are 31%, 24%, 47%, 48% and 40% identical, respectively.

Figure 6:
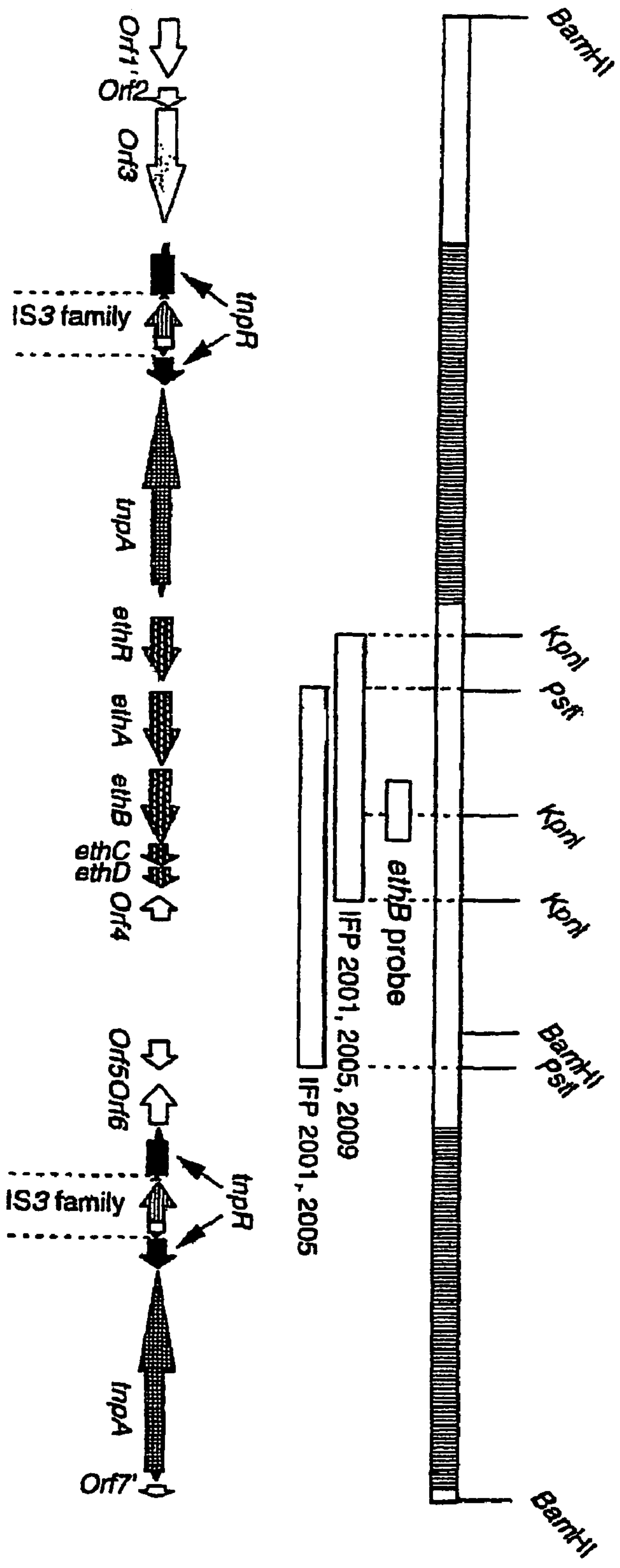

FIG. 6. Regions of the genomes of strains of *R. ruber* I-1889, *R. zopfii* I-2053, and *Mycobacterium* sp IFP 2009 probably sharing high similarity. The position of the *R. ruber* ethB probe is shown by a white rectangle. Genomic fragments of similar size hybridising to the ethB probe in *R. ruber* I-1889 and in the other strains tested are shown by black rectangles.

EXAMPLES

The following examples can be performed using the materials and methods described below:

Materials and Methods

Bacterial strains and culture conditions. *R. ruber* I-1889, or I-2194, was grown at 30° C. in Luria-Bertani (LB) medium, or in minimum medium MM1 which contained 50 mM $KH_2PO_4$, 50 mM $K_2HPO_4$, 0.16 mM $MgSO_4$, 1.9 mM $Na_2HPO_4$, 28 mM $NH_4Cl$, 0.27 mM $CaCl_2$, 4.4 µM $FeCl_3$, 200 µg/l biotine, 50 µg/l riboflavine, 50 µg/l nicotinic acid, 50 µg/l calcium panthotenate, 50 µg/l p-aminobenzoic acid, 20 µg/l folic acid, 15 µg/l thiamine hydrochoride, 1.5 µg/l cyanocobalamine, with 200 mgA ETBE (Aldrich Chemical Co.), or 0.5% ethanol as the sole carbon source. Cultivation on solid medium using ETBE as a carbon source was performed in glass Petri dishes containing MM1 medium with 1.5% agar. ETBE was supplied in the gas phase by a piece of filter paper stuck to the lid of the dish, which was wetted with 200 µl ETBE. Plates were sealed with polythene food wrap. *Escherichia coli* TG1 was grown at 37° C. in LB.

Isolation of spontaneous mutants unable to degrade ETBE. *R. ruber* was plated on MM1 agar with ETBE vapor as the carbon source, and independent clones were transferred to liquid LB medium. After growth to saturation, clones were diluted into fresh LB medium and the procedure was repeated for 60 generations. Cultures were then plated on LB plates, and individual colonies were patched on LB plates and ETBE-containing MM1 plates, including wild type controls. After 8-10 days, clones showing markedly reduced growth on ETBE plates were selected. TBA production was assayed in cell free culture supernatants using a Peri-2000 gas chromatograph (Perichronn) fitted with a 3m FFAP column.

Pulsed-field gel electrophoresis. *R. ruber* was grown in 40 ml LB until $D.O._{600}$=1. Cells were then centrifuged, resuspended in 20 ml 1% (v/v) Triton X-100 and incubated for 2 h at 37° C. Cells were centrifuged again, washed in 0.05 M EDTA and resuspended in 1 ml 10 mM Tris-HCl pH8, 100 mM EDTA containing 1 mg/ml lysozyme. The suspension was then mixed with an equal volume of 1% (w/v) low-melting-point agarose and dispensed in a slot former of 60 µl. Plugs were iricubated in 0.5 M EDTA for 24 h at 37° C., then washed in TE and incubated in 1% (w/v) sodium N-lauroyl-sarcosinate (Fluka) and 2 mg/ml proteinase K for an extra night at 55° C. Plugs were washed in TE and incubated in TE containing 4 µg/ml phenylmethylsulfonyl fluoride (Sigma Chemical co.) for 1 h at 55° C. to inactivate proteinase K. Finally, plugs were extensively washed in TE and digested with 3 U/ml XbaI. After digestion, plugs were loaded in 1% (w/v) agarose gel. PFGE was performed in a contour-clamped homogeneous electric field (CHEF) apparatus (Bio-Rad, Munich, Germany), in which the electrode distribution was arranged such that the reorientation angle of DNA molecules was 120° C. Large restriction fragments were separated at 14° C. with a pulse ramp of 1.6 to 21.3 sec for 23 h.

Chromosomal DNA extraction. 400 ml of a *R. ruber* culture at $D.O._{600}$~1.3 was harvested 15 min at 5.000×g. Cells were resuspended in 15 ml of 0.1 M Tris-HCl pH 8, 0.1 M EDTA, 0.15 M NaCl (TEN) supplemented with 150 μl of Triton X100 and 100 mg of lysozyme, and incubated overnight at 37° C. with agitation. The lysate was further incubated 1 h at 60° C. in the presence of 1.3 mg/ml RNAse A, followed by treatment with 0.6 mg/ml proteinase K and 2% SDS at 40° C. for 2 h. Chromosomal DNA was extracted with phenol and with chloroform. Precipitation was performed with 1/10 volume of 1 M NaCl and 2 volumes of ethanol. About 800 μg DNA was recovered by hooking it on the end of a Pasteur pipet and was resuspended in TEN.

Construction of genomic libraries and colony screening. Chromosomal DNA was digested with BamHI and fragments of the appropriate size were electroeluted from an agarose gel. Cloning was carried out using pUC18 (37) linearized with BamHI, treated with bacterial alkaline phosphatase and formulated with T4 DNA ligase (Ready-To-Go from Amersham-Pharmacia-Biotech). *E. coli* was transformed by electroporation and plated in the presence of 100 μg/ml ticarcillin. Colonies of recombinant clones were transferred to Nylon filters (Hybond-N+; Amersham-Pharmacia-Biotech). Filters were placed colony side up in all the following operations. Cell lysis was performed by placing the filters on an absorbent filter paper soaked in 2×SSC (0.3 M NaCl, 0.03 M sodium citrate), 5% SDS and incubating for 10 min. Membranes were then transferred to dry filter paper. DNA fixation and denaturation were carried out by exposure to 650 watts microwaves for 2 min. Filters were washed in 5×SSC, 0.1% SDS at 65° C. for 30 min. Lysate left on the surface of the filters was scratched up with a gloved finger. Membranes were rinsed in 2×SSC and transferred to dry filter paper. Hybridizations of DNA probes proceeded in Rapid-Hyb buffer (Amersham-Pharmacia-Biotech) from 2 h to overnight incubations at 65° C. Unspecific hybridizations were removed by washing the membranes twice in 1×SSC, 0.1% SDS at 65° C. for 30 min.

Preparation of DNA probes. DNA fragments were purified from agarose gels using the QIAquick gel extraction kit (Qiagen). DNA was labelled with [$^{32}$P]dCTP using the random prime labelling system (rediprime II, Amersham-Pharmacia-Biotech). Labelled DNA was purified from unincorporated nucleotides using a Sephadex G-50 column (Nick Columns, Amersham-Pharmacia-Biotech).

DNA sequencing. The plasmids pGT200 and pGT220 obtained by the construction of genome libraries as described above and containing 7.4- and 16.3-kbp inserts respectively, were used as starting material to construct a small-insert library. The plasmids were fragmented by nebulization and gel-purified fragments in the range of 1-2 kbp were cloned in the pcDNA2.1 vector using the non-palindromic cloning method as described before (12). The inserts of randomly chosen clones of the small-insert library were sequenced from both ends using a Perkin Elmer automated sequencer ABI 3700. The sequences were assembled using the Phred, Phrap and Consed software tools (9, 10). During the assembly process, the presence of a repeated sequence of 5.6 kbp was noticed. The sequences of the repeats have been checked again by resequencing using the individual plasmids, pGT200 and pGT220, as templates. One copy of the repeat is located in pGT200 and the second copy in pGT220. As expected, two contigs corresponding to the 7.4 and 16.3 inserts of pGT200 and pGT220 were obtained. A PCR reaction using gt1 (5'-ACCCCCGCMTCGTCGGC-3') (SEQ ID No: 15) and gt2 (5'-TGCCGGCGGCTCCGCTGA-3') (SEQ ID No: 16) as primers resulted in the amplification of a product overlapping the gap between the two configs. Finally, the complete sequence was obtained as a single contig of 23,696 bases.

Crude extracts preparation and analysis. *R. ruber* cells in exponential phase growth were harvested 15 min at 5.000×g. Pellets were resuspended in 50 mM Tris pH 7.5 and cells were disrupted three times through a prechilled French pressure cell at 200 MPa (SLM-Aminco). Cell debris were removed by centrifugation at 27.000×g for 15 min. Total proteins of the supernatant were assayed with the Coomassie blue reagent (Bio-Rad) and analyzed by a denaturing 10-15%-polyacrylamide gradient gel electrophoresis.

Peptide sequencing of two ETBE-induced proteins. Crude extracts of ETBE-induced *R. ruber* were centrifuged 1 h at 100.000×g and the supernatant was subjected to SDS-polyacrylamide gel electrophoresis. A major ETBE-induced band of 43 kDa was cut out from a Tris-glycine gel containing 7.5% polyacrylamide, and aminor ETBE-induced band of 10 kDa was cut out from a Tris-tricine gel containing 20% polyacrylamide. The bands were subsequently digested with trypsin and peptides were separated by DEAE-$C_{18}$ reverse-phase chromatography using a water/acetonitrile gradient in the presence of 0.1% trifluoroacetic acid. Selected peptides were sequenced by the Edman method, using a model 473 A sequencer (Applied Biosystems).

Example 1

Identification of *Rhodococcus ruber* Proteins Induced in the Presence of ETBE FIG. 1 shows an SDS-polyacrylamide gel analysis of crude extracts prepared from *R. ruber* cells grown on ethanol and on ETBE. Two polypeptides of 43 and 10 kDa were clearly induced in the wild type upon growth on ETBE. They were also present, although less abundant, in cells of a previously isolated constitutive mutant I-2194 (18). Peptide microsequencing yielded the partial sequences HALGDWQTFSSAQGI (SEQ ID NO:17), FDSVAQWFTR (SEQ ID NO:18), and SVSNTEMIALWTELG (SEQ ID NO:19) for the 43-kDa protein and GQPTDTEAFDTYYS (SEQ ID NO:20) for the 10-kDa protein. The first sequence, HALGDWQTFSSAQGI (SEQ ID NO:21), was 66% identical to a putative cytochrome P-450 from *Mycobacterium tuberculosis* H37Rv (Genpept Z177137_5), suggesting that the 43-kDa polypeptide may be the inducible cytochrome P450 observed in ETBE-grown *G terrae* cells by Hernandez-Perez et al. (18). The GQPTDTEAFDTYYS (SEQ ID NO:20) sequence was 47% identical to Orf4 from *Rhodococcus erythropolis* (Genpept U17130_4). The *R. erythropolis* orf4 gene is part of a cytochrome P-450 gene cluster suggesting that the inducible 10-kDa polypeptide is related to a cytochrome P-450 system. None of the two other sequences showed significant similarity with any of characterized proteins present in the databases.

Example 2

Isolation of Independent ETBE-negative Mutants

In an attempt to verify the stability of the ETBE-positive phenotype, five independant clones of *R. ruber* were cultivated in LB broth for 60 generations. Then, cultures were screened for the presence of mutants unable to grow in the presence of ETBE as the sole source of energy and carbon. Twenty to 100% of the clones tested were found unable to degrade ETBE. Five independent mutants, derived from the five original wild type clones, were further characterized. When grown to saturation in minimal medium containing 0,5% glucose and 18 mM ETBE, none of the mutants converted more than 0.3 mM ETBE into TBA, whereas under the same conditions, 10.6 mM TBA was produced by the wild type. The reversion to the $ETBE^+$ phenotype was not detectable (no positive colony out of at least $3\times10^7$ viable cells plated), suggesting the occurrence of an irreversible genetic rearrangement. Wild type and mutants strains were compared after growth in the presence of 0.5% glucose +18 mM ETBE. Analysis of crude extracts showed that, in contrast to the wild type, none of the mutants produced the induced 43 and 10 kDa proteins. Likewise, mutant resting cells lost the ability to degrade MTBE and TAME.

Example 3

Evidence for a 15-kbp Chromosomal Deletion in ETBE-negative Mutants

XbaI-genomic digests of wild type and mutant strains were analyzed by pulsed-field gel electrophoresis (FIG. 2). A 125-kbp fragment was present in the wild type strain and was absent in the ETBE-negative mutants. In addition, a 110-kbp fragment was observed in the ETBE-negative mutants only. Southern blot hybridization revealed that the wild-type 125-kbp fragment used as a probe hybridized with the mutant 110-kpb fragment, showing that the 110-kpb fragment was a deleted form of the 125-kbp fragment. This result indicated that ETBE-negative mutants resulted from a 15-kbp chromosomal deletion. Since all independant mutants showed the same genotype, a single mutant was used for further investigation.

Example 4

Cloning of the Wild Type DNA Region Corresponding to the Deletion

The wild-type XbaI-fragment of 125 kbp was purified from a pulsed-field gel electrophoresis gel and was used as a probe in Southern-blot analysis. Hybridization of the 125-kb XbaI probe with BamHI-genomic digests showed that a 7.4-kbp band and a 16.3-kbp band, present in the wild type strain, disappeared in the ETBE-negative mutant. Conversely, a new 9.3-kbp band, which was absent in the wild type strain, was detected in the ETBE-negative mutant. This demonstrated that the 15-kbp deletion identified by pulsed-field gel electrophoresis involved the two BamHI-fragments of 7.4 and 16.3 kbp which were reshuffled into a new BamHI-fragment of 9.3 kbp. In order to determine the sequence of the region corresponding to the deletion, the two wild-type BamHI-fragments of 7.4 kbp and 16.3 kbp were cloned. The 7.4-kbp BamHI fragment was selected by colony hybridization using the 125-kbp XbaI fragment as a probe. The cloned 7.4-kbp fragment was then used as a probe in a Southern blot hybridization (FIG. 3). In addition to self hybridization, the 7.4-kb BamHI probe also hybridized with the 16.3-kbp BamHI fragment of the wild type and with the 9.3-kbp BamHI fragment of the ETBE-negative mutant. This indicated that the wild-type 7.4-kbp fragment carried a sequence that was also present in these two fragments. Thus, the wild type 16.3-kbp BamHI fragment and the mutant 9.3-kbp BamHI fragment were cloned by colony hybridization using the 7.4-kb BamHI fragment as a probe.

Example 5 ethA,B,C,D Code for a Cytochrome P-450 System

The features of the 23.7-kbp region covered by the two wild-type BamHI fragments are shown in FIG. 4. A cluster of four open reading frames with the same orientation and named ethA, B, C, D were identified. Based on protein alignments, ethA, B and C could be assigned to individual components of a P-450 system containing monooxygenase.

EthA (412 amino acids) is similar to glutathione reductase-like ferredoxin reductases. It contains amino acids typical of two ADP-binding βαβ folds which encompass the completely conserved consensus motif GXGXXG (SEQ ID NO:22) (36). The N-terminal ADP-binding site (Val-1 to Asp-31) may constitute the FAD-binding site and the centrally-located ADP-binding site (Arg-144 to Asp-172) may constitute the NAD-binding site.

EthB (400 amino acids) corresponds to the ETBE-induced protein of 43 kDa, since it contains the three peptides that were sequenced. In addition, EthB is similar to cytochromes P-450, which suggests that EthB is the cytochrome P-450 catalyzing the oxidation of ETBE. EthB carries a cysteine residue at position 349, which is strictly conserved in all cytochromes P-450. This residue is part of the consensus FGXGXHXCXG (SEQ ID NO:23) and possibly provides anchoring of the heme in the active site of the cytochrome P-450. The highest similarity score of EthB (33% identity) was found with a putative cytochrome P-450 from the phenanthrene-degrading actinomycete *Nocardioides* sp. (22). Among the characterized cytochromes P-450, EthB shows highest similarity (25% identity) to the *Pseudomonas* sp. cytochrome P-450terp, which hydroxylates the monoterpene α-terpineol as a step in the process of its catabolic assimilation (29). Two actinomycetal cytochromes P-450 also show 25% identity to EthB: NikQ from the antibiotic nikkomycin-producing *Streptomyces tendae* (24) and Orf3 from the drug mitomycin C-producing *Streptomyces lavendulae* (25).

EthC (106 amino acids) is a putidaredoxin-type [2Fe-2S] ferredoxin which probably serves as an electron carrier between the NADH-dependent ferredoxin reductase (EthA) and the cytochrome P-450 (EthB). The four cysteine residues located at positions 40, 46, 49 and 76 of EthC correspond to the perfectly conserved residues that are required for coordinating the prosthetic group.

EthD (103 amino acids) corresponds to the ETBE-induced protein of 10 kDa, since it carries the sequenced peptide. EthD is similar to three Orfs of unknown function: OrfY from *Pseudonocardia* sp. (Genpept AJ296087_1), an Orf from *Bacillus halodurans* (Genpept AP001507_200) and Orf4 from *Rhodococcus erythropolis* (Genpept U17130_4), which are 40, 34 and 40% identical to EthD, respectively. *R. erythropolis* off4 belongs to the the gene cluster which encodes a cytochrome P450 system catalyzing the N-dealkylation of thiocarbamates (28). In addition to orf4, the the cluster contains genes homologous to the eth genes of *R. ruber*. The thcB gene encodes a cytochrome P-450 showing 24% identity to EthB. The thcC and thcD genes encode a ferredoxin (named rhodocoxin) and a ferredoxin reductase, respectively, which are the closest relatives to EthC (48% identity) and EthA (47% identity), respectively (FIG. 5).

Example 6 ethR Encodes a Transcriptional Regulator of the AraC/XylS Family

The ethR gene lies 183 bp upstream of ethA (FIG. 4). EthR (331 amino acids) is highly similar to positive transcriptional regulators of the AraC/XylS family. The highly conserved C-terminal domain of regulators of the AraC/XylS family is comprised between amino acids 250 and 325 of EthR (13). As expected, a putative DNA-binding motif was found in EthR between residues 244 and 265 using the method of Dodd and Egan (7). The most closely related member is *R. erythropolis* ThcR which is 31% identical to EthR (28). In addition, ThcR is the only member of the AraC/XylS family which shows significant similarity with EthR outside the conserved C-terminal domain of the family. The thcR gene is located upstream of the putative operon encoding the cytochrome P-450 system involved in the N-dealkylation of thiocarbamates.

Example 7

Transposon Repeats Flanking eth Genes

Two directly identical sequences of 5.6 kbp flank the eth genes (FIG. 4). The first repeat ends 880 bp upstream of ethR and the second repeat starts 3.908 bp downstream of ethD. Three potential coding regions (orf4, orf5 and orf6) were identified in the 3.908 bp region using the Heuristic approach of the GeneMark program (3). Amino acid comparison of Orf4, Orf5 and Orf6 using the blast program did not show any significant similarity with the bacterial Genpept database (1).

The 5.6-kbp repeat consists of a class-II transposon containing a terminal inverted repeat of 38 bp, a tnpA gene encoding a putative transposase, and an IS-interrupted tnpR gene. Discounting the entire IS sequence, the intact tnpR gene may encode a putative resolvase of 311 amino acids. The TnpA (1008 amino acids) and TnpR (311 amino acids) proteins show very high amino acid similarity to TnpA and Orf5, respectively, of the *Streptomyces fradiae* Tn4556 transposon (34). The TnpA transposase of *S. fradiae* is the closest relative of *G. terrae* TnpA with 49% of identity. Orf5 of *S. fradiae* Tn4556 is a potential resolvase of Tn4556 whose similarity with *R. ruber* TnpR extends into the upstream region of this Orf, disregarding a TAG stop codon as mentioned by De Mot et al. (6). The deduced polypeptide of 324 residues is 31% identical to TnpR of *R. ruber*. The closest relative of *R. ruber* TnpR is *Rhodococcus erythropolis* PmrA (62% identity), which is a site-specific recombinase of the integrase family and may be involved in stabilization of the cryptic plasmid pFAJ2600 (6). Amino acid comparisons revealed that other proteins related to *R. ruber* TnpR are almost exclusively site-specific recombinases of the integrase family. This suggests that, unlike most resolvases of class-II transposons, TnpR belongs to the integrase family and not to the resolvase-invertase family of site-specific recombinases.

The region coding for TnpR is interrupted by an insertion of 1409 bp at codon 180, introducing a stop codon at position 181. This 1409-bp insertion displays all structural characteristics of mobile elements of the IS3 family. Imperfect 45-bp inverted repeats flank a single open reading frame with a translational frameshift. The predicted protein is 420 amino acid long and shows extended similarity to several transposases of the IS3 family. The most closely related is the transposase of *Mycobacterium avium* IS999 (Genpept AF232829_2) which is 40% identical to the IS3type transposase of *R. ruber*. The region coding for the *R. ruber* transposase of 420 amino acids overlaps two open reading frames in phase 0 and −1 encoding, respectively, the N-terminal (108 amino acids) and the C-terminal (312 amino acids) regions of the potential transposase. Like for other members of IS3 family, the translational frameshift may be a means of producing several proteins using the same coding region (5).

Example 8

Genetic Rearrangement Promoting ETBE-negative Mutants

To elucidate the molecular mechanism responsible for the 14.3-kbp deletion, we cloned the 9.3-kbp BamHI fragment which is specific of ETBE-negative mutants. The genetic organization of the 9.3-kbp BamHI fragment was determined by sequencing each end of the fragment (68 and 452 nucleotides, respectively) and by restriction analysis (FIG. 4). The 9.3-kbp BamHI fragment corresponds to the wild type 23.7 kbp region deleted for one copy of the 5.6-kbp transposon and for the intergenic region between the two copies of the transposon. This deletion encompasses the eth gene cluster which is involved in ETBE degradation. Thus, the genetic organizations of the wild type and ETBE-negative mutants sugg st that spontaneous loss of the ability to degrade ETBE results from an homologous recombination between the two identical direct repeats of the 5.6-kbp transposon.

Example 9

Evidence that the Genes Located Between the Two Transposon-like Sequences Participate in the Cleavage of MTBE and tert-amyl Methyl Ether (TAME)

*Rhodococcus ruber* I-1889 is able to degrade MTBE and tert-amyl methyl ether (TAME) to TBA and tert-amyl alcohol (TAA) when the ethers are added together with a substrate allowing growth as a carbon source (ref. 18: Hernandez-Pérez, Fayolle & Vandecasteele). In order to investigate whether the enzyme system responsible for the cleavage of ETBE was also involved in the cleavage of MTBE and TAME, the degrading activities of wild type and mutant resting cells grown to late log phase in mineral medium containing 0.5% glucose and 18 mM ETBE were compared. Activities were determined by measuring the release of TBA or TM, respectively. TBA and TM were assayed by gas chromatography using a Peri 2000 chromatograph (Perichrom) equipped with a 3 m10% FFAP/Chromosorb 80-100 mesh and a flame ionization detector. The wild type cells had a specific activity of 31.9, 20.5 and 33;4 pmole $min^{-1}$ $O.D._{600}^{-1}$ against ETBE, MTBE and TAME respectively. The specific activity of the mutant strain was less than 1 pmole $min^{-1}$ $O.D._{600}^{-1}$, showing that the genes present in the deleted segment were required for the degradation of the three substrates.

Example 10

Evidence that Other ETBE-degrading Bacteria Possess Highly Similar Cytochrome P-450 Systems, which can be Amplified by PCR Using Primers Derived from the Sequence of ethB Two other ETBE-degrading bacteria, *Rhodococcus zopfii* deposited at CNCM on Jul. 20, 1998, under the accession number I-2053 and *Gordonia* sp. IFP 2009, were tested for the presence of cytochrome P-450 systems similar to that encoded by ethRABCD gene cluster of *R. ruber* I-1889. Whole genomic DNA was extracted from *Rhodococcus zopfii* I-2053 and *Gordonia* sp. IFP 2009 as described above and used in PCR reactions primed with the oligonucleotides CAY GCI YTI GAY TGG CAG ACS TT (SEQ ID NO:24) and TCI GTC CAI AGI GCK ATC ATY TCI GTG TT (SEQ ID NO:25) (I=inosine, Y=T or C, S=G or C, K=G or T). These correspond to positions 12216-12241 and 13107-13135, respectively, of the sequence SEQ ID NO:1. The expected DNA segment corresponds to the region encoding residues 59 to 365 of the *R. ruber* cytochrome P-450 polypeptide. Reaction mixtures contained 100 pmole of each primer, 50-100 ng of template DNA, 400 pM of each dNTP, and 2.5 units of LaTaq™ DNA polymerase (Takara Biomedicals) in 50 μl GC buffer I (supplied by the manufacturer with DNA polymerase). The PCR cycler program was as follows: 4 min at 94° C., followed by 35 cycles: 1 min at 94° C., 1 min at 65° C., 1 min at 72° C. In either case, a 919 bp fragment was obtained, cloned into the pCR® 2.1-TOPO® vector supplied with the TOPO TA cloning kit (Invitrogen), and sequenced. For both .*R. zopfii* I-2053 and *Gordonia* sp. IFP 2009, the sequence of the DNA amplified by the primers derived from *R. ruber* ethB was at least 98% identical with that of the corresponding region in *R. ruber* I-1889.

Furthermore, the DNA segment amplified from *R. ruber* I-1889 was labelled and used as a probe against Southern blots of *R. ruber* I-1889, *R. zopfii* I-2053 and *Mycobacterium* sp. IFP 2009 digested with various restriction enzymes. As shown in FIG. 6, in the three strains, the prob hybridised to a 3 kb KpnI fragment covering the ethABCD genes and part of the ethR gene of *R. ruber* I-1889. In addition, *R. ruber* I-1889 and *R. zopfii* I-2053 shared a common 6.1 kb PstI fragment hybridising to the ethB probe, which was not observed in *Mycobacterium* sp. IFP 2009.

These results show that the ethB gene is highly conserved in several bacterial species possessing the ability to degrade ETBE, and that its presence can be adequately demonstrated by PCR using appropriate primers. They suggest that sequence similarity extends to the whole ethRABCD gene cluster. The region extending downstream of the cluster may be more conserved in *R. ruber* I-1889 and *R. zopfii* I-2053 than in *Mycobacterium* sp. IFP 2009, since the size of the PstI fragment hybridising to the ethB probe is not conserved in the latter.

In particular, PCR fragments corresponding to residues 3630-5448, 3630-9030, 6200-9030, 8969-9581, 9557-14157, 13471-16291, and 16291-17998 of SEQ ID n° 1 were labelled and used as probes against Southern blots of genomic DNA from *R. ruber* I-1889 and *R. zopfii* I-2053 digested with various enzymes. With BcA, ClaI, KpnI, PvuII, PstI, SmaI and SphI, the sizes of hybridizing *R. zopfii* I-2053 fragments matched those observed for *R. tuber* I-1889 DNA for all of the region extending between the 5' end of the first transposon-like repeat and the 3' end of the second repeat. This indicates that in both organisms, the ethRABCD genes are highly conserved and are similarly flanked by the same transposon-like repeats. However, sequencing of the distal end of the first transposon-like repeat in *R. zopfii* I-2053 showed that the sequence identity ended abruptly at the border of the repeat, indicating that the locus composed of the ethRABCD genes and the two flanking transposons was inserted in a different context.

Similar blotting experiments performed with *Mycobacterium* sp. IFP 2009 showed that the restriction map of the region corresponding to the ethRABCD genes was identical to that of *R. ruber* I-1889 with respect to ApaI, BclI, BglII, KpnI, NruI, PvuII, SmaI, SphI and StyI sites. However, no copy of the transposon was found immediately upstream of the ethRABCD gene cluster of *Mycobacterium* sp. IFP 2009 and the similarity with the *R. ruber* I-1889 sequence ended upstream of residue 9243 of SEQ ID N° 1. A copy of the transposon hybridizing to the *R. ruber* transposon-derived probes and showing the same restriction sites was found downstream of the ethRABCD gene cluster. However, it was found by sequencing that the transposon was inserted 2771 residues closer to the ethRABCD cluster (beginning of the transposon sequence at residue 15090 instead of 17861).

Example 11

Evidence that in Other Bacterial Species Degrading ETBE, the Genes Encoding the Cytochrome P-450 System are Flanked by Duplicated Transposon-like Sequences Similar to Those Present in *R. ruber* I-1889

Individual clones of *R. zopfii* I-2053 and *Mycobacterium* sp. IFP 2009 were grown to saturation in Luria broth and subcultured for 35 generations in the same medium. The cultures were then screened for the presence of variants no longer able to utilize ETBE as a carbon source, as described for *R. ruber* I-1889. In both cases, segregants no longer able to grow on ETBE were obtained with a frequency greater than 50%. Genomic DNA was extracted from wild type and mutant strains for both species and subjected to Southern analysis using the probe derived from ethB (see above) or a probe derived from the duplicated transposon flanking the ethRABCD cluster in *R. ruber* I-1889. The latter was obtained by PCR amplification of the region comprising nucleotides 3630 to 9030 of the sequence SEQ ID N° 1. For both species, strains no longer able to degrade ETBE failed to hybridize to the ethB probe, in contrast to the wild type strains (see above). When hybridization was performed with the transposon probe, two fragments were revealed in the wild type strains, but only one in the mutant strains. These observations suggest that in *R. zopfii* I-2053 and in *Mycobacterium* sp. IFP 2009, the ethRABCD gene cluster is flanked by duplicated transposon-like sequences similar to those found in *R. ruber* I-1889. This leads in the same manner to the instability of the genes responsible for the ETBE-degrading phenotype, which are lost upon recombination between the duplicated regions.

Example 12

Complementation of the *R. ruber* Mutant by the ethRABCD Gene Cluster

The NheI-SacI DNA segment located between nucleotides 9328 and 14253 was recloned between the XbaI and SacI sites of the pRE-7 vector (ref. Zheng, H., Tkachuk, O. & Prescott, J. F. 1997. Development of a *Rhodococcus* equi-*Escherchia coli* plasmid shuffle vector. Plasmid 38, 180-187). The recombinant plasmid, termed pGT222, was reintroduced into the strain of *R. ruber* harbouring the spontaneous deletion described above. Transformants were selected on LB containing 100 μg/ml kanamycin. One of the *R. ruber* transformants was shown to recover the ability to grow using ETBE as a carbon source. This indicates that the region located downstream from the ethRABCD cluster is not required for ETBE utilization.

Example 13

Functional Expression of *R. ruber* ethRABCD Gene Cluster in *Mycobacterium smegmatis*

The 4,923-bp NheI-SacI fragment carrying ethRABCD of *Rhodococcus ruber* I-1889 described in Example 12 was cloned into the pCL4D plasmid (38), generating pMS100. The pMS100 plasmid was introduced into *Mycobacterium smegmatis* and shown to confer on *M. smegmatis* the ability to grow on ETBE.

REFERENCES

1. Altschul, S. F., Madden, T. L., Schaffer, A. A., Zhang, J., Zhang, Z., Miller, W. and Lipman, D. J. 1997. Gapped blast and psi-blast: a new generation of protein database search programs. Nucleic Acids Res. 25. 3389-3402.
2. Ausubel, F. M., Brent, R., Kingston, R. E., Moore, D. D., Seidman, J. G., Smith, J. A. and Struhl, K. 1990. Current Protocols in Molecular Biology. Greene Publishing and Wiley Interscience, New York.
3. Besemer, J. and Borodovsky, M. 1999. Heuristic approach to deriving models for gene finding. Nucleic Acids Res. 27. 3911-3920.
4. Brown, S. L. 1997. Atmospheric and potable water exposures to methyl tert-butyl ether (MTBE). Regul. Toxicol. Pharmacol. 25.256-276.
5. Chandler, M. and Fayet, O. 1993. Translational frameshifting in the control of transposition in bacteria. Mol. Microbiol. 7. 497-503.
6. De Mot, R., Nagy, I., De Schrijver, A., Pattanapipitpaisal, P., Schoofs, G. and Vanderleyden, J. 1997. Structural analysis of the 6 kb cryptic plasmid pFAJ2600 from *Rhodococcus erythropolis* N186/21 and construction of *Escherichia coli-Rhodococcus* shuttle vectors. Microbiol. 143. 3137-3147.
7. Dodd, I. B. and Egan, J. B. 1990. Improved detection of helix-turn-helix DNA-binding motifs in protein sequences. Nucleic Acids Res. 18. 5019-5026.
8. Eaton, R. W. and Timmis, K. N. 1986. Spontaneous deletion of a 20-kilobase DNA segment carrying genes specifying isopropylbenzene metabolism in *Pseudomonas putida* RE204. J. Bacteriol. 168. 428-430.
9. Ewing, B. and Green, P. 1998. Base-calling of automated sequencer traces using phred. II. Error probabilities. Genome Res. 8.186-194.
10. Ewing, B., Hillier, L., Wendl, M. C. and Green, P. 1998. Base-calling of automated sequencer traces using phred. I. Accuracy assessment. Genome Res. 8. 75-185.
11. Fayolle, F., Hernandez, G., Le Roux, F. and Vandecasteele, J. -P. 1998. Isolation of two aerobic bacterial strains that degrade efficiently ethyl t-butyl ether (ETBE). Biotechnol. Lett. 20.283-286.
12. Frangeul, L., Nelson, K. E., Buchrieser, C., Danchin, A., Glaser, P. and Kunst, F. 1999. Cloning and assembly strategies in microbial genome projects. Microbiology. 145. 2625-2634.
13. Gallegos, M. -T., R., S., Bairoch, A., Hofmann, K. and Ramos, J. L. 1997. AraC/XylS family of transcriptional regulators. Microbiol. Mol. Biol. Rev. 61. 393-410.
14. Garnier, P. M., Auria, R., Augur, C. and Revah, S. 1999. Cometabolic biodegradation of methyl t-butyl ether by *Pseudomonas aeruginosa* grown on pentane. Appl. Microbiol. Biotechnol. 51.498-503.
15. Gibson, T. J. 1984. Studies on the Epstein-Barr virus genome. Ph. D. University of Cambridge, Cambridge, UK.
16. Hanson, J. R., Ackerman, C. E. and Scow, K. M. 1999. Biodegradation of methyl tert-butyl ether by a bacterial pure culture. Appl. Environ. Microbiol. 65. 4788-4792.
17. Hardison, L. K., Curry, S. S., Ciuffetti, L. M. and Hyman, M. R. 1997. Metabolism of diethyl ether and cometabolism of methyl tert-butyl ether by a filamentous fungus, a *Graphium* sp. Appl. Environ. Microbiol. 63. 3059-3067.
18. Hernandez-Perez, G., Fayolle, F. and Vandecasteele, J. -P. 2001. Biodegradation of ethyl t-butyl ether (ETBE), methyl t-butyl ether (MTBE) and t-amyl methyl ether (TAME) by *Gordonia terrae*. Appl. Microbiol. Biotechnol. 55 (1). 117-121.
19. Iborra, M. Izquierdo, J. F., Tejero, J. and CunIII, F. 1988. Getting the lead out with ethyl t-butyl ether. Chemtech. February 1988. 120-122.
20. Ishiguro, N. and Sato, G. 1984. Spontaneous deletion of citrate-utilizing ability promoted by insertion sequences. J. Bacteriol. 160.642-650.
21. Ishiguro, N. and Sato, G. 1988. Nucleotide sequence of insertion sequence IS3411, which flanks the citrate utilization determinant of transposon Tn3411. J. Bacteriol. 170. 1902-1906.
22. Iwabuchi, T. and Harayama, S. 1997. Biochemical and genetic characterization of 2-carboxybenzaldehyde dehydrogenase, an enzyme involved in phenanthrene degradation by *Nocardioides* sp. strain KP7. J. Bacteriol. 179. 6488-6494.
23. Laemmli, U. K. 1970. Cleavage of structural proteins during the assembly of the head of bacteriophage T4. Nature. 227. 680-685.
24. Lauer, B., Russwurm, R. and Bormann, C. 2000. Molecular characterization of two genes from *Streptomyces tendae* Tue901 required for the formation of the 4-formyl-4-imidazolin-2-one containing nucleoside moiety of the peptidyl nucleoside antibiotic nikkomycin. Eur. J. Biochem. 267. 1698-1706.
25. Mao, Y., Varoglu, M. and Sherman, D. H. 1999. Molecular characterization and analysis of the biosynthetic gene cluster for the antitumor antibiotic mitomycin C from *Streptomyces lavendulae* NRRL 2564. Chem. Biol. 6.251-263.
26. Meulien, P., Downing, R. G. and Broda, P. 1981. Excision of the 40 kb segment of the TOL plasmid from *Pseudomonas putida* mt-2 involves direct repeats. Mol. Gen. Genet. 184.97-101.
27. Mo, K., Lora, C. O., Wanken, A. E., Javanmardian, M., Yang, X. and Kulpa, C. F. 1997. Biodegradation of methyl t-butyl ether by pure bacterial cultures. Appl. Microbiol. Biotechnol. 47. 69-72.
28. Nagy, I., Schoofs, G., Compemolle, F., Proost, P., Vanderleyden, J. and De Mot, R. 1995. Degradation of the thiocarbamate herbicide EPTC (S-Ethyl Dipropylcarbamothioate) and biosafing by *Rhodococcus* sp. strain N186/21 involve an inducible cytochrome P-450 system and aldehyde dehydrogenase. J. Bacteriol. 177. 676-687.
29. Peterson, J. A., Lu, J. -Y., Geisselsoder, J., Graham-Lorence, S., Carmona, C., Witney, F. and Lorence, M. C. 1992. Cytochrome P-450terp. Isolation and purification of the protein and cloning and sequencing of its operon. J. Biol. Chem. 267. 14193-14203.
30. Prince, R. C. 2000. Biodegradation of methyl tertiajy-butyl ether (MTBE) and other fuel oxygenates. Crit. Rev. Microbiol. 26. 163-178.

31. Reddy, B. R., Shaw, L. E., Sayers, J. R. and Williams, P. A. 1994. Two identical copies of IS1246, a 1275 base pair sequence related to other bacterial insertion sequences, enclose the xyl genes on TOL plasmid pWW0. Microbiology. 140.2305-2307.

32. Reisch, M. S. 1994. Top 50 chemicals production rose modestly last year. Chem. Eng. News. 72. 12-16.

33. Schagger, H. and von Jagow, G. 1987. Tricine-sodium dodecyl sulfate-polyacrylamide gel electrophoresis for the separation of proteins in the range frbm 1 to 100 kDa. Anal. Biochem. 166. 368-379.

34. Seimieniak, D. R., Slightom, J. L. and Chung, S. -T. 1990. Nucleotide sequence of *Streptomyces fradiae* transposable element Tn4556: a class-II transposon related to Tn3. Gene. 86. 1-9.

35. Steffan, R. J., McKlay, K., Vainberg, S., Condee, C. W. and Zhang, D. 1997. Biodegradation of the gasoline oxygenates methyl tert-butyl ether, ethyl tert-butyl ether, and tert-amyl ether by propane-oxidizing bacteria. Appl. Environ. Microbiol. 63. 4216-4222.

36. Weirenga, R. K., Terpstra, P. and Hol, W. G. J. 1986. Prediction of the occurence of the ADP-binding βaβ-fold in proteins, using an amino-acid sequence fingerprint. J. Mol. Biol. 187. 101-107.

37. Yanisch-Perron, C., Viera, J., Messing, J. 1985. Improved M13 phage cloning vectors and host strains: nucleotide sequences of the M13 mp18 and pUC19 vectors gene. 33: 103-119.

38. Picardeau, M., C. Le Dantec, and V. Vincent. 2000. Analysis of the internal replication region of a mycobacterial linear plasmid. Microbiology 146:305-313.

The invention claimed is:

1. A recombinant *Escherchia coli* bacterium as deposited at the Collection Nationale de Cultures de Microorganismes (CNCM) on Apr. 19, 2001, under the name of *Escherichia coli* K12 (pGT220) and the accession number 1-2662.

2. A process for depolluting an aqueous effluent, a soil, a sludge, a sediment, a dredge tailing, a gas or a chemical waste contaminated with ETBE, comprising the step of contacting said effluent, soil, sludge, sediment, dredge tailing, gas or chemical waste with a bacterium of claim 1.

3. The process of claim 2, wherein the depollution takes place in a bioreactor.

4. The process of claim 2, wherein the depollution takes place in situ, by addition of bacteria of claim 1 to the contaminated medium.

5. The process of claim 2, wherein the bacteria are confined in biobarriers, biofilters, and/or biopiles.

6. The process of claim 2, wherein the effluent, soil, sludge, sediment, dredge tailing, gas or chemical waste to be decontaminated is additionally contacted with other microorganisms capable of degrading the contaminant or its degradative by-products.

7. An isolated nucleic acid consisting of SEQ ID NO: 1, 2, 3, 5, 7, 9, 11 or 13.

8. A method for rendering a cell able to cleave an ether fuel additive, comprising the step of introducing into said cell a nucleic acid of claim 7.

9. The method of claim 8, wherein said cell is a bacterium.

10. The method of claim 8, wherein said cell is a plant cell, a fungus or a yeast.

* * * * *

UNITED STATES PATENT AND TRADEMARK OFFICE

CERTIFICATE OF CORRECTION

PATENT NO. : 7,777,015 B2
APPLICATION NO. : 10/739003
DATED : August 17, 2010
INVENTOR(S) : Sylvie Chauvaux et al.

It is certified that error appears in the above-identified patent and that said Letters Patent is hereby corrected as shown below:

Title Page Item 57, Abstract, line 3, “nucleic add” should read -- nucleic acid --.

Signed and Sealed this

Sixteenth Day of November, 2010

David J. Kappos
*Director of the United States Patent and Trademark Office*